(12) United States Patent
Scheinblum et al.

(10) Patent No.: US 12,364,496 B2
(45) Date of Patent: Jul. 22, 2025

(54) DEVICES FOR REMOVING CLOT MATERIAL FROM INTRAVASCULARLY IMPLANTED DEVICES, AND ASSOCIATED SYSTEMS AND METHODS

(71) Applicant: Inari Medical, Inc., Irvine, CA (US)

(72) Inventors: Taylor Scheinblum, Newport Beach, CA (US); Derek Hauschka, Orange, CA (US); Hieu Minh Luong, Westminster, CA (US); John Coleman Thress, Capistrano Beach, CA (US); Philippe Marchand, Lake Forest, CA (US)

(73) Assignee: Inari Medical, Inc., Irvine, CA (US)

( * ) Notice: Subject to any disclaimer, the term of this patent is extended or adjusted under 35 U.S.C. 154(b) by 330 days.

(21) Appl. No.: 18/153,295

(22) Filed: Jan. 11, 2023

(65) Prior Publication Data
US 2023/0218310 A1    Jul. 13, 2023

Related U.S. Application Data

(60) Provisional application No. 63/298,399, filed on Jan. 11, 2022.

(51) Int. Cl.
*A61B 17/221* (2006.01)

(52) U.S. Cl.
CPC .... *A61B 17/221* (2013.01); *A61B 2017/2217* (2013.01)

(58) Field of Classification Search
CPC .......... A61B 17/221; A61B 2017/2217; A61B 17/320725; A61B 2017/22034; A61B 2017/22035; A61B 2017/2212
See application file for complete search history.

(56) References Cited

U.S. PATENT DOCUMENTS

| 1,101,890 | A | 6/1914 | Tunstead |
| 2,502,639 | A | 2/1948 | Blake |

(Continued)

FOREIGN PATENT DOCUMENTS

| AU | 2015210338 | 8/2015 |
| CN | 1501825 | 6/2004 |

(Continued)

OTHER PUBLICATIONS

US 12,114,876 B2, 10/2024, Quick et al. (withdrawn)

(Continued)

*Primary Examiner* — Julian W Woo
(74) *Attorney, Agent, or Firm* — Perkins Coie LLP

(57) ABSTRACT

Disclosed herein are devices for mechanically removing clot and/or other material from implants implanted in the vasculature of a patient, and associated systems and methods. In some embodiments, a system for removing clot material from an implant—such as a stent—includes a clot treatment device configured to be deployed within the stent, a handle, and a first elongate member and a second elongate member coupling the clot treatment device to the handle. The first elongate member couples a first end portion of the clot treatment device to the handle, and the second elongate member couples a second end portion of the clot treatment device to an actuator of the handle. Actuation of the actuator is configured to move the second elongate member relative to the first elongate member to move the first and second end portions toward one another to radially expand the clot treatment device.

19 Claims, 31 Drawing Sheets

FIG. 1B

(56) References Cited

U.S. PATENT DOCUMENTS

| | | |
|---|---|---|
| 2,707,954 A | 5/1955 | J.L., Sr. |
| 2,784,717 A | 3/1957 | Thompson |
| 2,846,179 A | 8/1958 | Monckton |
| 2,955,592 A | 10/1960 | Maclean |
| 3,088,363 A | 5/1963 | Sparks |
| 3,197,173 A | 7/1965 | Taubenheim |
| 3,383,131 A | 5/1968 | Rosfelder |
| 3,416,531 A | 12/1968 | Edwards |
| 3,435,826 A | 4/1969 | Fogarty |
| 3,438,607 A | 4/1969 | Williams et al. |
| 3,515,137 A | 6/1970 | Santomieri |
| 3,661,144 A | 5/1972 | Jensen et al. |
| 3,675,657 A | 7/1972 | Gauthier |
| 3,785,380 A | 1/1974 | Brumfield |
| 3,860,006 A | 1/1975 | Patel |
| 3,863,624 A | 2/1975 | Gram |
| 3,892,161 A | 7/1975 | Sokol |
| 3,923,065 A | 12/1975 | Nozick et al. |
| 4,030,503 A | 6/1977 | Clark, III |
| 4,034,642 A | 7/1977 | Iannucci et al. |
| 4,036,232 A | 7/1977 | Genese |
| 4,187,849 A | 2/1980 | Stim |
| 4,222,380 A | 9/1980 | Terayama |
| 4,243,040 A | 1/1981 | Beecher |
| 4,287,808 A | 9/1981 | Leonard et al. |
| 4,324,262 A | 4/1982 | Hall |
| 4,393,872 A | 7/1983 | Reznik et al. |
| 4,401,107 A | 8/1983 | Harber et al. |
| 4,469,100 A | 9/1984 | Hardwick |
| 4,523,738 A | 6/1985 | Raftis et al. |
| 4,551,862 A | 11/1985 | Haber |
| 4,604,094 A | 8/1986 | Shook |
| 4,611,594 A | 9/1986 | Grayhack et al. |
| 4,634,421 A | 1/1987 | Hegemann |
| 4,643,184 A | 2/1987 | Mobin-Uddin |
| 4,646,736 A | 3/1987 | Auth et al. |
| 4,650,466 A | 3/1987 | Luther |
| 4,693,257 A | 9/1987 | Markham |
| 4,705,518 A | 11/1987 | Baker et al. |
| 4,776,337 A | 10/1988 | Palmaz |
| 4,790,812 A | 12/1988 | Hawkins, Jr. et al. |
| 4,826,483 A | 5/1989 | Molnar, IV |
| 4,863,440 A | 9/1989 | Chin et al. |
| 4,870,953 A | 10/1989 | DonMichael et al. |
| 4,872,579 A | 10/1989 | Palmer |
| 4,880,408 A | 11/1989 | Cumes et al. |
| 4,883,458 A | 11/1989 | Shiber |
| 4,886,062 A | 12/1989 | Wiktor |
| 4,890,611 A | 1/1990 | Monfort et al. |
| 4,898,575 A | 2/1990 | Fischell et al. |
| 4,946,440 A | 8/1990 | Hall |
| 4,960,259 A | 10/1990 | Sunnanvader et al. |
| 4,978,341 A | 12/1990 | Niederhauser |
| 4,981,478 A | 1/1991 | Evard et al. |
| 5,030,201 A | 7/1991 | Palestrant |
| 5,053,008 A | 10/1991 | Bajaj |
| 5,059,178 A | 10/1991 | Ya |
| 5,100,423 A | 3/1992 | Fearnot |
| 5,127,626 A | 7/1992 | Hilal et al. |
| 5,129,910 A | 7/1992 | Phan et al. |
| 5,135,484 A | 8/1992 | Wright |
| 5,154,724 A | 10/1992 | Andrews |
| 5,158,533 A | 10/1992 | Strauss et al. |
| 5,158,564 A | 10/1992 | Schnepp-Pesch et al. |
| 5,192,274 A | 3/1993 | Bierman |
| 5,192,286 A | 3/1993 | Phan et al. |
| 5,192,290 A | 3/1993 | Hilal |
| 5,197,485 A | 3/1993 | Grooters |
| 5,234,403 A | 8/1993 | Yoda et al. |
| 5,242,461 A | 9/1993 | Kortenbach et al. |
| 5,244,619 A | 9/1993 | Burnham |
| 5,246,011 A | 9/1993 | Caillouette |
| 5,323,514 A | 6/1994 | Masuda et al. |
| 5,329,923 A | 7/1994 | Lundquist |
| 5,337,780 A | 8/1994 | Kee |
| 5,360,417 A | 11/1994 | Gravener et al. |
| 5,364,345 A | 11/1994 | Lowery et al. |
| 5,370,653 A * | 12/1994 | Cragg ............... A61M 25/0043 600/569 |
| 5,376,071 A | 12/1994 | Henderson |
| 5,376,101 A | 12/1994 | Green et al. |
| 5,378,230 A | 1/1995 | Mahurkar |
| 5,383,887 A | 1/1995 | Nadal |
| 5,389,100 A | 2/1995 | Bacich et al. |
| 5,391,152 A | 2/1995 | Patterson et al. |
| 5,419,774 A | 5/1995 | Willard et al. |
| 5,421,824 A | 6/1995 | Clement et al. |
| 5,429,610 A | 7/1995 | Vaillancourt |
| 5,443,443 A | 8/1995 | Shiber |
| 5,456,667 A | 10/1995 | Ham et al. |
| 5,476,450 A | 12/1995 | Ruggio |
| 5,484,418 A | 1/1996 | Quiachon et al. |
| 5,490,859 A | 2/1996 | Mische et al. |
| 5,496,365 A | 3/1996 | Sgro |
| 5,527,326 A | 6/1996 | Hermann et al. |
| 5,549,626 A | 8/1996 | Miller et al. |
| 5,591,137 A | 1/1997 | Stevens |
| 5,639,276 A | 6/1997 | Weinstock et al. |
| 5,653,684 A | 8/1997 | Laptewicz et al. |
| 5,662,703 A | 9/1997 | Yurek et al. |
| 5,746,758 A | 5/1998 | Nordgren et al. |
| 5,749,858 A | 5/1998 | Cramer |
| 5,769,816 A | 6/1998 | Barbut et al. |
| 5,782,817 A | 7/1998 | Franzel et al. |
| 5,800,457 A | 9/1998 | Gelbfish |
| 5,827,229 A | 10/1998 | Auth et al. |
| 5,846,251 A | 12/1998 | Hart |
| 5,860,938 A | 1/1999 | Lafontaine et al. |
| 5,873,866 A | 2/1999 | Kondo et al. |
| 5,873,882 A | 2/1999 | Straub et al. |
| 5,867,385 A | 3/1999 | Ikari et al. |
| 5,876,414 A | 3/1999 | Straub |
| 5,882,329 A * | 3/1999 | Patterson ............ A61B 17/3207 604/523 |
| 5,895,406 A | 4/1999 | Gray et al. |
| 5,908,435 A | 6/1999 | Samuels |
| 5,911,710 A | 6/1999 | Barry et al. |
| 5,911,728 A | 6/1999 | Sepetka et al. |
| 5,911,733 A | 6/1999 | Parodi |
| 5,911,754 A | 6/1999 | Kanesaka et al. |
| 5,941,869 A | 8/1999 | Patterson et al. |
| 5,947,985 A | 9/1999 | Imram |
| 5,951,539 A | 9/1999 | Nita et al. |
| 5,954,737 A | 9/1999 | Lee |
| 5,971,938 A | 10/1999 | Hart et al. |
| 5,971,958 A | 10/1999 | Zhang |
| 5,972,019 A | 10/1999 | Engelson et al. |
| 5,974,938 A | 11/1999 | Lloyd |
| 5,989,233 A | 11/1999 | Yoon |
| 5,993,483 A | 11/1999 | Gianotti |
| 6,017,335 A | 1/2000 | Burnham |
| 6,030,397 A | 2/2000 | Moneti et al. |
| 6,059,745 A | 5/2000 | Gelbfish |
| 6,059,814 A | 5/2000 | Ladd |
| 6,066,158 A | 5/2000 | Engelson et al. |
| 6,068,645 A | 5/2000 | Tu |
| 6,126,635 A | 10/2000 | Simpson et al. |
| 6,142,987 A | 11/2000 | Tsugita |
| 6,146,396 A | 11/2000 | Konya et al. |
| 6,146,403 A | 11/2000 | St. Germain |
| 6,152,144 A | 11/2000 | Lesh et al. |
| 6,152,909 A | 11/2000 | Bagaoisan et al. |
| 6,152,946 A | 11/2000 | Broome et al. |
| 6,156,055 A | 12/2000 | Ravenscroft |
| 6,159,230 A | 12/2000 | Samuels |
| 6,165,196 A | 12/2000 | Stack et al. |
| 6,168,579 B1 | 1/2001 | Tsugita |
| 6,179,859 B1 | 1/2001 | Bates et al. |
| 6,221,006 B1 | 4/2001 | Dubrul et al. |
| 6,228,060 B1 | 5/2001 | Howell |
| 6,238,412 B1 | 5/2001 | Dubrul et al. |
| 6,245,078 B1 | 6/2001 | Ouchi |
| 6,245,089 B1 | 6/2001 | Daniel et al. |
| 6,254,571 B1 | 7/2001 | Hart |

(56) References Cited

U.S. PATENT DOCUMENTS

| | | |
|---|---|---|
| 6,258,115 B1 | 7/2001 | Dubrul |
| 6,264,663 B1 | 7/2001 | Cano |
| 6,306,163 B1 | 10/2001 | Fitz |
| 6,322,572 B1 | 11/2001 | Lee |
| 6,350,271 B1 | 2/2002 | Kurz et al. |
| 6,361,545 B1 | 3/2002 | Macoviak et al. |
| 6,364,895 B1 | 4/2002 | Greenhalgh |
| 6,368,339 B1 | 4/2002 | Amplatz |
| 6,383,205 B1 | 5/2002 | Samson et al. |
| 6,402,771 B1 | 6/2002 | Palmer et al. |
| 6,413,235 B1 | 7/2002 | Parodi |
| 6,423,032 B2 | 7/2002 | Parodi |
| 6,432,122 B1 | 8/2002 | Gilson et al. |
| 6,436,085 B1 | 8/2002 | Lauer |
| 6,451,036 B1 | 9/2002 | Heitzmann et al. |
| 6,458,103 B1 | 10/2002 | Albert et al. |
| 6,475,236 B1 | 11/2002 | Roubin et al. |
| 6,485,502 B2 | 11/2002 | Don Michael et al. |
| 6,508,782 B1 | 1/2003 | Evans et al. |
| 6,511,492 B1 | 1/2003 | Rosenbluth et al. |
| 6,514,273 B1 | 2/2003 | Voss et al. |
| 6,530,923 B1 | 3/2003 | Dubrul et al. |
| 6,530,935 B2 | 3/2003 | Wensel et al. |
| 6,540,722 B1 | 4/2003 | Boyle et al. |
| 6,544,276 B1 | 4/2003 | Azizi |
| 6,544,278 B1 | 4/2003 | Vrba et al. |
| 6,544,279 B1 | 4/2003 | Hopkins et al. |
| 6,551,342 B1 | 4/2003 | Shen et al. |
| 6,564,828 B1 | 5/2003 | Ishida |
| 6,569,181 B1 | 5/2003 | Burns |
| 6,575,995 B1 | 6/2003 | Huter et al. |
| 6,589,263 B1 | 7/2003 | Hopkins et al. |
| 6,589,264 B1 | 7/2003 | Barbut et al. |
| 6,596,011 B2 | 7/2003 | Johnson et al. |
| 6,602,271 B2 | 8/2003 | Adams et al. |
| 6,605,074 B2 | 8/2003 | Zadno-azizi et al. |
| 6,605,102 B1 | 8/2003 | Mazzocchi et al. |
| 6,610,077 B1 | 8/2003 | Hancock et al. |
| 6,620,148 B1 | 9/2003 | Tsugita |
| 6,620,179 B2 | 9/2003 | Brook et al. |
| 6,620,182 B1 | 9/2003 | Khosravi et al. |
| 6,623,460 B1 | 9/2003 | Heck |
| 6,635,068 B1 | 10/2003 | Dubrul et al. |
| 6,645,222 B1 | 11/2003 | Parodi et al. |
| 6,660,013 B2 | 12/2003 | Rabiner et al. |
| 6,660,014 B2 | 12/2003 | Demarais et al. |
| 6,663,650 B2 | 12/2003 | Sepetka et al. |
| 6,679,893 B1 | 1/2004 | Tran |
| 6,692,504 B2 | 2/2004 | Kurz et al. |
| 6,699,260 B2 | 3/2004 | Dubrul et al. |
| 6,702,830 B1 | 3/2004 | Demarais et al. |
| 6,719,717 B1 | 4/2004 | Johnson et al. |
| 6,755,847 B2 | 6/2004 | Eskuri |
| 6,767,353 B1 | 7/2004 | Shiber |
| 6,790,204 B2 | 9/2004 | Zadno-azizi et al. |
| 6,800,080 B1 | 10/2004 | Bates |
| 6,818,006 B2 | 11/2004 | Douk et al. |
| 6,824,545 B2 | 11/2004 | Sepetka et al. |
| 6,824,550 B1 | 11/2004 | Noriega et al. |
| 6,824,553 B1 | 11/2004 | Gene et al. |
| 6,830,561 B2 | 12/2004 | Jansen et al. |
| 6,846,029 B1 | 1/2005 | Ragner et al. |
| 6,902,540 B2 | 6/2005 | Dorros et al. |
| 6,908,455 B2 | 6/2005 | Hajianpour |
| 6,939,361 B1 | 9/2005 | Kleshinski |
| 6,942,682 B2 | 9/2005 | Vrba et al. |
| 6,945,977 B2 | 9/2005 | Demarais et al. |
| 6,960,189 B2 | 11/2005 | Bates et al. |
| 6,960,222 B2 | 11/2005 | Vo et al. |
| 7,004,931 B2 | 2/2006 | Hogendijk |
| 7,004,954 B1 | 2/2006 | Voss et al. |
| 7,036,707 B2 | 5/2006 | Aota et al. |
| 7,041,084 B2 | 5/2006 | Fotjik |
| 7,052,500 B2 | 5/2006 | Bashiri et al. |
| 7,056,328 B2 | 6/2006 | Arnott |
| 7,063,707 B2 | 6/2006 | Bose et al. |
| 7,069,835 B2 | 7/2006 | Nishri et al. |
| 7,094,249 B1 | 8/2006 | Thomas et al. |
| 7,122,034 B2 | 10/2006 | Belhe et al. |
| 7,128,073 B1 | 10/2006 | van der Burg et al. |
| 7,152,605 B2 | 12/2006 | Khairkhahan et al. |
| 7,179,273 B1 | 2/2007 | Palmer et al. |
| 7,223,253 B2 | 5/2007 | Hogendijk |
| 7,232,432 B2 | 6/2007 | Fulton, III et al. |
| 7,244,243 B2 | 7/2007 | Lary |
| 7,285,126 B2 | 10/2007 | Sepetka et al. |
| 7,300,458 B2 | 11/2007 | Henkes et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,481,805 B2 | 1/2009 | Magnusson |
| 7,534,234 B2 | 5/2009 | Fotjik |
| 7,578,830 B2 | 8/2009 | Kusleika et al. |
| 7,621,870 B2 | 11/2009 | Berrada et al. |
| 7,674,247 B2 | 3/2010 | Fotjik |
| 7,678,131 B2 | 3/2010 | Muller |
| 7,691,121 B2 | 4/2010 | Rosenbluth et al. |
| 7,695,458 B2 | 4/2010 | Belley et al. |
| 7,713,282 B2 | 5/2010 | Frazier et al. |
| 7,722,641 B2 | 5/2010 | van der Burg et al. |
| 7,763,010 B2 | 7/2010 | Evans et al. |
| 7,766,934 B2 | 8/2010 | Pal et al. |
| 7,775,501 B2 | 8/2010 | Kees |
| 7,780,696 B2 | 8/2010 | Daniel et al. |
| 7,815,608 B2 | 10/2010 | Schafersman et al. |
| 7,837,630 B2 | 11/2010 | Nieoson et al. |
| 7,905,877 B1 | 3/2011 | Oscar et al. |
| 7,905,896 B2 | 3/2011 | Straub |
| 7,938,809 B2 | 5/2011 | Lampropoulos et al. |
| 7,938,820 B2 | 5/2011 | Webster et al. |
| 7,967,790 B2 | 6/2011 | Whiting et al. |
| 7,976,511 B2 | 7/2011 | Fotjik |
| 7,993,302 B2 | 8/2011 | Hebert et al. |
| 7,993,363 B2 | 8/2011 | Demond et al. |
| 8,021,351 B2 | 9/2011 | Boldenow et al. |
| 8,043,313 B2 | 10/2011 | Krollk et al. |
| 8,052,640 B2 | 11/2011 | Fiorella et al. |
| 8,057,496 B2 | 11/2011 | Fischer, Jr. |
| 8,057,497 B1 | 11/2011 | Raju et al. |
| 8,066,757 B2 | 11/2011 | Ferrera et al. |
| 8,070,694 B2 | 12/2011 | Galdonik et al. |
| 8,070,769 B2 | 12/2011 | Broome |
| 8,070,791 B2 | 12/2011 | Ferrera et al. |
| 8,075,510 B2 | 12/2011 | Aklog et al. |
| 8,080,032 B2 | 12/2011 | van der Burg et al. |
| 8,088,140 B2 | 1/2012 | Ferrera et al. |
| 8,092,486 B2 | 1/2012 | Berrada et al. |
| 8,100,935 B2 | 1/2012 | Rosenbluth et al. |
| 8,109,962 B2 | 2/2012 | Pal |
| 8,118,275 B2 | 2/2012 | Mialhe |
| 8,118,829 B2 | 2/2012 | Carrison et al. |
| 8,187,465 B2 | 5/2012 | Nierich |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,267,897 B2 | 9/2012 | Wells |
| 8,298,257 B2 | 10/2012 | Sepetka et al. |
| 8,317,748 B2 | 11/2012 | Fiorella et al. |
| 8,337,450 B2 | 12/2012 | Fotjik |
| RE43,902 E | 1/2013 | Hopkins et al. |
| 8,343,167 B2 | 1/2013 | Henson |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,439,858 B2 | 5/2013 | Huang et al. |
| 8,480,708 B2 | 7/2013 | Kassab et al. |
| 8,486,105 B2 | 7/2013 | Demond et al. |
| 8,491,539 B2 | 7/2013 | Fotjik |
| 8,512,352 B2 | 8/2013 | Martin |
| 8,523,897 B2 | 9/2013 | van der Burg et al. |
| 8,529,596 B2 | 9/2013 | Grandfield et al. |
| 8,535,283 B2 | 9/2013 | Heaton et al. |
| 8,535,334 B2 | 9/2013 | Martin |

(56) References Cited

U.S. PATENT DOCUMENTS

| | | |
|---|---|---|
| 8,535,343 B2 | 9/2013 | van der Burg et al. |
| 8,545,526 B2 | 10/2013 | Martin et al. |
| 8,568,432 B2 | 10/2013 | Straub |
| 8,568,465 B2 | 10/2013 | Freudenthal et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,754 B2 | 12/2013 | Wensel et al. |
| 8,613,717 B2 | 12/2013 | Aklog et al. |
| 8,632,584 B2 | 1/2014 | Henkes et al. |
| 8,647,367 B2 | 2/2014 | Kassab et al. |
| 8,657,867 B2 | 2/2014 | Dorn et al. |
| 8,696,622 B2 | 4/2014 | Fiorella et al. |
| 8,715,314 B1 | 5/2014 | Janardhan et al. |
| 8,721,714 B2 | 5/2014 | Kelley |
| 8,753,322 B2 | 6/2014 | Hu et al. |
| 8,764,730 B2 | 7/2014 | Taber |
| 8,771,289 B2 | 7/2014 | Mohluddin et al. |
| 8,777,893 B2 | 7/2014 | Malewicz |
| 8,784,441 B2 | 7/2014 | Rosenbluth et al. |
| 8,784,442 B2 | 7/2014 | Jones et al. |
| 8,784,469 B2 | 7/2014 | Kassab |
| 8,795,305 B2 | 8/2014 | Martin et al. |
| 8,795,317 B2 | 8/2014 | Grandfield et al. |
| 8,795,345 B2 | 8/2014 | Grandfield et al. |
| 8,801,748 B2 | 8/2014 | Martin |
| 8,808,259 B2 | 8/2014 | Walton et al. |
| 8,814,927 B2 | 8/2014 | Shin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,834,519 B2 | 9/2014 | van der Burg et al. |
| 8,845,621 B2 | 9/2014 | Fotjik |
| 8,852,226 B2 | 10/2014 | Gilson et al. |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,956,384 B2 | 2/2015 | Berrada et al. |
| 8,992,504 B2 | 3/2015 | Castella et al. |
| 9,005,172 B2 | 4/2015 | Chung |
| 9,011,551 B2 | 4/2015 | Oral et al. |
| 9,028,401 B1 | 5/2015 | Bacich et al. |
| 9,044,575 B2 | 6/2015 | Beasley et al. |
| 9,072,537 B2 | 7/2015 | Grandfield et al. |
| 9,078,682 B2 | 7/2015 | Lenker et al. |
| 9,101,382 B2 | 8/2015 | Krolik et al. |
| 9,125,683 B2 | 9/2015 | Farhangnia et al. |
| 9,126,016 B2 | 9/2015 | Fulton |
| 9,126,020 B2 | 9/2015 | Farhangnia et al. |
| 9,149,609 B2 | 10/2015 | Ansel et al. |
| 9,155,552 B2 | 10/2015 | Ulm, III |
| 9,161,766 B2 | 10/2015 | Slee et al. |
| 9,168,043 B2 | 10/2015 | van der Burg et al. |
| 9,173,668 B2 | 11/2015 | Ulm, III |
| 9,186,487 B2 | 11/2015 | Dubrul et al. |
| D744,639 S | 12/2015 | Aklog et al. |
| 9,204,887 B2 | 12/2015 | Cully et al. |
| 9,216,277 B2 | 12/2015 | Myers |
| 9,241,669 B2 | 1/2016 | Pugh et al. |
| 9,358,037 B2 | 1/2016 | Farhangnia et al. |
| 9,254,352 B2 | 2/2016 | Kumar et al. |
| 9,259,237 B2 | 2/2016 | Quick et al. |
| 9,265,512 B2 | 2/2016 | Carrison et al. |
| 9,283,066 B2 | 3/2016 | Hopkins et al. |
| 9,301,769 B2 | 4/2016 | Brady et al. |
| 9,351,747 B2 | 5/2016 | Kugler et al. |
| 9,402,938 B2 | 8/2016 | Aklog et al. |
| 9,439,664 B2 | 9/2016 | Sos |
| 9,439,751 B2 | 9/2016 | White et al. |
| 9,456,834 B2 | 10/2016 | Folk |
| 9,463,035 B1 | 10/2016 | Greenhalgh et al. |
| 9,463,036 B2 | 10/2016 | Brady et al. |
| 9,492,635 B2 | 11/2016 | Beasley et al. |
| 9,526,864 B2 | 12/2016 | Quick |
| 9,526,865 B2 | 12/2016 | Quick |
| 9,532,792 B2 | 1/2017 | Galdonik et al. |
| 9,545,464 B2 | 1/2017 | Roche et al. |
| 9,566,073 B2 | 2/2017 | Kassab et al. |
| 9,566,179 B2 | 2/2017 | Andreas et al. |
| 9,566,424 B2 | 2/2017 | Pessin |
| 9,579,116 B1 | 2/2017 | Nguyen et al. |
| 9,581,942 B1 | 2/2017 | Shippert |
| 9,616,213 B2 | 4/2017 | Furnish et al. |
| 9,636,206 B2 | 5/2017 | Nguyen et al. |
| 9,643,035 B2 | 5/2017 | Mastenbroek |
| 9,662,129 B2 | 5/2017 | Galdonik et al. |
| 9,700,332 B2 | 7/2017 | Marchand et al. |
| 9,717,488 B2 | 8/2017 | Kassab et al. |
| 9,717,514 B2 | 8/2017 | Martin et al. |
| 9,717,519 B2 | 8/2017 | Rosenbluth et al. |
| 9,744,024 B2 | 8/2017 | Nguyen et al. |
| 9,757,137 B2 | 9/2017 | Krolik et al. |
| 9,827,084 B2 | 11/2017 | Bonnette et al. |
| 9,827,364 B2 | 11/2017 | Peticca et al. |
| 9,844,386 B2 | 12/2017 | Nguyen et al. |
| 9,844,387 B2 | 12/2017 | Marchand et al. |
| 9,844,643 B2 | 12/2017 | Beasley et al. |
| 9,848,975 B2 | 12/2017 | Hauser |
| 9,849,014 B2 | 12/2017 | Kusleika |
| 9,884,387 B2 | 2/2018 | Plha |
| 9,937,321 B2 | 4/2018 | Welch et al. |
| 9,962,178 B2 | 5/2018 | Greenhalgh et al. |
| 9,980,813 B2 | 5/2018 | Eller |
| 9,999,493 B2 | 6/2018 | Nguyen et al. |
| 10,004,531 B2 | 6/2018 | Rosenbluth et al. |
| 10,010,335 B2 | 7/2018 | Greenhalgh et al. |
| 10,016,206 B1 | 7/2018 | Yang |
| 10,016,266 B2 | 7/2018 | Hauser |
| 10,028,759 B2 | 7/2018 | Wallace et al. |
| 10,045,790 B2 | 8/2018 | Cox et al. |
| 10,058,339 B2 | 8/2018 | Galdonik et al. |
| 10,098,651 B2 | 10/2018 | Marchand et al. |
| 10,130,385 B2 | 11/2018 | Farhangnia et al. |
| 10,130,795 B2 | 11/2018 | Parhangnia et al. |
| 10,179,224 B2 | 1/2019 | Yang et al. |
| 10,183,147 B2 | 1/2019 | Yang et al. |
| 10,183,159 B2 | 1/2019 | Nobles et al. |
| 10,188,829 B2 | 1/2019 | Beasley et al. |
| 10,195,320 B2 | 2/2019 | Fisher et al. |
| 10,226,263 B2 | 3/2019 | Look et al. |
| 10,238,406 B2 | 3/2019 | Cox et al. |
| 10,271,864 B2 | 4/2019 | Greenhalgh et al. |
| 10,327,883 B2 | 6/2019 | Yachia |
| 10,335,186 B2 | 7/2019 | Rosenbluth et al. |
| 10,342,571 B2 | 7/2019 | Marchand et al. |
| 10,349,960 B2 | 7/2019 | Quick |
| 10,383,644 B2 | 8/2019 | Molael et al. |
| 10,383,983 B2 | 8/2019 | Aklog et al. |
| 10,384,034 B2 | 8/2019 | Carrison et al. |
| 10,426,510 B2 | 10/2019 | Farhangnia et al. |
| 10,426,644 B2 | 10/2019 | Shrivastava et al. |
| 10,441,745 B2 | 10/2019 | Yang et al. |
| 10,456,151 B2 | 10/2019 | Slee et al. |
| 10,456,555 B2 | 10/2019 | Carrison et al. |
| 10,471,234 B2 | 11/2019 | Taber |
| 10,478,535 B2 | 11/2019 | Ogle |
| 10,485,952 B2 | 11/2019 | Carrison et al. |
| 10,492,805 B2 | 12/2019 | Culbert et al. |
| 10,524,811 B2 | 1/2020 | Marchand et al. |
| 10,531,883 B1 | 1/2020 | Deville et al. |
| 10,537,710 B2 | 1/2020 | Jalgaonkar et al. |
| 10,561,440 B2 | 2/2020 | Look et al. |
| 10,588,655 B2 | 3/2020 | Rosenbluth et al. |
| 10,648,268 B2 | 5/2020 | Jaffrey et al. |
| 10,661,053 B2 | 5/2020 | Yang et al. |
| 10,695,159 B2 | 6/2020 | Hauser |
| 10,709,471 B2 | 7/2020 | Rosenbluth et al. |
| 10,716,880 B2 | 7/2020 | Culbert et al. |
| 10,729,455 B2 | 8/2020 | Goyal et al. |
| 10,743,907 B2 | 8/2020 | Bruzzi et al. |
| 10,772,636 B2 | 9/2020 | Kassab et al. |
| 10,779,852 B2 | 9/2020 | Bruzzi et al. |
| 10,779,855 B2 | 9/2020 | Garrison |

(56) References Cited

U.S. PATENT DOCUMENTS

| | | |
|---|---|---|
| 10,792,056 B2 | 10/2020 | Vale et al. |
| 10,799,331 B2 | 10/2020 | Hauser |
| 10,799,671 B2 | 10/2020 | Shimada et al. |
| 10,813,663 B2 | 10/2020 | Bruzzi et al. |
| 10,828,061 B2 | 11/2020 | Bonnette et al. |
| 10,835,711 B2 | 11/2020 | Yang et al. |
| 10,874,421 B2 | 12/2020 | Bruzzi et al. |
| 10,912,577 B2 | 2/2021 | Marchand et al. |
| 10,926,060 B2 | 2/2021 | Stern et al. |
| 10,939,932 B1 | 3/2021 | Yang |
| 10,953,195 B2 | 3/2021 | Jalgaonkar et al. |
| 10,960,114 B2 | 3/2021 | Goisis |
| 10,967,111 B2 | 4/2021 | Iida |
| 10,994,063 B2 | 5/2021 | Fisher et al. |
| 11,000,682 B2 | 5/2021 | Merritt et al. |
| 11,013,523 B2 | 5/2021 | Arad Hadar |
| 11,058,445 B2 | 7/2021 | Cox et al. |
| 11,058,451 B2 | 7/2021 | Marchand et al. |
| 11,065,019 B1 | 7/2021 | Chou et al. |
| 11,065,028 B2 | 7/2021 | Parhangnia et al. |
| 11,147,571 B2 | 10/2021 | Cox et al. |
| 11,147,948 B2 | 10/2021 | Beasley et al. |
| 11,147,949 B2 | 10/2021 | Yang et al. |
| 11,154,314 B2 | 10/2021 | Quick |
| 11,166,703 B2 | 11/2021 | Kassab et al. |
| 11,185,664 B2 | 11/2021 | Carrison et al. |
| 11,197,684 B1 | 12/2021 | Ngo et al. |
| 11,213,356 B2 | 1/2022 | Tanner et al. |
| 11,224,450 B2 | 1/2022 | Chou et al. |
| 11,224,721 B2 | 1/2022 | Carrison et al. |
| 11,253,277 B2 | 2/2022 | Buck et al. |
| 11,259,821 B2 | 3/2022 | Buck et al. |
| 11,266,825 B2 | 3/2022 | Peter et al. |
| 11,278,307 B2 | 3/2022 | Bruzzi et al. |
| 11,305,094 B2 | 4/2022 | Carrison et al. |
| 11,317,939 B2 | 5/2022 | Bruzzi et al. |
| 11,337,714 B2 | 5/2022 | Ferrera et al. |
| 11,383,064 B2 | 7/2022 | Carrison et al. |
| 11,395,903 B2 | 7/2022 | Carrison et al. |
| 11,406,418 B2 | 8/2022 | Bruzzi et al. |
| 11,419,621 B2 | 8/2022 | Goyal et al. |
| 11,433,218 B2 | 9/2022 | Quick et al. |
| 11,439,799 B2 | 9/2022 | Buck et al. |
| 11,457,936 B2 | 10/2022 | Buck et al. |
| 11,478,262 B2 | 10/2022 | Ngo et al. |
| 11,529,158 B2 | 12/2022 | Hauser |
| 11,553,935 B2 | 1/2023 | Buck et al. |
| 11,553,942 B2 | 1/2023 | Bonnette et al. |
| 11,554,005 B2 | 1/2023 | Merritt et al. |
| 11,559,382 B2 | 1/2023 | Merritt et al. |
| 11,576,691 B2 | 2/2023 | Chou et al. |
| 11,589,880 B2 | 2/2023 | Aklog et al. |
| 11,596,768 B2 | 3/2023 | Stern et al. |
| 11,607,483 B2 | 3/2023 | Iida |
| 11,633,272 B2 | 4/2023 | Buck et al. |
| 11,638,637 B2 | 5/2023 | Buck et al. |
| 11,642,209 B2 | 5/2023 | Merritt et al. |
| 11,648,028 B2 | 5/2023 | Rosenbluth et al. |
| 11,672,561 B2 | 6/2023 | Look et al. |
| 11,678,905 B2 | 6/2023 | Look et al. |
| 11,697,011 B2 | 7/2023 | Merritt et al. |
| 11,697,012 B2 | 7/2023 | Merritt et al. |
| 11,724,052 B2 | 8/2023 | White et al. |
| 11,730,925 B2 | 8/2023 | Saadat et al. |
| 11,744,691 B2 | 9/2023 | Merritt et al. |
| 11,806,033 B2 | 11/2023 | Marchand et al. |
| 11,819,228 B2 | 11/2023 | Buck et al. |
| 11,832,837 B2 | 12/2023 | Hauser |
| 11,832,838 B2 | 12/2023 | Hauser |
| 11,833,023 B2 | 12/2023 | Hauser |
| 11,839,393 B2 | 12/2023 | Hauser |
| 11,844,921 B2 | 12/2023 | Merritt et al. |
| 11,849,963 B2 | 12/2023 | Quick |
| 11,865,291 B2 | 1/2024 | Merritt et al. |
| 11,890,180 B2 | 2/2024 | Merritt et al. |
| 11,918,243 B2 | 3/2024 | Marchand et al. |
| 11,918,244 B2 | 3/2024 | Marchand et al. |
| 11,925,369 B2 | 3/2024 | Hauser |
| 11,937,834 B2 | 3/2024 | Dinh |
| 11,937,838 B2 | 3/2024 | Cox et al. |
| 11,963,861 B2 | 4/2024 | Strauss et al. |
| 11,969,178 B2 | 4/2024 | Hauser |
| 11,969,331 B2 | 4/2024 | Merritt et al. |
| 11,969,332 B2 | 4/2024 | Merritt et al. |
| 11,969,333 B2 | 4/2024 | Merritt et al. |
| 11,974,909 B2 | 5/2024 | Merritt et al. |
| 11,974,910 B2 | 5/2024 | Merritt et al. |
| 11,980,537 B2 | 5/2024 | Merritt et al. |
| 11,986,382 B2 | 5/2024 | Merritt et al. |
| 11,998,436 B2 | 6/2024 | Merritt et al. |
| 12,016,580 B2 | 6/2024 | Quick et al. |
| 12,023,057 B2 | 7/2024 | Hauser |
| 12,102,343 B2 | 10/2024 | Quick |
| 12,109,384 B2 | 10/2024 | Merritt et al. |
| 12,156,669 B2 | 12/2024 | Quick et al. |
| 12,239,333 B2 | 3/2025 | Quick et al. |
| 2001/0004699 A1 | 6/2001 | Gittings et al. |
| 2001/0031981 A1 | 10/2001 | Evans et al. |
| 2001/0041881 A1 | 11/2001 | Sarge et al. |
| 2001/0041909 A1 | 11/2001 | Tsugita et al. |
| 2001/0049486 A1 | 12/2001 | Evans et al. |
| 2001/0051810 A1 | 12/2001 | Dubrul et al. |
| 2002/0022858 A1 | 2/2002 | Demond et al. |
| 2002/0022859 A1 | 2/2002 | Hogendijk |
| 2002/0026211 A1 | 2/2002 | Khosravi et al. |
| 2002/0032455 A1 | 3/2002 | Boock et al. |
| 2002/0049452 A1 | 4/2002 | Kurz et al. |
| 2002/0095161 A1 | 7/2002 | Dhindsa |
| 2002/0095171 A1 | 7/2002 | Belef |
| 2002/0111648 A1 | 8/2002 | Kusleika et al. |
| 2002/0120277 A1 | 8/2002 | Hauschild et al. |
| 2002/0147458 A1 | 10/2002 | Hiblar et al. |
| 2002/0151918 A1 | 10/2002 | Lafontaine et al. |
| 2002/0156457 A1 | 10/2002 | Fisher |
| 2002/0161392 A1 | 10/2002 | Dubrul |
| 2002/0169474 A1 | 11/2002 | Kusleika |
| 2002/0173819 A1 | 11/2002 | Leeflang et al. |
| 2002/0188276 A1 | 12/2002 | Evans et al. |
| 2003/0004536 A1 | 1/2003 | Boylan et al. |
| 2003/0023263 A1 | 1/2003 | Krolik et al. |
| 2003/0069601 A1 | 4/2003 | Nowakowski et al. |
| 2003/0083693 A1 | 5/2003 | Daniel et al. |
| 2003/0100919 A1 | 5/2003 | Hopkins et al. |
| 2003/0114875 A1 | 6/2003 | Sjostrom |
| 2003/0116731 A1 | 6/2003 | Hartley |
| 2003/0125663 A1 | 7/2003 | Coleman et al. |
| 2003/0135151 A1 | 7/2003 | Deng |
| 2003/0135230 A1 | 7/2003 | Massey et al. |
| 2003/0135258 A1 | 7/2003 | Andreas et al. |
| 2003/0153873 A1 | 8/2003 | Luther et al. |
| 2003/0153973 A1 | 8/2003 | Soun et al. |
| 2003/0168068 A1 | 9/2003 | Poole et al. |
| 2003/0176884 A1 | 9/2003 | Berrada et al. |
| 2003/0191425 A1 | 10/2003 | Rosenblatt et al. |
| 2003/0191516 A1 | 10/2003 | Weldon et al. |
| 2003/0208224 A1 | 11/2003 | Broome |
| 2003/0216774 A1 | 11/2003 | Larson |
| 2003/0225379 A1 | 12/2003 | Schaffer et al. |
| 2004/0019310 A1 | 1/2004 | Hogendijk |
| 2004/0039351 A1 | 2/2004 | Barrett |
| 2004/0039412 A1 | 2/2004 | Isshiki et al. |
| 2004/0068288 A1 | 4/2004 | Palmer et al. |
| 2004/0073243 A1 | 4/2004 | Sepetka et al. |
| 2004/0098033 A1 | 5/2004 | Leeflang et al. |
| 2004/0102807 A1 | 5/2004 | Kusleika et al. |
| 2004/0122359 A1 | 6/2004 | Wenz et al. |
| 2004/0127936 A1 | 7/2004 | Salahieh et al. |
| 2004/0133232 A1 | 7/2004 | Rosenbluth et al. |
| 2004/0138525 A1 | 7/2004 | Saadat et al. |
| 2004/0138692 A1 | 7/2004 | Phung et al. |
| 2004/0167567 A1 | 8/2004 | Cano et al. |
| 2004/0199201 A1 | 10/2004 | Kellett et al. |
| 2004/0199202 A1 | 10/2004 | Dubrul et al. |
| 2004/0260344 A1 | 12/2004 | Lyons et al. |

(56) References Cited

U.S. PATENT DOCUMENTS

| | | |
|---|---|---|
| 2004/0267272 A1 | 12/2004 | Henniges et al. |
| 2005/0004534 A1 | 1/2005 | Lockwood et al. |
| 2005/0033172 A1 | 2/2005 | Dubrul et al. |
| 2005/0038468 A1 | 2/2005 | Panetta et al. |
| 2005/0054995 A1 | 3/2005 | Barzell et al. |
| 2005/0055047 A1 | 3/2005 | Greenhalgh |
| 2005/0080398 A1 | 4/2005 | Markel et al. |
| 2005/0085769 A1 | 4/2005 | MacMahon et al. |
| 2005/0085826 A1 | 4/2005 | Nair et al. |
| 2005/0085846 A1 | 4/2005 | Carrison et al. |
| 2005/0085849 A1 | 4/2005 | Sepetka et al. |
| 2005/0119668 A1 | 6/2005 | Teague et al. |
| 2005/0131387 A1 | 6/2005 | Pursley |
| 2005/0177132 A1 | 8/2005 | Lentz et al. |
| 2005/0187570 A1 | 8/2005 | Nguyen et al. |
| 2005/0203605 A1 | 9/2005 | Dolan |
| 2005/0283165 A1 | 12/2005 | Gadberry |
| 2005/0283166 A1 | 12/2005 | Greenhalgh et al. |
| 2005/0283186 A1 | 12/2005 | Berrada et al. |
| 2006/0020286 A1 | 1/2006 | Niermann |
| 2006/0042786 A1 | 3/2006 | West |
| 2006/0047286 A1 | 3/2006 | West |
| 2006/0074401 A1 | 4/2006 | Ross |
| 2006/0079787 A1 | 4/2006 | Whiting et al. |
| 2006/0085952 A1 | 4/2006 | Kaneko et al. |
| 2006/0089533 A1 | 4/2006 | Ziegler et al. |
| 2006/0100662 A1 | 5/2006 | Daniel et al. |
| 2006/0149219 A1 | 7/2006 | Calderon |
| 2006/0155305 A1 | 7/2006 | Freudenthal et al. |
| 2006/0173525 A1 | 8/2006 | Behl et al. |
| 2006/0195137 A1 | 8/2006 | Sepetka et al. |
| 2006/0200221 A1 | 9/2006 | Malewicz |
| 2006/0217664 A1 | 9/2006 | Hattler et al. |
| 2006/0224177 A1 | 10/2006 | Finitsis |
| 2006/0229645 A1 | 10/2006 | Bonnette et al. |
| 2006/0247500 A1 | 11/2006 | Voegele et al. |
| 2006/0253145 A1 | 11/2006 | Lucas |
| 2006/0264905 A1 | 11/2006 | Eskridge et al. |
| 2006/0276874 A1 | 12/2006 | Wilson et al. |
| 2006/0282111 A1 | 12/2006 | Morsi |
| 2006/0293696 A1 | 12/2006 | Fahey et al. |
| 2007/0010787 A1 | 1/2007 | Hackett et al. |
| 2007/0038225 A1 | 2/2007 | Osborne |
| 2007/0060911 A1 | 3/2007 | Webster et al. |
| 2007/0093744 A1 | 4/2007 | Elmaleh |
| 2007/0112374 A1 | 5/2007 | Paul, Jr. et al. |
| 2007/0118165 A1 | 5/2007 | DeMello et al. |
| 2007/0149996 A1 | 6/2007 | Coughlin |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0213765 A1 | 9/2007 | Adams et al. |
| 2007/0233043 A1 | 10/2007 | Dayton et al. |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0087853 A1 | 4/2008 | Kees |
| 2008/0088055 A1 | 4/2008 | Ross |
| 2008/0157017 A1 | 7/2008 | Macatangay et al. |
| 2008/0167678 A1 | 7/2008 | Morsi |
| 2008/0183136 A1 | 7/2008 | Lenker et al. |
| 2008/0228209 A1 | 9/2008 | DeMello et al. |
| 2008/0234715 A1 | 9/2008 | Pesce et al. |
| 2008/0234722 A1 | 9/2008 | Bonnette et al. |
| 2008/0262528 A1 | 10/2008 | Martin |
| 2008/0269798 A1 | 10/2008 | Ramzipoor et al. |
| 2008/0294096 A1 | 11/2008 | Uber et al. |
| 2008/0300466 A1 | 12/2008 | Gresham |
| 2008/0312681 A1 | 12/2008 | Ansel et al. |
| 2009/0018566 A1 | 1/2009 | Escudero et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0076417 A1 | 3/2009 | Jones |
| 2009/0082857 A1 | 3/2009 | Lashinski et al. |
| 2009/0160112 A1 | 6/2009 | Ostrovsky |
| 2009/0163846 A1 | 6/2009 | Aklog et al. |
| 2009/0182362 A1 | 7/2009 | Thompson et al. |
| 2009/0192495 A1 | 7/2009 | Ostrovsky et al. |
| 2009/0281525 A1 | 11/2009 | Harding et al. |
| 2009/0292307 A1 | 11/2009 | Razack |
| 2009/0299393 A1 | 12/2009 | Martin et al. |
| 2009/0312786 A1 | 12/2009 | Trask et al. |
| 2010/0016837 A1 | 1/2010 | Howat |
| 2010/0030256 A1 | 2/2010 | Dubrul et al. |
| 2010/0042136 A1 | 2/2010 | Berrada et al. |
| 2010/0087844 A1 | 4/2010 | Fischer, Jr. |
| 2010/0087850 A1 | 4/2010 | Razack |
| 2010/0094201 A1 | 4/2010 | Mallaby |
| 2010/0106081 A1 | 4/2010 | Brandeis |
| 2010/0114017 A1 | 5/2010 | Lenker et al. |
| 2010/0114113 A1 | 5/2010 | Dubrul et al. |
| 2010/0121312 A1 | 5/2010 | Gielenz et al. |
| 2010/0137846 A1 | 6/2010 | Desai et al. |
| 2010/0190156 A1 | 7/2010 | Van Wordragen et al. |
| 2010/0204712 A1 | 8/2010 | Mallaby |
| 2010/0217276 A1 | 8/2010 | Garrison et al. |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0009950 A1 | 1/2011 | Grandfield et al. |
| 2011/0034986 A1 | 2/2011 | Chou et al. |
| 2011/0034987 A1 | 2/2011 | Kennedy |
| 2011/0054405 A1 | 3/2011 | Whiting et al. |
| 2011/0060212 A1 | 3/2011 | Slee et al. |
| 2011/0071503 A1 | 3/2011 | Takagi et al. |
| 2011/0087173 A1 | 4/2011 | Sibbitt, Jr. et al. |
| 2011/0118817 A1 | 5/2011 | Gunderson et al. |
| 2011/0125181 A1 | 5/2011 | Brady et al. |
| 2011/0144592 A1 | 6/2011 | Wong et al. |
| 2011/0152823 A1 | 6/2011 | Mohiuddin et al. |
| 2011/0152889 A1 | 6/2011 | Ashland |
| 2011/0152993 A1 | 6/2011 | Marchand et al. |
| 2011/0160742 A1 | 6/2011 | Ferrera et al. |
| 2011/0160763 A1 | 6/2011 | Ferrera et al. |
| 2011/0190806 A1 | 8/2011 | Wittens |
| 2011/0196309 A1 | 8/2011 | Wells |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0245807 A1 | 10/2011 | Sakata et al. |
| 2011/0251629 A1 | 10/2011 | Galdonik et al. |
| 2011/0264132 A1 | 10/2011 | Strauss et al. |
| 2011/0264133 A1 | 10/2011 | Hanlon et al. |
| 2011/0265681 A1 | 11/2011 | Allen et al. |
| 2011/0288529 A1 | 11/2011 | Fulton |
| 2011/0288572 A1 | 11/2011 | Martin |
| 2011/0309037 A1 | 12/2011 | Lee |
| 2011/0319917 A1 | 12/2011 | Ferrera et al. |
| 2012/0059309 A1 | 3/2012 | di Palma et al. |
| 2012/0059356 A1 | 3/2012 | di Palma et al. |
| 2012/0083824 A1 | 4/2012 | Berrada et al. |
| 2012/0083868 A1 | 4/2012 | Shrivastava |
| 2012/0089216 A1 | 4/2012 | Rapaport et al. |
| 2012/0095448 A1 | 4/2012 | Kajii |
| 2012/0101480 A1 | 4/2012 | Ingle et al. |
| 2012/0101510 A1 | 4/2012 | Lenker et al. |
| 2012/0109109 A1 | 5/2012 | Kajii |
| 2012/0138832 A1 | 6/2012 | Townsend |
| 2012/0143123 A1 | 6/2012 | Agnew |
| 2012/0143239 A1 | 6/2012 | Aklog et al. |
| 2012/0165919 A1 | 6/2012 | Cox et al. |
| 2012/0172918 A1 | 7/2012 | Fifer et al. |
| 2012/0179181 A1 | 7/2012 | Straub et al. |
| 2012/0197277 A1 | 8/2012 | Stinis |
| 2012/0232655 A1 | 9/2012 | Lorrison et al. |
| 2012/0271105 A1 | 10/2012 | Nakamura et al. |
| 2012/0271231 A1 | 10/2012 | Agrawal |
| 2012/0277788 A1 | 11/2012 | Cattaneo |

(56) References Cited

U.S. PATENT DOCUMENTS

| | | |
|---|---|---|
| 2012/0310166 A1 | 12/2012 | Huff |
| 2013/0030460 A1 | 1/2013 | Marks et al. |
| 2013/0035628 A1 | 2/2013 | Garrison et al. |
| 2013/0046332 A1 | 2/2013 | Jones et al. |
| 2013/0066348 A1 | 3/2013 | Fiorella et al. |
| 2013/0092012 A1 | 4/2013 | Marchand et al. |
| 2013/0096571 A1 | 4/2013 | Massicotte et al. |
| 2013/0102996 A1 | 4/2013 | Strauss |
| 2013/0116708 A1 | 5/2013 | Ziniti et al. |
| 2013/0116721 A1 | 5/2013 | Takagi et al. |
| 2013/0123705 A1 | 5/2013 | Holm et al. |
| 2013/0126559 A1 | 5/2013 | Cowan et al. |
| 2013/0144326 A1 | 6/2013 | Brady et al. |
| 2013/0150793 A1 | 6/2013 | Beissel et al. |
| 2013/0165871 A1 | 6/2013 | Fiorella et al. |
| 2013/0184703 A1 | 7/2013 | Shireman et al. |
| 2013/0190701 A1 | 7/2013 | Kirn |
| 2013/0197454 A1 | 8/2013 | Shibata et al. |
| 2013/0197567 A1 | 8/2013 | Brady et al. |
| 2013/0204297 A1 | 8/2013 | Melsheimer et al. |
| 2013/0226196 A1 | 8/2013 | Smith |
| 2013/0270161 A1 | 10/2013 | Kumar et al. |
| 2013/0281788 A1 | 10/2013 | Garrison |
| 2013/0289608 A1 | 10/2013 | Tanaka et al. |
| 2013/0317589 A1 | 11/2013 | Martin et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0025048 A1 | 1/2014 | Ward |
| 2014/0031856 A1 | 1/2014 | Martin |
| 2014/0046133 A1 | 2/2014 | Nakamura et al. |
| 2014/0046243 A1 | 2/2014 | Ray et al. |
| 2014/0052161 A1 | 2/2014 | Cully et al. |
| 2014/0074144 A1 | 3/2014 | Shrivastava et al. |
| 2014/0121672 A1 | 5/2014 | Folk |
| 2014/0155830 A1 | 6/2014 | Bonnette et al. |
| 2014/0155980 A1 | 6/2014 | Turjman |
| 2014/0163615 A1 | 6/2014 | Gadlage et al. |
| 2014/0180055 A1 | 6/2014 | Glynn et al. |
| 2014/0180397 A1 | 6/2014 | Gerberding et al. |
| 2014/0155908 A1 | 7/2014 | Rosenbluth et al. |
| 2014/0188127 A1 | 7/2014 | Dubrul et al. |
| 2014/0188143 A1 | 7/2014 | Martin et al. |
| 2014/0222070 A1 | 8/2014 | Belson et al. |
| 2014/0236219 A1 | 8/2014 | Dubrul et al. |
| 2014/0243882 A1 | 8/2014 | Ma |
| 2014/0257253 A1 | 9/2014 | Jemison |
| 2014/0257363 A1 | 9/2014 | Lippert |
| 2014/0276403 A1 | 9/2014 | Follmer et al. |
| 2014/0276592 A1 | 9/2014 | Mottola et al. |
| 2014/0296868 A1 | 10/2014 | Garrison et al. |
| 2014/0303658 A1 | 10/2014 | Bonnette et al. |
| 2014/0318354 A1 | 10/2014 | Thompson et al. |
| 2014/0324091 A1 | 10/2014 | Rosenbluth |
| 2014/0330286 A1 | 11/2014 | Wallace et al. |
| 2014/0336691 A1 | 11/2014 | Jones et al. |
| 2014/0343593 A1 | 11/2014 | Chin et al. |
| 2014/0364896 A1 | 12/2014 | Consigny |
| 2014/0371779 A1 | 12/2014 | Vale et al. |
| 2015/0005781 A1 | 1/2015 | Lund-Clausen et al. |
| 2015/0005792 A1 | 1/2015 | Ahn |
| 2015/0018859 A1 | 1/2015 | Quick |
| 2015/0018860 A1 | 1/2015 | Quick |
| 2015/0018929 A1 | 1/2015 | Martin et al. |
| 2015/0025555 A1 | 1/2015 | Sos |
| 2015/0032144 A1 | 1/2015 | Holloway |
| 2015/0059908 A1 | 3/2015 | Mollen |
| 2015/0088190 A1 | 3/2015 | Jensen |
| 2015/0119862 A1 | 4/2015 | Cajamarca et al. |
| 2015/0127035 A1 | 5/2015 | Trapp et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0164666 A1 | 6/2015 | Johnson et al. |
| 2015/0173782 A1 | 6/2015 | Garrison et al. |
| 2015/0190155 A1 | 7/2015 | Ulm, III |
| 2015/0190156 A1 | 7/2015 | Ulm, III |
| 2015/0196380 A1 | 7/2015 | Berrada et al. |
| 2015/0196744 A1 | 7/2015 | Aboytes |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0283309 A1 | 10/2015 | Look et al. |
| 2015/0305756 A1 | 10/2015 | Rosenbluth |
| 2015/0305859 A1 | 10/2015 | Eller |
| 2015/0314050 A1 | 11/2015 | Beer |
| 2015/0327875 A1 | 11/2015 | Look et al. |
| 2015/0352325 A1 | 12/2015 | Quick |
| 2015/0360001 A1 | 12/2015 | Quick |
| 2015/0366690 A1 | 12/2015 | Lumauig |
| 2015/0374391 A1 | 12/2015 | Quick |
| 2016/0022293 A1 | 1/2016 | Dubrul et al. |
| 2016/0030708 A1 | 2/2016 | Casiello et al. |
| 2016/0038267 A1 | 2/2016 | Allen et al. |
| 2016/0058540 A1 | 3/2016 | Don Michael |
| 2016/0074627 A1 | 3/2016 | Cottone |
| 2016/0106353 A1 | 4/2016 | Schuetz et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0113666 A1 | 4/2016 | Quick |
| 2016/0128857 A1 | 5/2016 | Kao |
| 2016/0135829 A1 | 5/2016 | Holochwost et al. |
| 2016/0143721 A1 | 5/2016 | Rosenbluth |
| 2016/0151605 A1 | 6/2016 | Welch et al. |
| 2016/0192912 A1 | 7/2016 | Kassab et al. |
| 2016/0206344 A1 | 7/2016 | Bruzzi et al. |
| 2016/0008014 A1 | 8/2016 | Rosenbluth |
| 2016/0220741 A1 | 8/2016 | Garrison et al. |
| 2016/0220795 A1 | 8/2016 | Korkuch et al. |
| 2016/0228134 A1 | 8/2016 | Martin et al. |
| 2016/0262774 A1 | 9/2016 | Honda |
| 2016/0262790 A1 | 9/2016 | Rosenbluth et al. |
| 2016/0287276 A1 | 10/2016 | Cox et al. |
| 2016/0367285 A1 | 12/2016 | Sos |
| 2017/0014560 A1 | 1/2017 | Minskoff et al. |
| 2017/0021130 A1 | 1/2017 | Dye |
| 2017/0037548 A1 | 2/2017 | Lee |
| 2017/0042571 A1 | 2/2017 | Levi |
| 2017/0049942 A1 | 2/2017 | Conlan et al. |
| 2017/0056032 A1 | 3/2017 | Look et al. |
| 2017/0058623 A1 | 3/2017 | Jaffrey et al. |
| 2017/0079672 A1 | 3/2017 | Quick |
| 2017/0086864 A1 | 3/2017 | Greenhalgh et al. |
| 2017/0100142 A1 | 4/2017 | Look et al. |
| 2017/0105743 A1 | 4/2017 | Vale et al. |
| 2017/0105745 A1 | 4/2017 | Rosenbluth et al. |
| 2017/0112514 A1 | 4/2017 | Marchand et al. |
| 2017/0113005 A1 | 4/2017 | Linder et al. |
| 2017/0143359 A1 | 5/2017 | Nguyen et al. |
| 2017/0143880 A1 | 5/2017 | Luxon et al. |
| 2017/0143938 A1 | 5/2017 | Ogle et al. |
| 2017/0165468 A1 | 6/2017 | Nobles et al. |
| 2017/0172591 A1 | 6/2017 | Ulm, III |
| 2017/0112513 A1 | 7/2017 | Marchand et al. |
| 2017/0189041 A1 | 7/2017 | Cox et al. |
| 2017/0196576 A1 | 7/2017 | Long et al. |
| 2017/0233908 A1 | 8/2017 | Kroczynski et al. |
| 2017/0238951 A1 | 8/2017 | Yang et al. |
| 2017/0252057 A1 | 9/2017 | Bonnette et al. |
| 2017/0265878 A1 | 9/2017 | Marchand et al. |
| 2017/0281204 A1 | 10/2017 | Garrison et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0319221 A1 | 11/2017 | Chu |
| 2017/0325839 A1 | 11/2017 | Rosenbluth et al. |

(56) References Cited

U.S. PATENT DOCUMENTS

| | | |
|---|---|---|
| 2017/0340867 A1 | 11/2017 | Accisano, II |
| 2017/0348014 A1 | 12/2017 | Wallace et al. |
| 2018/0014840 A1 | 1/2018 | Panian |
| 2018/0042623 A1 | 2/2018 | Batiste |
| 2018/0042624 A1 | 2/2018 | Greenhalgh et al. |
| 2018/0042626 A1 | 2/2018 | Greenhalgh et al. |
| 2018/0055999 A1 | 3/2018 | Bare et al. |
| 2018/0064453 A1 | 3/2018 | Garrison et al. |
| 2018/0064454 A1 | 3/2018 | Losordo et al. |
| 2018/0070968 A1 | 3/2018 | Wallace et al. |
| 2018/0078707 A1 | 3/2018 | Loonan |
| 2018/0092652 A1 | 4/2018 | Marchand et al. |
| 2018/0104404 A1 | 4/2018 | Ngo-Chu |
| 2018/0105963 A1 | 4/2018 | Quick |
| 2018/0125512 A1 | 5/2018 | Nguyen et al. |
| 2018/0184912 A1 | 7/2018 | Al-Ali |
| 2018/0193043 A1 | 7/2018 | Marchand et al. |
| 2018/0235742 A1 | 8/2018 | Fields et al. |
| 2018/0236205 A1 | 8/2018 | Krautkremer et al. |
| 2018/0250498 A1 | 9/2018 | Stern et al. |
| 2018/0256177 A1 | 9/2018 | Cooper et al. |
| 2018/0256178 A1 | 9/2018 | Cox et al. |
| 2018/0280623 A1 | 10/2018 | Pilkington et al. |
| 2018/0296240 A1 | 10/2018 | Rosenbluth et al. |
| 2018/0338770 A1 | 11/2018 | Mogi et al. |
| 2018/0339130 A1 | 11/2018 | Ogle |
| 2018/0344339 A1 | 12/2018 | Cox et al. |
| 2018/0353195 A1 | 12/2018 | Sigmon, Jr. et al. |
| 2018/0361116 A1 | 12/2018 | Quick et al. |
| 2019/0000492 A1 | 1/2019 | Casey et al. |
| 2019/0015298 A1 | 1/2019 | Beatty et al. |
| 2019/0046219 A1 | 2/2019 | Marchand et al. |
| 2019/0070401 A1 | 3/2019 | Merritt et al. |
| 2019/0117244 A1 | 4/2019 | Wallace et al. |
| 2019/0133622 A1 | 5/2019 | Wallace et al. |
| 2019/0133623 A1 | 5/2019 | Wallace et al. |
| 2019/0133624 A1 | 5/2019 | Wallace et al. |
| 2019/0133625 A1 | 5/2019 | Wallace et al. |
| 2019/0133626 A1 | 5/2019 | Wallace et al. |
| 2019/0133627 A1 | 5/2019 | Wallace et al. |
| 2019/0150959 A1 | 5/2019 | Cox et al. |
| 2019/0216476 A1 | 7/2019 | Barry et al. |
| 2019/0223893 A1 | 7/2019 | Gilvarry et al. |
| 2019/0231373 A1 | 8/2019 | Quick |
| 2019/0239910 A1 | 8/2019 | Brady et al. |
| 2019/0321071 A1 | 10/2019 | Marchand et al. |
| 2019/0328411 A1 | 10/2019 | Vale et al. |
| 2019/0336142 A1 | 11/2019 | Torrie et al. |
| 2019/0336148 A1 | 11/2019 | Greenhalgh et al. |
| 2019/0365395 A1 | 12/2019 | Tran et al. |
| 2019/0366036 A1 | 12/2019 | Jalgaonkar et al. |
| 2019/0366049 A1 | 12/2019 | Hannon et al. |
| 2019/0374239 A1 | 12/2019 | Martin et al. |
| 2020/0009301 A1 | 1/2020 | Yee |
| 2020/0022711 A1 | 1/2020 | Look et al. |
| 2020/0030579 A1 | 1/2020 | Taber |
| 2020/0046368 A1 | 2/2020 | Merritt et al. |
| 2020/0046940 A1 | 2/2020 | Carrison et al. |
| 2020/0054861 A1 | 2/2020 | Korkuch et al. |
| 2020/0069889 A1 | 3/2020 | Lin |
| 2020/0078029 A1 | 3/2020 | Hansen et al. |
| 2020/0113412 A1 | 4/2020 | Jensen |
| 2020/0121334 A1 | 4/2020 | Galdonik et al. |
| 2020/0129741 A1 | 4/2020 | Kawwas et al. |
| 2020/0324079 A1 | 10/2020 | Jalgaonkar et al. |
| 2021/0022843 A1 | 1/2021 | Hauser |
| 2021/0038385 A1 | 2/2021 | Popp et al. |
| 2021/0113224 A1 | 4/2021 | Dinh |
| 2021/0128182 A1 | 5/2021 | Teigen et al. |
| 2021/0128184 A1 | 5/2021 | Fulkerson et al. |
| 2021/0128185 A1 | 5/2021 | Nguyen et al. |
| 2021/0137667 A1 | 5/2021 | Sonnette et al. |
| 2021/0138194 A1 | 5/2021 | Carrison et al. |
| 2021/0154433 A1 | 5/2021 | Casey et al. |
| 2021/0186537 A1 | 6/2021 | Buck et al. |
| 2021/0186541 A1 | 6/2021 | Thress |
| 2021/0205577 A1 | 7/2021 | Jalgaonkar et al. |
| 2021/0236148 A1 | 8/2021 | Marchand et al. |
| 2021/0290925 A1 | 9/2021 | Merritt et al. |
| 2021/0315598 A1 | 10/2021 | Buck et al. |
| 2021/0316127 A1 | 10/2021 | Buck et al. |
| 2021/0330344 A1 | 10/2021 | Rosenbluth et al. |
| 2021/0378692 A1 | 12/2021 | Xiang et al. |
| 2021/0378694 A1 | 12/2021 | Thress et al. |
| 2021/0393278 A1 | 12/2021 | O'Malley et al. |
| 2021/0404464 A1 | 12/2021 | Patoskie |
| 2022/0000505 A1 | 1/2022 | Hauser |
| 2022/0000506 A1 | 1/2022 | Hauser |
| 2022/0000507 A1 | 1/2022 | Hauser |
| 2022/0015798 A1 | 1/2022 | Marchand et al. |
| 2022/0021197 A1 | 1/2022 | Zhao et al. |
| 2022/0022898 A1 | 1/2022 | Cox et al. |
| 2022/0033888 A1 | 2/2022 | Schnall-Levin et al. |
| 2022/0039815 A1 | 2/2022 | Thress et al. |
| 2022/0047281 A1 | 2/2022 | Kamalova |
| 2022/0125451 A1 | 4/2022 | Hauser |
| 2022/0142638 A1 | 5/2022 | Enright et al. |
| 2022/0151647 A1 | 5/2022 | Dolendo et al. |
| 2022/0160381 A1 | 5/2022 | Hauser |
| 2022/0160382 A1 | 5/2022 | Hauser |
| 2022/0160383 A1 | 5/2022 | Hauser |
| 2022/0226555 A1 | 6/2022 | Sunenshine et al. |
| 2022/0211400 A1 | 7/2022 | Cox et al. |
| 2022/0211992 A1 | 7/2022 | Merritt et al. |
| 2022/0240959 A1 | 8/2022 | Quick |
| 2022/0296797 A1 | 9/2022 | Chawla |
| 2022/0331554 A1 | 10/2022 | Beasley et al. |
| 2022/0346800 A1 | 11/2022 | Merritt et al. |
| 2022/0346801 A1 | 11/2022 | Merritt et al. |
| 2022/0346813 A1 | 11/2022 | Quick |
| 2022/0346814 A1 | 11/2022 | Quick |
| 2022/0347455 A1 | 11/2022 | Merritt et al. |
| 2022/0362512 A1 | 11/2022 | Quick et al. |
| 2022/0370761 A1 | 11/2022 | Chou et al. |
| 2022/0378445 A1 | 12/2022 | Culbert et al. |
| 2022/0378446 A1 | 12/2022 | Culbert et al. |
| 2022/0378447 A1 | 12/2022 | Culbert et al. |
| 2022/0378448 A1 | 12/2022 | Culbert et al. |
| 2022/0378451 A1 | 12/2022 | Goyal et al. |
| 2022/0378460 A1 | 12/2022 | Culbert et al. |
| 2022/0387072 A1 | 12/2022 | Look et al. |
| 2023/0015259 A1 | 1/2023 | Buck et al. |
| 2023/0047682 A1 | 2/2023 | Deaton et al. |
| 2023/0052964 A1 | 2/2023 | Singh et al. |
| 2023/0059721 A1 | 2/2023 | Chou et al. |
| 2023/0062809 A1 | 3/2023 | Merritt et al. |
| 2023/0063701 A1 | 3/2023 | Horowitz et al. |
| 2023/0070120 A1 | 3/2023 | Cox et al. |
| 2023/0122587 A1 | 4/2023 | Chou et al. |
| 2023/0149034 A1 | 5/2023 | Aklog et al. |
| 2023/0181200 A1 | 6/2023 | Deville et al. |
| 2023/0200970 A1 | 6/2023 | Merritt et al. |
| 2023/0210554 A1 | 7/2023 | Bruzzi et al. |
| 2023/0218313 A1 | 7/2023 | Rosenbluth et al. |
| 2023/0218383 A1 | 7/2023 | Merritt et al. |
| 2023/0233311 A1 | 7/2023 | Merritt et al. |
| 2023/0240705 A1 | 8/2023 | Rosenbluth et al. |
| 2023/0240706 A1 | 8/2023 | Rosenbluth et al. |
| 2023/0241302 A1 | 8/2023 | Merritt et al. |
| 2023/0248380 A1 | 8/2023 | Long et al. |
| 2023/0248498 A1 | 8/2023 | Buck et al. |
| 2023/0248499 A1 | 8/2023 | Buck et al. |
| 2023/0248500 A1 | 8/2023 | Buck et al. |
| 2023/0248501 A1 | 8/2023 | Buck et al. |
| 2023/0248502 A1 | 8/2023 | Buck et al. |
| 2023/0248503 A1 | 8/2023 | Buck et al. |
| 2023/0248504 A1 | 8/2023 | Buck et al. |
| 2023/0270991 A1 | 8/2023 | Merritt et al. |
| 2023/0310137 A1 | 10/2023 | Merritt et al. |
| 2023/0310138 A1 | 10/2023 | Merritt et al. |
| 2023/0310751 A1 | 10/2023 | Merritt et al. |
| 2023/0320834 A1 | 10/2023 | Merritt et al. |
| 2023/0329734 A1 | 10/2023 | Marchand et al. |
| 2023/0338130 A1 | 10/2023 | Merritt et al. |

(56) References Cited

U.S. PATENT DOCUMENTS

| | | | |
|---|---|---|---|
| 2023/0338131 A1 | 10/2023 | Merritt et al. |
| 2023/0355256 A1 | 11/2023 | Dinh |
| 2023/0355259 A1 | 11/2023 | Marchand et al. |
| 2023/0355371 A1 | 11/2023 | Buck et al. |
| 2023/0355938 A1 | 11/2023 | Merritt et al. |
| 2023/0363776 A1 | 11/2023 | Quick |
| 2023/0363883 A1 | 11/2023 | Merritt et al. |
| 2023/0389932 A1 | 12/2023 | Ozenne et al. |
| 2023/0390045 A1 | 12/2023 | Merritt et al. |
| 2024/0016505 A1 | 1/2024 | Horowitz et al. |
| 2024/0016993 A1 | 1/2024 | Haslam et al. |
| 2024/0058113 A1 | 2/2024 | Strauss et al. |
| 2024/0074771 A1 | 3/2024 | Quick et al. |
| 2024/0082540 A1 | 3/2024 | Brodt et al. |
| 2024/0108366 A1 | 4/2024 | Horowitz et al. |
| 2024/0131235 A1 | 4/2024 | Horowitz et al. |
| 2024/0157041 A1 | 5/2024 | Zikry et al. |
| 2024/0173042 A1 | 5/2024 | Yang et al. |
| 2024/0198072 A1 | 6/2024 | Merritt et al. |
| 2024/0207593 A1 | 6/2024 | Merritt et al. |
| 2024/0225674 A1 | 7/2024 | Dederich et al. |
| 2024/0245501 A1 | 7/2024 | Strauss et al. |
| 2024/0245502 A1 | 7/2024 | Merritt et al. |
| 2024/0261492 A1 | 8/2024 | Yang et al. |
| 2024/0285387 A1 | 8/2024 | Merritt et al. |
| 2024/0299053 A1 | 9/2024 | Hauser |
| 2024/0307082 A1 | 9/2024 | Marchand et al. |
| 2024/0307166 A1 | 9/2024 | Merritt et al. |
| 2024/0341779 A1 | 10/2024 | Dinh |
| 2024/0341788 A1 | 10/2024 | Cox et al. |
| 2024/0407905 A1 | 12/2024 | Merrit et al. |
| 2024/0415626 A1 | 12/2024 | Merrit et al. |
| 2024/0415627 A1 | 12/2024 | Merrit et al. |
| 2025/0017618 A1 | 1/2025 | Truty et al. |
| 2025/0049456 A1 | 2/2025 | Cox et al. |
| 2025/0064464 A1 | 2/2025 | Barkley et al. |

FOREIGN PATENT DOCUMENTS

| | | |
|---|---|---|
| CN | 102014772 | 4/2011 |
| CN | 102186427 | 9/2011 |
| CN | 102316809 | 1/2012 |
| CN | 103764049 | 4/2014 |
| CN | 103932756 | 7/2014 |
| CN | 104068910 | 10/2014 |
| CN | 106178227 | 12/2016 |
| CN | 106470728 | 3/2017 |
| CN | 108348319 | 7/2018 |
| CN | 110312481 | 10/2019 |
| CN | 110652645 | 1/2020 |
| CN | 111281482 | 6/2020 |
| CN | 215082793 | 12/2021 |
| DE | 1116001 | 10/1961 |
| DE | 102017004383 | 7/2018 |
| EP | 0914807 | 5/1999 |
| EP | 1254634 | 11/2002 |
| EP | 1991138 | 11/2008 |
| EP | 2073864 | 7/2009 |
| EP | 2203209 | 7/2010 |
| EP | 2209509 | 7/2010 |
| EP | 2394680 | 12/2011 |
| EP | 1867290 | 2/2013 |
| EP | 2624905 | 8/2013 |
| EP | 2540328 | 10/2013 |
| EP | 2726135 | 5/2014 |
| EP | 2908783 | 8/2015 |
| EP | 2939704 | 11/2015 |
| EP | 2942624 | 11/2015 |
| EP | 2967614 | 1/2016 |
| EP | 2977072 | 1/2016 |
| EP | 2367482 | 10/2016 |
| EP | 3102274 | 12/2016 |
| EP | 3122412 | 2/2017 |
| EP | 3202340 | 8/2017 |
| EP | 3302624 | 4/2018 |
| EP | 3305220 | 4/2018 |
| EP | 3305221 | 4/2018 |
| EP | 3311875 | 4/2018 |
| EP | 2231256 | 5/2018 |
| EP | 3344157 | 7/2018 |
| EP | 3417893 | 12/2018 |
| EP | 3419528 | 1/2019 |
| EP | 3422963 | 1/2019 |
| EP | 3439561 | 2/2019 |
| EP | 3449967 | 3/2019 |
| EP | 3544528 | 10/2019 |
| EP | 3583972 | 12/2019 |
| EP | 3589348 | 1/2020 |
| EP | 3603690 | 2/2020 |
| EP | 3612264 | 2/2020 |
| EP | 3620204 | 3/2020 |
| EP | 3013404 | 4/2020 |
| EP | 4039205 | 8/2022 |
| EP | 4072613 | 10/2022 |
| EP | 4076611 | 10/2022 |
| EP | 4079344 | 10/2022 |
| EP | 4137070 | 2/2023 |
| EP | 4144310 | 3/2023 |
| EP | 4252992 | 10/2023 |
| EP | 4419159 | 8/2024 |
| GB | 1588072 | 4/1981 |
| GB | 2498349 | 7/2013 |
| JP | H6190049 | 7/1994 |
| JP | H07323090 A | 12/1995 |
| JP | 2001522631 | 5/1999 |
| JP | 2000175925 | 6/2000 |
| JP | 2004097807 | 4/2004 |
| JP | 2005511989 | 4/2005 |
| JP | 2005-095242 | 6/2005 |
| JP | 2005230132 | 9/2005 |
| JP | 2005323702 | 11/2005 |
| JP | 2006094876 | 4/2006 |
| JP | 2007-222658 | 9/2007 |
| JP | 2011526820 | 1/2010 |
| JP | 2011517424 | 6/2011 |
| JP | 05694718 | 4/2015 |
| JP | 2015208685 | 11/2015 |
| JP | 2016513505 | 5/2016 |
| JP | 2016104212 | 6/2016 |
| JP | 2017533051 | 11/2017 |
| JP | 2018525088 | 9/2018 |
| JP | 2003033359 | 2/2023 |
| JP | 7253376 | 3/2023 |
| JP | 7324264 | 8/2023 |
| JP | 7491974 | 5/2024 |
| WO | WO1997017889 | 5/1997 |
| WO | WO199833443 | 8/1998 |
| WO | WO199838920 | 9/1998 |
| WO | WO199839053 | 9/1998 |
| WO | WO199851237 | 11/1998 |
| WO | WO1999044542 | 9/1999 |
| WO | WO9951140 | 10/1999 |
| WO | WO2000032118 | 6/2000 |
| WO | WO2000053120 | 9/2000 |
| WO | WO0202162 | 1/2002 |
| WO | WO2002055146 | 7/2002 |
| WO | WO2003015840 | 2/2003 |
| WO | WO2004018916 | 3/2004 |
| WO | WO2004093696 | 11/2004 |
| WO | WO2005046736 | 5/2005 |
| WO | WO2006029270 | 3/2006 |
| WO | WO2006110186 | 10/2006 |
| WO | WO2006124307 | 11/2006 |
| WO | WO2007092820 | 8/2007 |
| WO | WO2009082513 | 7/2009 |
| WO | WO2009086482 | 7/2009 |
| WO | WO2009105710 | 8/2009 |
| WO | WO2009126747 | 10/2009 |
| WO | WO2009155571 | 12/2009 |
| WO | WO2010002549 | 1/2010 |
| WO | WO2010010545 | 1/2010 |
| WO | WO2010023671 | 3/2010 |
| WO | WO2010049121 | 5/2010 |
| WO | WO2010095712 | 8/2010 |

(56) References Cited

FOREIGN PATENT DOCUMENTS

| | | |
|---|---|---|
| WO | WO2010102307 | 9/2010 |
| WO | WO2011032712 | 3/2011 |
| WO | WO2011054531 | 5/2011 |
| WO | WO2011073176 | 6/2011 |
| WO | WO2012009675 | 1/2012 |
| WO | WO2012011097 | 1/2012 |
| WO | WO2012049652 | 4/2012 |
| WO | WO2012065748 | 5/2012 |
| WO | WO2012114633 | 8/2012 |
| WO | WO2012120490 | 9/2012 |
| WO | WO2012162437 | 11/2012 |
| WO | WO2014047650 | 3/2014 |
| WO | WO2014081892 | 5/2014 |
| WO | WO2014139845 | 9/2014 |
| WO | WO2015006782 | 1/2015 |
| WO | WO2015061365 | 4/2015 |
| WO | WO2015121424 | 8/2015 |
| WO | WO2015179329 | 11/2015 |
| WO | WO2015189354 | 12/2015 |
| WO | WO2015191646 | 12/2015 |
| WO | WO2016014955 | 1/2016 |
| WO | WO2016071524 | 5/2016 |
| WO | WO2017024258 | 2/2017 |
| WO | WO2017033182 | 3/2017 |
| WO | WO2017058280 | 4/2017 |
| WO | WO2017070702 | 4/2017 |
| WO | WO2017106877 | 6/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO2018049317 | 3/2018 |
| WO | WO2018065092 | 4/2018 |
| WO | WO2018080590 | 5/2018 |
| WO | WO2018148174 | 8/2018 |
| WO | WO2019010318 | 1/2019 |
| WO | WO2019050765 | 3/2019 |
| WO | WO2019064306 | 4/2019 |
| WO | WO2019075444 | 4/2019 |
| WO | WO2019094456 | 5/2019 |
| WO | WO2019173475 | 9/2019 |
| WO | WO2019222117 | 11/2019 |
| WO | WO2019246240 | 12/2019 |
| WO | WO2020036809 | 2/2020 |
| WO | WO2020142381 | 7/2020 |
| WO | WO2021067134 | 4/2021 |
| WO | WO2021076954 | 4/2021 |
| WO | WO2021127202 | 6/2021 |
| WO | WO2021248042 | 12/2021 |
| WO | WO2022032173 | 2/2022 |
| WO | WO2022103848 | 5/2022 |
| WO | WO2022109021 | 5/2022 |
| WO | WO2022109034 | 5/2022 |
| WO | WO2022261448 | 12/2022 |
| WO | WO2023018819 | 2/2023 |
| WO | WO2023069874 | 4/2023 |
| WO | WO2003048616 | 6/2023 |
| WO | WO2023115032 | 6/2023 |
| WO | WO2023137341 | 7/2023 |
| WO | WO2023147353 | 8/2023 |
| WO | WO2023154612 | 8/2023 |
| WO | WO2023192925 | 10/2023 |
| WO | WO2023215779 | 11/2023 |
| WO | WO2023239706 | 12/2023 |
| WO | WO2024054988 | 3/2024 |
| WO | WO2024103036 | 5/2024 |
| WO | WO2024151629 | 7/2024 |
| WO | WO2025014517 | 1/2025 |

OTHER PUBLICATIONS

US 12,115,056 B2, 10/2024, Merritt et al. (withdrawn)
Gibbs, et al., "Temporary Stent as a bail-out device during percutaneous transluminal coronary angioplasty: preliminary clinical experience," British Heart Journal, 1994, 71:372-377, Oct. 12, 1993, 6 pgs.
Gupta, S. et al., "Acute Pulmonary Embolism Advances in Treatment", JAPI, Association of Physicians India, Mar. 2008, vol. 56, 185-191.
International Search Report and Written Opinion for International App. No. PCT/US13/61470, malled Jan. 17, 2014, 7 pages.
International Search Report and Written Opinion for International App. No. PCT/US2014/046567, mailed Nov. 3, 2014, 13 pages.
International Search Report and Written Opinion for International App. No. PCT/US2014/061645, mailed Jan. 23, 2015, 15 pages.
International Search Report for International App. No. PCT/US13/71101, mailed Mar. 31, 2014, 4 pages.
Konstantinides, S. et al., "Pulmonary embolism hotline 2012—Recent and expected trials", Thrombosis and Haemostasis, Jan. 9, 2013:33; 43-50.
Konstantinides, S. et al., "Pulmonary embolism: risk assessment and management", European Society of Cardiology; European Heart Journal, Sep. 7, 2012:33, 3014-3022.
Kucher, N. et al., "Percutaneous Catheter Thrombectomy Device for Acute Pulmonary Embolism: In Vitro and in Vivo Testing", Circulation, Sep. 2005:112:e28-e32.
Kucher, N., "Catheter Interventions in Massive Pulmonary Embolism", Cardiology Rounds, Mar. 2006 vol. 10, Issue 3, 6 pages.
Kucher, N. et al., "Management of Massive Pulmonary Embolism", Radiology, Sep. 2005:236:3852-858.
Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.
Kuo. W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.
Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.
Kuo, W. MD, "Endovascular Therapy for Acute Pulmonary Embolism", Continuing Medical Education Society of Interventional Radiology ("CME"); Journal of Vascular and Interventional Radiology, Feb. 2012: 23:167-179.
Lee, L. et al., "Massive pulmonary embolism: review of management strategies with a focus on catheter-based techniques", Expert Rev. Cardiovasc. Ther. 8(6), 863-873 (2010).
Liu, S. et al., "Massive Pulmonary Embolism: Treatment with the Rotarex Thrombectomy System", Cardiovascular Interventional Radiology; 2011: 34:106-113.
Muller-Hulsbeck, S. et al. "Mechanical Thrombectomy of Major and Massive Pulmonary Embolism with Use of the Amplatz Thrombectomy Device", Investigative Radiology, Jun. 2001:36:6:317-322.
Reekers, J. et al., "Mechanical Thrombectomy for Early Treatment of Massive Pulmonary Embolism", CardioVascular and Interventional Radiology, 2003: 26:246-250.
Schmitz-Rode et al., "New Mesh Basket for Percutaneous Removal of Wall-Adherent Thrombi in Dialysis Shunts," Cardiovasc Intervent Radiol 16:7-10 1993 4 pgs.
Schmitz-Rode et al., "Temporary Pulmonary Stent Placement as Emergency Treatment of Pulmonary Embolism," Journal of the American College of Cardiology, vol. 48, No. 4, 2006 (5 pgs.).
Schmitz-Rode, T. et al., "Massive Pulmonary Embolism: Percutaneous Emergency Treatment by Pigtail Rotation Catheter", JACC Journal of the American College of Cardiology, Aug. 2000:36:2:375-380.
Spiotta, A et al., "Evolution of thrombectomy approaches and devices for acute stroke: a technical review." J NeuroIntervent Surg 2015, 7, pp. 7 pages.
Svilaas, T. et al., "Thrombus Aspiration During Primary Percutaneous Coronary Intervention." The New England Journal of Medicine, 2008, vol. 358, No. 6, 11 pages.
Tapson, V., "Acute Pulmonary Embolism", The New England Journal of Medicine, Mar. 6, 2008:358:2037-52.

(56) References Cited

OTHER PUBLICATIONS

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.
Truong et al., "Mechanical Thrombectomy of Iliocaval Thrombosis Using a Protective Expandable Sheath," Cardiovasc Intervent Radiol27-254-258, 2004, 5 pgs.
Turk et al., "Adapt Fast study: a direct aspiration first pass technique for acute stroke thrombectomy." J Neurointervent Surg, vol. 6, 2014, 6 pages.
Uflacker, R., "Interventional Therapy for Pulmonary Embolism", Journal of Vascular and Interventional Radiology, Feb. 2001: 12:147-164.
Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.
International Search Report and Written Opinion for International App. No. PCT/US2015/034987 filed Jun. 9, 2015, Applicant: Inceptus Medical, LLC, Date of Mailing: Sep. 17, 2015, 12 pages.
International Search Report and Written Opinion for International App. No. PCT/US2016/067628 filed Dec. 19, 2016, Applicant: Inari Medical, Inc., Date of Mailing: Apr. 10, 2017, 11 pages.
Goldhaber, S. et al. "Percutaneous Mechanical Thrombectomy for Acute Pulmonary Embolism—A Double-Edged Sword," American College of CHEST Physicians, Aug. 2007, 132:2, 363-372.
Goldhaber, S., "Advanced treatment strategies for acute pulmonary embolism, including thrombolysis and embolectomy," Journal of Thrombosis and Haemostasis, 2009: 7 (Suppl. 1): 322-327.
International Search Report and Written Opinion for International App. No. PCT/US2017/029696, Date of Filing: Apr. 26, 2017, Applicant: Inari Medical, Inc., Date of Mailing: Sep. 15, 2017, 19 pages.
International Search Report and Written Opinion for International App. No. PCT/US2016/058536, Date of Filing: Oct. 24, 2016, Applicant: Inari Medical, Inc., Date of Mailing: Mar. 13, 2017, 14 pages.
International Search Report and Written Opinion for International App. No. PCT/US2018/048786, Date of Filing: Aug. 30, 2018, Applicant: Inari Medical, Inc., Date of Malling: Dec. 13, 2018, 12 pages,.
International Search Report and Written Opinion for International App. No. PCT/US2018/055780, Date of Filing: Oct. 13, 2018, Applicant: Inceptus Medical LLC., Date of Mailing: Jan. 22, 2019, 8 pages.
International Search Report and Written Opinion for International App. No. PCT/US2019/045794, Date of Filing: Aug. 8, 2019, Applicant: Inari Medical, Inc., Date of Mailing: Nov. 1, 2019, 17 pages.
International Search Report and Written Opinion for International App. No. PCT/US2020/056067, Date of Filing: Oct. 16, 2020; Applicant: Inari Medical, Inc., Date of Mailing: Jan. 22, 2021, 8 pages.
International Search Report and Written Opinion for International App. No. PCT/US2020/055645, Date of Filing: Dec. 17, 2020; Applicant: Inari Medical, Inc., Date of Mailing: Apr. 14, 2021, 12 pages.
Vorwerk, D. MD, et al., "Use of a Temporary Caval Filter to Assist Percutaneous Iliocaval Thrombectomy: Experimental Results." SCVIR, 1995, 4 pages.
Wikipedia; Embolectomy; retrieved from the internet: https://en.wikipedia.org/wiki/Embolectorny; 4 pgs.; retrieved/printed: Mar. 24, 2016.
O'sullivan; Thrombolysis versus thrombectomy in acute deep vein thrombosis; Interventional Cardiology; 3(5): pp. 589-596; Oct. 2011.
Capture Vascular Systems; (company website); retrieved from the internet: http://www.capturevascular.com; 3 pgs .; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 2 pgs.; retrieved/printed: Mar. 24, 2016.
Penumbra, Inc.; Indigo® System (product information); retrieved from the internet: http://www.penumbrainc.com/peripherallpercutaneous-thromboembolectorny/indigo-system; 7 pgs.; retrieved/printed: Mar. 24, 2016.
Youtube; Merci Retrieval System X Series Animation; uploaded Mar. 16, 2009 (product information); posted on May 7, 2009 by SSMDePAUL, time 1:09, retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm;© 2015; 2 pgs.; retrieved/printed: Mar. 24, 2016.
International Search Report and Written Opinion for International App. No. PCT/US21/35965, Date of Filing: Jun. 4, 2021, Applicant: Inari Medical, Inc., Date of Mailing: Sep. 28, 2021, 12 pages.
International Search Report and Written Opinion for International App. No. PCT/US21/45072 Date of Filing: Aug. 6, 2021, Applicant: Inari Medical, Inc., Date of Mailing: Jan. 20, 2022, 10 pages.
International Search Report and Written Opinion for International App. No. PCT/US21/58793; Date of Filing: Nov. 10, 2021, Applicant: Inari Medical, Inc., Date of Mailing: Mar. 16, 2022, 13 pages.
International Search Report and Written Opinion for International App. No. PCT/US21/59718; Date of Filing: Nov. 17, 2021, Applicant: Inari Medical, Inc., Date of Mailing: Mar. 22, 2022, 13 pages.
International Search Report and Written Opinion for International App. No. PCT/US21/59735; Date of Filing: Nov. 17, 2021, Applicant: Inari Medical, Inc., Date of Mailing: Mar. 22, 2022, 11 pages.
International Search Report and Written Opinion for International App. No. PCT/US2023/079428; Applicant: Inari Medical, Inc., Date of Mailing: May 29, 2024, 18 pages.
Extended European Search Report for European Application No. 21818772.2, Applicant: Inari Medical, Inc., Date of Mailing: May 10, 9 pages.
Chinese Office Action received for Application No. 202111061740.2, Applicant: Inari Medical, Inc, Date of Mailing: May 23, 2024, 15 pages.
English translation of Japanese Office Action mailed Jun. 25, 2024 for Japanese Application No. 2022-574456, 5 pages.
Japanese Office Action mailed Jul. 8, 2024 for Japanese Application No. 2022-522892, 14 pages.
Chinese first Office Action mailed May 10, 2024 for Chinese Application No. 202080087833.X, 11 pages.
Partial Supplementary European Search Report received for European Application No. 21852966.7; Applicant: Inari Medical, Inc., Date of Mailing: Jul. 23, 2024, 12 pages.
Japanese Office Action mailed Aug. 2, 2024 for Japanese Application No. 2023-213724, 3 pages.
English Translation of Japanese Office Action mailed Jul. 23, 2024 for Japanese Application No. 2022-535535, 11 pages.
Extended European Search Report received for European Application No. 21895504.5; Applicant: Inari Medical, Inc., Date of Mailing: Aug. 16, 2024, 10 pages.
English translation of Japanese Office Action mailed Sep. 17, 2024 for Japanese Application No. 2023-203650, 6 pages.
English machine translation of Japanese Office Action mailed Oct. 10, 2024 for Japanese Application No. 2022-522892, 11 pages.
Extended European Search Report issued for EP Application No. 20877370.5, Date of Mailing: Oct. 17, 2023, 11 pages.
International Search Report and Written Opinion for International App. No. PCT/US23/65128; Date of Filing: Mar. 30, 2023, Applicant: Inari Medical, Inc., Date of Mailing: Nov. 14, 2023, 14 pages.

(56) References Cited

OTHER PUBLICATIONS

International Search Report and Written Opinion for International App. No. PCT/US23/66538; Date of Filing: May 3, 2023, Applicant: Inari Medical, Inc., Date of Mailing: Jan. 4, 2024, 14 pages.

English translation of Japanese Office Action received for JP Application No. 2022-574456, Applicant: Inari Medical, Inc, Date of Mailing: Jan. 23, 2024, 12 pages.

Chinese First Office Action received for CN Application No. 201980067623.1, Applicant: Inari Medical, Inc., Date of Mailing: Jan. 31, 2024, 10 pages.

International Search Report and Written Opinion for International App. No. PCT/US23/73765; Date of Filing: Sep. 8, 2023, Applicant: Inari Medical, Inc., Date of Mailing: Feb. 28, 2024, 7 pages.

International Search Report and Written Opinion for International App. No. PCT/US23/69892; Date of Filing: Jul. 10, 2023, Applicant: Inari Medical, Inc., Date of Mailing: Feb. 29, 2024, 12 pages.

English translation of Japanese Office Action mailed Jan. 19, 2024 for Japanese Application No. 2022-160947, 8 pages.

International Search Report and Written Opinion for International App. No. PCT/US2024/010875; Applicant: Inari Medical, Inc., Date of Mailing: Apr. 26, 2024, 15 pages.

International Search Report and Written Opinion for International App. No. PCT/US23/60927; Date of Filing: Jan. 19, 2023, Applicant: Inari Medical, Inc., Date of Mailing: Jul. 20, 2023, 12 pages.

International Search Report and Written Opinion for International App. No. PCT/US23/60502; Date of Filing: Jan. 11, 2023, Applicant: Inari Medical, Inc., Date of Mailing: May 25, 2023, 9 pages.

International Search Report and Written Opinion for International App. No. PCT/US23/61256; Date of Filing: Jan. 25, 2023, Applicant: Inari Medical, Inc., Date of Mailing: Jun. 7, 2023, 8 pages.

Gross et al., "Dump the pump: manual aspiration thrombectomy (MAT) with a syringe is technically effective, expeditious, and cost-efficient," J NeuroIntervent Surg, 2018, 4 pages.

International Search Report and Written Opinion for International App. No. PCT/US2024/043504; Applicant: Inari Medical, Inc., Date of Mailing: Nov. 12, 2024, 12 pages.

International Search Report and Written Opinion for International App. No. PCT/US2024/037570; Applicant: Inari Medical, Inc., Date of Mailing: Nov. 20, 2024, 12 pages.

International Search Report and Written Opinion for International App. No. PCT/US2024/046723; Applicant: Inari Medical, Inc., Date of Mailing: Nov. 27, 2024, 11 pages.

English translation of Chinese Office Action mailed Jan. 22, 2025 for Chinese Application No. 202210842779.6, 17 pages.

Extended European Search Report received for European Application No. 24209030.6; Applicant: Inari Medical, Inc., Date of Mailing: Feb. 3, 2025, 7 pages.

\* cited by examiner

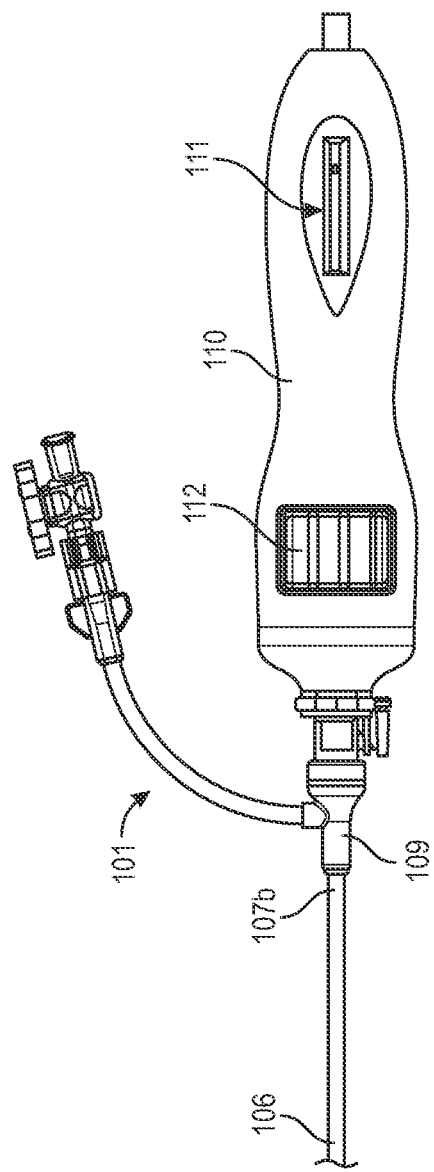
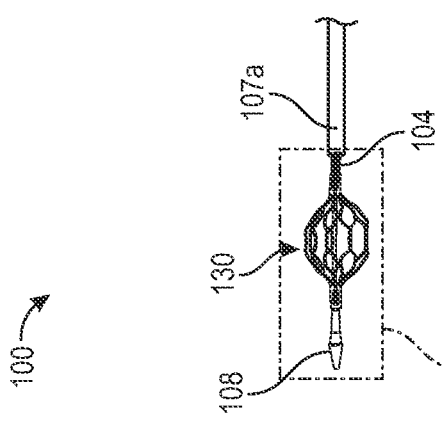
FIG. 1A
FIG. 1B

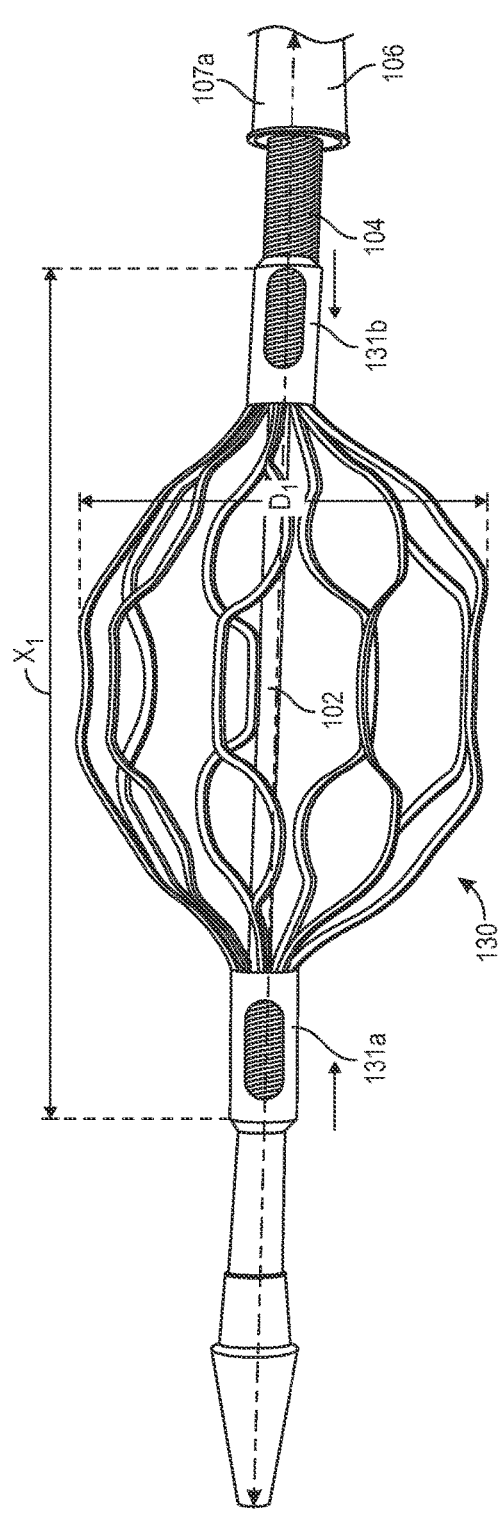
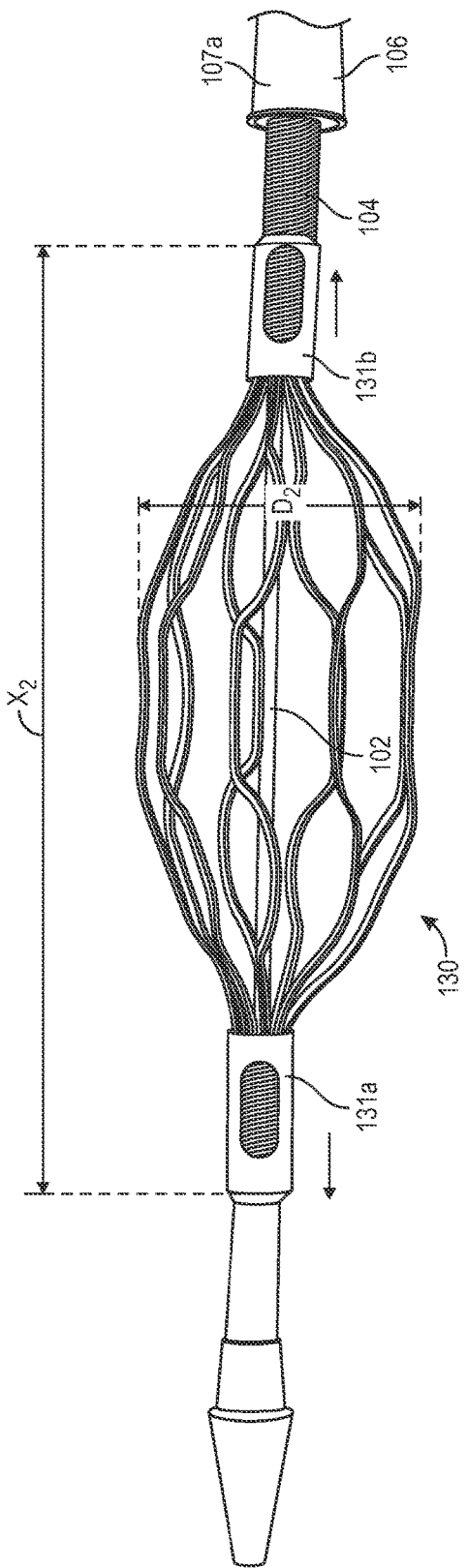
FIG. 6A
FIG. 6B

FIGS. 11B/11C

DEVICES FOR REMOVING CLOT MATERIAL FROM INTRAVASCULARLY IMPLANTED DEVICES, AND ASSOCIATED SYSTEMS AND METHODS

CROSS-REFERENCE TO RELATED APPLICATION

This application claims the benefit of U.S. Provisional Patent Application No. 63/298,399, filed Jan. 11, 2022, and titled "DEVICES FOR REMOVING CLOT MATERIAL FROM INTRAVASCULARLY IMPLANTED STENTS, AND ASSOCIATED SYSTEMS AND METHODS," which is incorporated herein by reference in its entirety.

TECHNICAL FIELD

The present technology generally relates to devices for cleaning stents, embolic protection devices, other implants, and/or bare vessels and, more particularly, for example, to devices for intravascularly removing clot and/or other material from stents implanted in the vasculature of a patient (e.g., the venous vasculature).

BACKGROUND

Stents are tubes or similar structures that can be implanted within a blood vessel of a patient to mechanically keep the vessel open, restore flow, and/or bypass a diseased region of the blood vessel. Stents are typically made of metal or plastic, and can be crimped or packed down into a delivery catheter before being intravascularly delivered to a target location within the blood vessel.

After a stent is delivered to and implanted within a blood vessel of a patient, unwanted material can form around and/or adhere to the stent. For example, clot material can form and adhere to an inner surface of the stent. Similarly, vascular wall cells can abnormally accumulate within the stent (e.g., intimal hyperplasia).

Physicians are currently limited in their abilities to remove adherent clot or intimal hyperplasia from implanted stents and, in particular, venous stents. For example, while aspiration mechanisms exist to remove clot material from venous stents, these aspiration mechanisms are limited to non-adherent, acute clot, and cannot treat chronic adherent clot or intimal hyperplasia. Further, while mechanical clot treatment devices exist to target adherent clot material, many such devices are currently contraindicated for removing clot material from stents because the mechanical clot treatment devices can catch on the stent, causing damage. Other methods of medical management such as ballooning or re-stenting do not remove the clot that has been formed, likely causing additional clot to form. Pharmacological methods—such as administering tissue plasminogen activator (tPA)—do not work on aged, more adherent clot, and also carry other risks such as systemic bleeding. Surgery carries risks of adverse events and is more invasive than transcatheter methods.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1A is a side view of a stent cleaning system in accordance with embodiments of the present technology.

FIGS. 6A and 6B are side views of a distal portion of the system of FIG. 1A including the clot treatment device in a first position and a second position, respectively, in accordance with embodiments of the present technology.

DETAILED DESCRIPTION

Figure 1B:
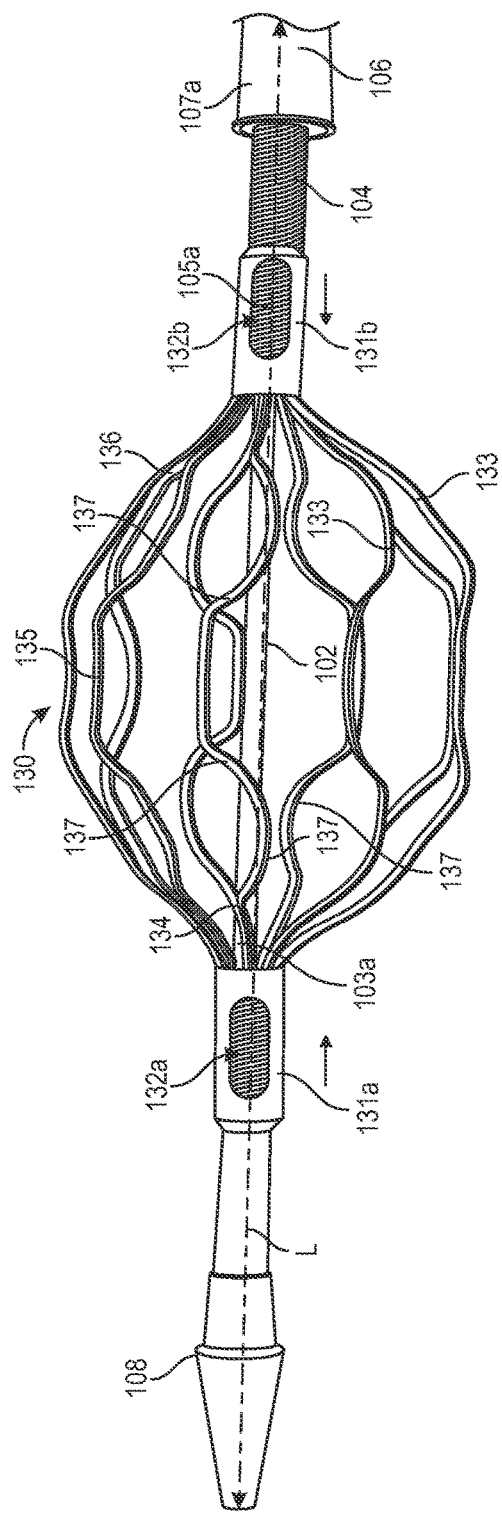
FIGS. 1B and 1C are an enlarged side view and an enlarged proximally-facing view, respectively, of a distal portion of the system of FIG. 1A including a clot treatment device in accordance with embodiments of the present technology.

The present technology is generally directed to devices for mechanically removing clot and/or other material from the vasculature of a patient, and associated systems and methods. In particular, some of the embodiments are directed to devices for mechanically removing clot and/or other material from implants implanted in the vasculature of the patient, such as stents implanted within the venous vasculature. In some embodiments described below, a system for removing clot material from an implant—such as a venous stent—includes a (i) clot treatment device, (ii) a handle, and (iii) a first elongate member and a second elongate member coupling the clot treatment device to the handle. The clot treatment device is configured to be deployed within the implant, and includes a first end portion, a second end portion, and a plurality of struts extending between the first and second end portions. The first elongate member couples the first end portion of the clot treatment device to the handle, and the second elongate member couples the second end portion of the clot treatment device to the handle (e.g., to an actuator of the handle). Actuation of the actuator in a first direction is configured to move the second elongate member relative to the first elongate member and/or the first elongate member relative to the second elongate member to move the first and second end portions toward one another to radially expand the struts. The actuator can be actuated in a second direction (e.g., opposite the first direction) to move the second elongate member relative to the first elongate member and/or the first elongate member relative to the second elongate member to move the first and second end portions away from one another to radially collapse the struts.

When expanded within the implant, the clot treatment device can be (i) translated proximally and/or distally through the implant by translating the handle and (ii) rotated within the implant by rotating the handle. Such movements can mechanically engage the clot treatment device with clot material adhered to the implant to dislodge the clot material. In some aspects of the present technology, the clot treatment device is configured to be translated and/or rotated within the implant without catching on the implant, avoiding potential damage, deformation, movement, and/or migration of the implant. For example, the struts can extend generally axially between the first and second end portions—and not include any cross-members connected therebetween that are configured to contact the implant—to reduce the likelihood of the struts damaging the implant.

Certain details are set forth in the following description and in FIGS. 1-28 to provide a thorough understanding of various embodiments of the present technology. In other instances, well-known structures, materials, operations, and/or systems often associated with intravascular procedures, stents, vascular implants, clot removal procedures, catheters, and the like are not shown or described in detail in the following disclosure to avoid unnecessarily obscuring the description of the various embodiments of the technology. Those of ordinary skill in the art will recognize, however, that the present technology can be practiced without one or more of the details set forth herein, and/or with other structures, methods, components, and so forth. Moreover, although many of the devices and systems are described herein in the context of removing and/or treating clot material (e.g., clot material adhered to an implant), the present technology can be used to remove and/or treat other unwanted material in addition or alternatively to clot material, such as thrombi, emboli, plaque, intimal hyperplasia, post-thrombotic scar tissue, etc. Accordingly, the terms "clot" and "clot material" as used herein can refer to any of the foregoing materials.

The terminology used below is to be interpreted in its broadest reasonable manner, even though it is being used in conjunction with a detailed description of certain examples of embodiments of the technology. Indeed, certain terms may even be emphasized below; however, any terminology intended to be interpreted in any restricted manner will be overtly and specifically defined as such in this Detailed Description section.

The accompanying Figures depict embodiments of the present technology and are not intended to be limiting of its scope unless expressly indicated. The sizes of various depicted elements are not necessarily drawn to scale, and these various elements may be enlarged to improve legibility. Component details may be abstracted in the Figures to exclude details such as position of components and certain precise connections between such components when such details are unnecessary for a complete understanding of how to make and use the present technology. Many of the details, dimensions, angles and other features shown in the Figures are merely illustrative of particular embodiments of the disclosure. Accordingly, other embodiments can have other details, dimensions, angles and features without departing from the present technology. In addition, those of ordinary skill in the art will appreciate that further embodiments of the present technology can be practiced without several of the details described below.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," and the like are not meant to limit the referenced component to a specific orientation. It will be appreciated that such designations refer to the orientation of the referenced component as illustrated in the Figures; the systems of the present technology can be used in any orientation suitable to the user. To the extent any materials incorporated herein by reference conflict with the present disclosure, the present disclosure controls.

Figure 1C:
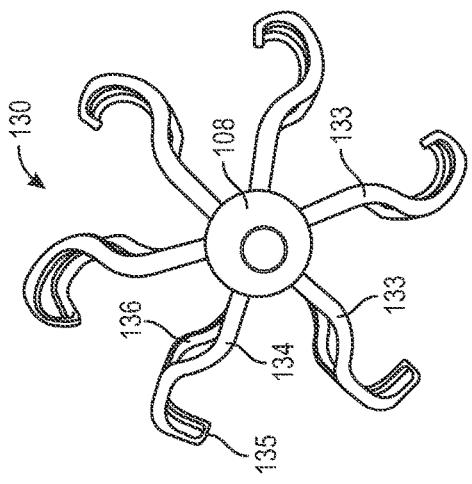

FIG. 1A is a side view of a stent cleaning system 100 ("system 100") in accordance with embodiments of the present technology. FIGS. 1B and 1C are an enlarged side view and an enlarged proximally-facing view, respectively, of a distal portion of the system 100 including a clot treatment device 130 in accordance with embodiments of the present technology. The stent cleaning system 100 can be used to remove clot material from (e.g., adhered to) the implant, to clean clot material from a native vessel in which the implant is implanted, and/or to remove clot material from a native vessel in which no implants are implanted. Accordingly, the system 100 can also be referred to as a clot treatment system, a clot removal system, a thrombectomy system, and/or the like. The clot treatment device 130 can also be referred to as a clot removal device, a coring element, a clot engagement member, a thrombectomy device, and/or the like.

Referring to FIGS. 1A and 1B together, in the illustrated embodiment the system 100 includes a proximal handle 110 operably coupled to a clot treatment device 130 via an inner elongate member 102 (obscured in FIG. 1A; e.g., a second elongate member) and a middle elongate member 104 (e.g., a first elongate member). The inner elongate member 102 can extend through a lumen of the middle elongate member 104 such that the inner and middle elongate members 102, 104 (collectively "elongate members 102, 104") are coaxial. The system 100 can further include an outer elongate member 106 (e.g., a third elongate member, a guide catheter), and the elongate members 102, 104 can at least partially extend through the outer elongate member 106 such that the inner, middle, and outer elongate members 102, 104, 106 (collectively "elongate members 102-106") are coaxial. In other embodiments, the elongate members 102, 104 are not coaxial and can instead extend side-by-side and/or through separate lumens of the outer elongate member 106. The elongate members 102-106 can comprise catheters, tubes (e.g., hypotubes), sheaths, shafts, and/or the like and can be formed from metal (e.g., stainless steel, nitinol), plastic, fluoropolymers (e.g., polytetrafluoroethylene (PTFE)), polymers, and/or other suitable materials. The outer elongate member 106 can comprise a guide catheter.

Referring to FIG. 1A, the outer elongate member 106 can include a distal end portion 107a and a proximal end portion 107b. The proximal end portion 107b can be coupled to a tubing assembly 101 (e.g., including one or more tubes, fluid control devices, and/or the like) via a valve device 109. In some embodiments, the tubing assembly 101 can be used to flush the lumen of the outer elongate member 106. In some embodiments, the handle 110 is movable (translatable, rotatable) relative to the valve device 109 and the outer elongate member 106. In the illustrated embodiment, the handle 110 has been advanced toward the valve device 109 such that the clot treatment device 130 extends from the distal end portion 107a of the outer elongate member 106. In some embodiments, the handle 110 can be retracted away from the outer elongate member 106 and/or the outer elongate member 106 can be advanced away from the handle 110 such that the clot treatment device 130 is captured/positioned within the outer elongate member 106. When the clot treatment device 130 is captured within the lumen of the outer elongate member 106, the clot treatment device 130 is in a radially-compressed state. In some embodiments, the clot treatment device 130 can be positioned within the outer elongate member 106 during delivery of the system 100 through the vasculature.

In the illustrated embodiment, the system 100 includes a tip 108 coupled to the clot treatment device 130 and/or the inner elongate member 102 (FIG. 1B). The tip 108 can have an atraumatic shape configured to minimize or even prevent damage to the vasculature as the system 100 is advanced therethrough. In other embodiments, the tip 108 can have other shapes or can be omitted entirely. In some embodiments, when the clot treatment device 130 is constrained within the outer elongate member 106, the tip 108 can engage the distal end portion 107a of the outer elongate member 106 and can be shaped and sized to seal the lumen of the outer elongate member 106. In some embodiments, the tip 108 and the inner elongate member 102 (FIG. 1B) can define a lumen configured (e.g., shaped and sized) to receive a guidewire (not shown) therethrough. The system 100 can be advanceable/trackable over the guidewire.

Referring to FIG. 1B, in the illustrated embodiment the inner elongate member 102 includes a distal end portion 103a coupled to a distal end portion 131a of the clot treatment device 130. Similarly, the middle elongate member 104 includes a distal end portion 105a coupled to a proximal end portion 131b of the clot treatment device 130. Accordingly, as described in detail below with reference to FIGS. 6A and 6B, relative movement of the elongate members 102, 104 can longitudinally shorten/lengthen and radially expand/compress the clot treatment device 130 via the relative movement of the end portions 131a-b. The end portions 131a-b of the clot treatment device 130 can be identical and can have a cylindrical or hub-like shape. In some embodiments, the end portions 131a-b are secured to the elongate members 102, 104, respectively, via adhesive (e.g., glue bonds), welding, fasteners, crimping (e.g., via a crimp tube), and/or the like. For example, in some embodiments one or both of the end portions 131a-b of the clot treatment device 130 can be directly welded to the elongate members 102, 104, or one or both of the end portions 131a-b can be crimped via a crimp tube to the elongate members 102, 104 (e.g., the proximal end portion 131b can be crimped to the middle elongate member 104). In some embodiments, the distal end portion 131a includes/defines a distal window 132a extending therethrough, and the proximal end portion 131b includes/defines a proximal window 132b extending therethrough. Coupling members (not shown), such as steel discs, can be placed in one or both of the windows 132a-b and welded, soldered, crimped, or otherwise fastened to the elongate members 102, 104, respectively, to secure the end portions 131a-b to the elongate members 102, 104 via a rivet-like lock. In some embodiments, the end portions 131a-b can include multiple ones of the windows 132a-b extending circumferentially thereabout, each configured to receive a corresponding coupling member.

The elongate members 102, 104 can comprise (i) metal, polymeric, and/or metallic (e.g., solid stainless steel, cobalt chrome, nitinol) tubes, (ii) metal, polymeric, and/or metallic (e.g., solid stainless steel, cobalt chrome, nitinol) tubes with relief cuts (e.g., laser-cuts) for flexibility, (iii) hollow helical spirals (e.g., including one or more axial metal (e.g., stainless-steel, cobalt chrome, nitinol) wires turned to create a closed-pitch coil with a hollow central lumen), (iv) reinforced polymeric shafts, and/or (v) the like. In the illustrated embodiment, for example, the inner elongate member 102 comprises a solid nitinol tube and the middle elongate member 104 comprises a hollow helical spiral (HHS). The hollow helical spiral can be a single layer spiral, or a multilayer spiral (e.g., two-layer, three-layer, or more layer spiral) to provide greater torque and/or tensile response. In some aspects of the present technology, such a hollow helical spiral allows the overall system 100 to be more flexible such that the system 100 can, for example, be inserted to treat clot material in more tortuous anatomies with less biasing of the clot treatment device 130 (e.g., to one side of an implant or vessel). In some aspects of the present technology, the elongate members 102, 104 can have a relatively high tensile, compression, and/or torque capability/response that allow for the controlled expansion and movement of the clot treatment device 130 during a procedure to remove clot material from an implanted stent, embolic protection device, other implant, and/or bare vessel, as described in greater detail below.

Referring to FIGS. 1B and 1C together, the clot treatment device 130 includes a plurality of beams or struts 133 extending between the end portions 131a-b and generally axially relative to a longitudinal axis L of the clot treatment device 130. More specifically, the struts 133 can be generally similar or identical to one another and can each include: (i) a distal portion 134 extending from the distal end portion 131a in a direction away from the longitudinal axis L and proximally toward the proximal end portion 131b (e.g., at an angle relative to the longitudinal axis L), (ii) a middle portion 135 extending from the distal portion 134 proximally and generally parallel to the longitudinal axis L, and (iii) a proximal portion 136 extending from the middle portion 135 to the proximal end portion 131b in a direction toward the longitudinal axis L (e.g., at an angle relative to the longitudinal axis L). In the illustrated embodiment, the clot treatment device 130 does not include any cross struts or other cross-members extending between (e.g., circumferentially between) the struts 133. That is, the struts 133 can each extend separately in a generally axial direction between the end portions 131a-b. In some aspects of the present technology, this absence of cross struts can permit the clot treatment device 130 to be advanced and retracted through an implanted stent (or other implant) without catching on the stent (e.g., catching on apices or ends of the stent), which could potentially damage, disrupt, and/or move the stent. In some embodiments, the clot treatment device 130 can include one or more cross-members between the struts 133—but that are not configured to contact the implanted stent when the clot treatment device 130 is expanded. For example, such cross-members can be positioned near the end portions 131a-b.

As best seen in FIG. 1B, in the illustrated embodiment the struts 133 each have an undulating (e.g., wave-like, saw-tooth-like, periodic) pattern. The undulating pattern of the struts 133 can create an abrasive surface for disrupting/engaging with clot and/or other material adhered to an implanted stent. More specifically, because of the undulating pattern, each of the struts 133 can include one or circumferential portions 137 that extend at least partially circumferentially relative to the longitudinal axis L. The circumferential portions 137 can together define the abrasive surface for disrupting the clot material. In some aspects of the present technology, the undulations are relatively small such to reduce the likelihood of the struts 133 catching on the stent when the clot treatment device 130 is advanced and retracted through the implanted stent.

As best seen in FIG. 1C, each of the struts 133 can curve radially at least partially back toward the longitudinal axis L in the middle portion 135 (and/or at a transition region between the middle portion 135 and distal and proximal portions 134, 136) such that the struts 133 have a wave-like or hook-like shape when viewed along the longitudinal axis L. In some embodiments, this shape can help facilitate the uniform collapse of the clot treatment device 130. In additional aspects of the present technology, the hook-like shape of the struts 133 can improve the ability of the clot treatment device 130 to engage and disrupt clot material within an implant while still being atraumatic to regions of the native vessel outside the implant (e.g., proximal and distal of the implant).

The clot treatment device 130 has nine of the struts 133 in FIG. 1B and six of the struts 133 in FIG. 1C for illustration. In other embodiments, the clot treatment device 130 can include any number of the struts 133 (e.g., one, two, three, four, five, seven, eight, ten, or more than ten) and the struts 133 can be positioned symmetrically or asymmetrically about the longitudinal axis L. For example, in some embodiments the struts 133 can be asymmetrically positioned about the longitudinal axis L to facilitate targeted engagement of the struts 133 with a region of adherent clot and/or to inhibit or even prevent catching of the clot treatment device 130 on bent portions of an implant (e.g., when the implant is positioned within tortuous anatomy). In some embodiments, the distal portions 134 of the struts 133 can be circumferentially offset from the proximal portions 136 of the struts 133—either permanently or via differential rotation of the elongate members 102, 104—to cause the struts 133 to assume a "scoop-like" shape when radially compressed, as described in greater detail below with reference to FIGS. 10A-10C. That is, for example, the distal portion 134 of each of the struts 133 can connect to the distal end portion 131a at a different circumferential position (e.g., relative to the longitudinal axis L) than the proximal portion 136 of the strut 133 connects to the proximal end portion 131b.

In some embodiments, the clot treatment device 130 is an integral/continuous structure, such as a laser-cut metal (e.g., nitinol, cobalt chrome, stainless steel) element. In some embodiments, the clot treatment device 130 is configured (e.g., heat set) to self-expand from a compressed delivery state (e.g., when the clot treatment device 130 is positioned within the outer elongate member 106) to the expanded deployed state illustrated in FIGS. 1B and 1C. In other embodiments, the clot treatment device 130 is configured (e.g., heat set) to collapse to the compressed delivery state from the expanded state. In such embodiments, biasing the clot treatment device 130 to collapse can help ensure that the clot treatment device 130 can be removed from the patient if one of the struts 133 or a connection point breaks during operation, as the clot treatment device 130 will automatically collapse for removal.

Figure 2A:
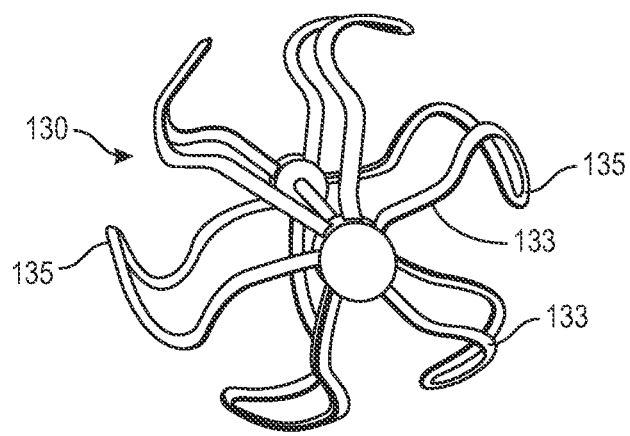
FIGS. 2A-2C are enlarged proximally-facing views of a distal portion of the system of FIG. 1A including the clot treatment device in accordance with additional embodiments of the present technology.
Figure 2B:
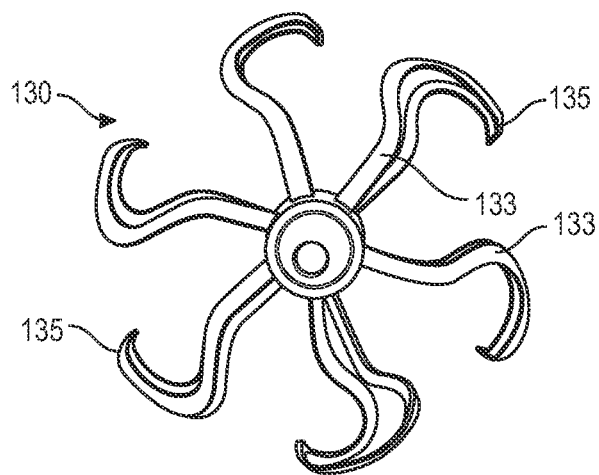
Figure 2C:
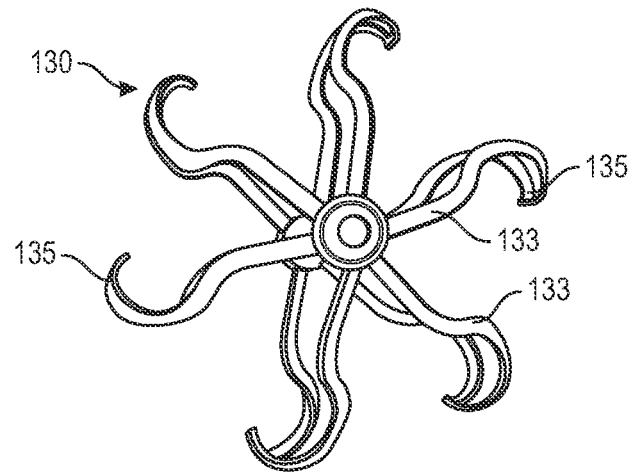

In some embodiments, the struts 133 can curve more or less back toward the longitudinal axis L. FIGS. 2A-2C, for example, are enlarged proximally-facing views of a distal portion of the system 100 including the clot treatment device 130 in accordance with additional embodiments of the present technology. Referring to FIGS. 2A-2C together, the middle portion 135 of each of the struts 133 of the clot treatment device 130 has (i) a relatively flat profile in the embodiment of FIG. 2A, (ii) a hook-shaped profile in the embodiment of FIG. 2B, and (iii) a further hook-shaped profile in the embodiment of FIG. 2C. In some aspects of the present technology, (i) the flatter profile shown in FIG. 2A can provide a longer cutting edge for engaging clot material adhered to an implant, (ii) the more hook-shaped profile shown in FIG. 2B can provide for a smaller contact area between the clot treatment device 130 and an implant that can reduce the likelihood of the clot treatment device 130 damaging the implant and that can be more atraumatic to a native vessel when the clot treatment device 130 is deployed at least partially outside the implant, and (iii) the further hook-shaped profile shown in FIG. 2C can provide an even smaller cutting surface than the profile shown in FIG. 2B to further reduce the likelihood of implant or native vessel damage as compared to the profile of FIG. 2B. In some embodiments, the flatter profile shown in FIG. 2A can be utilized to treat adherent clot material that is firmly attached to the implant.

Figure 3A:
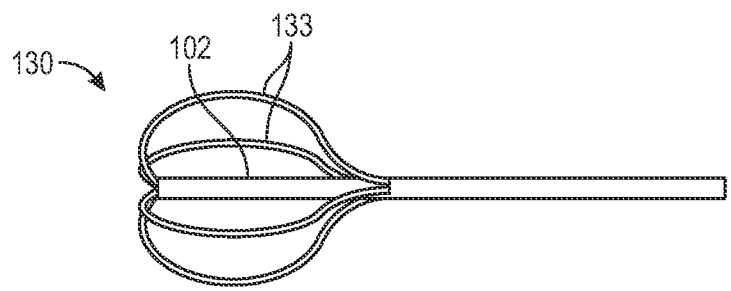
FIGS. 3A-3D are enlarged side views of a distal portion of the system of FIG. 1A including the clot treatment device in accordance with additional embodiments of the present technology.
Figure 3B:
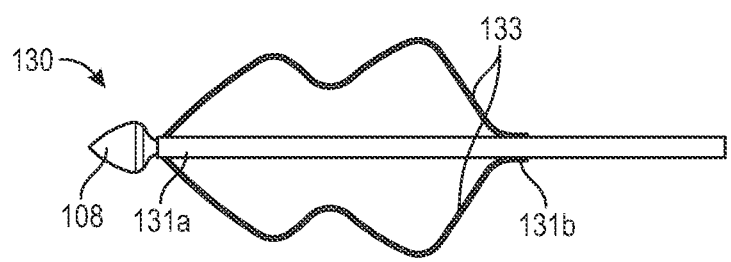
Figure 3C:
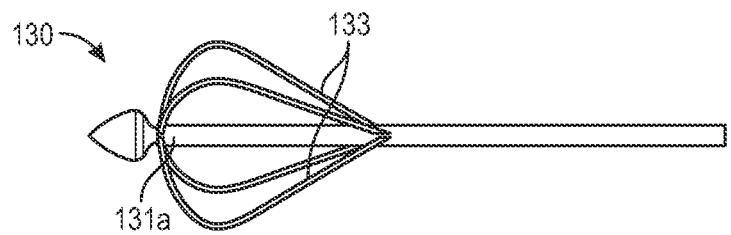
Figure 3D:
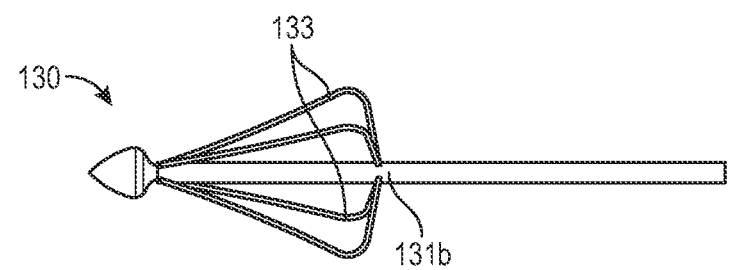

Similarly, in other embodiments one or more of the struts 133 can have different shapes and/or profiles. For example, FIGS. 3A-3D are enlarged side views of a distal portion of the system 100 including the clot treatment device 130 in accordance with additional embodiments of the present technology. In some embodiments, as shown in FIG. 3A, the tip 108 (FIG. 3B) can be omitted and the struts 133 can extend to and past the distalmost end of the inner elongate member 102 in the expanded position. As shown in FIG. 3B, one or more of the struts 133 can have a profile including multiple (e.g., two) bumps or peaks between the end portions 131a-b. As shown in FIG. 3C, one or more of the struts 133 can have an axial apex positioned near the distal end portion 131a (e.g., including a proximal tapered portion). As shown in FIG. 3D, one or more of the struts 133 can have an axial apex positioned near the proximal end portion 131b (e.g., including a distal tapered portion).

Figure 4A:
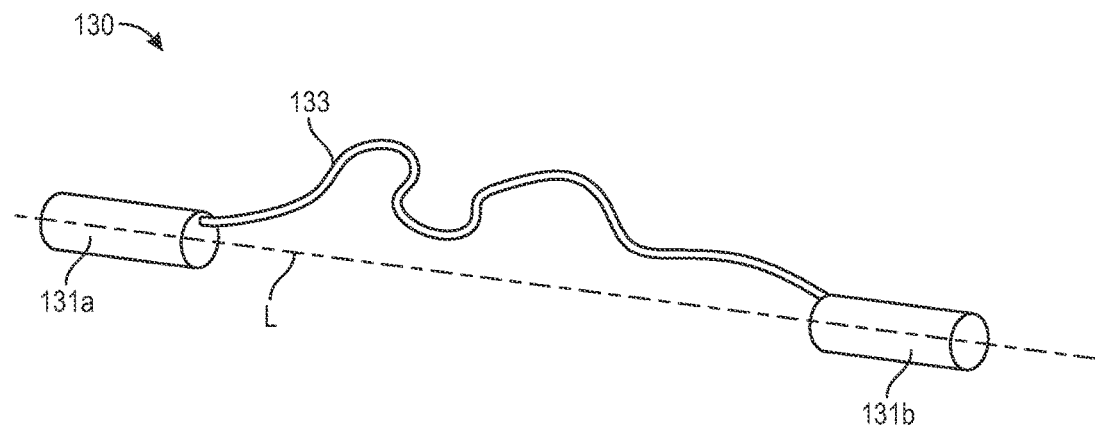
FIGS. 4A-4C are enlarged isometric views of a distal portion of the system of FIG. 1A including the clot treatment device in accordance with additional embodiments of the present technology.
Figure 4B:
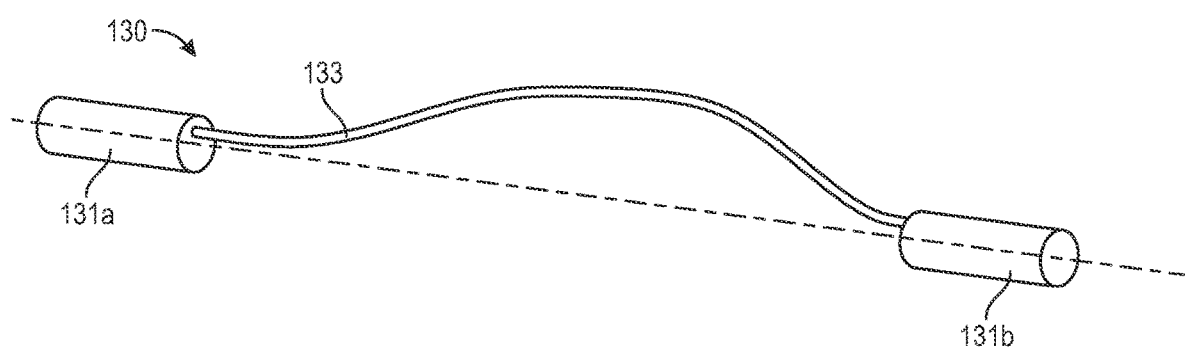
Figure 4C:
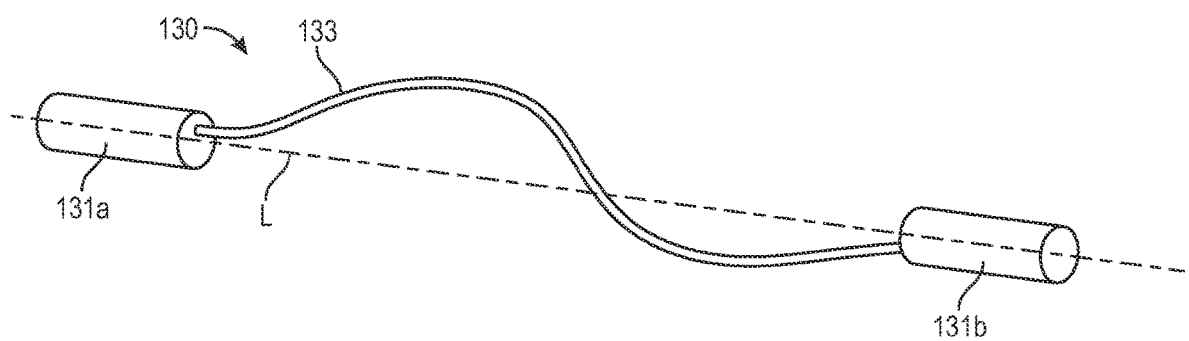

Further, FIGS. 4A-4C are enlarged isometric views of a distal portion of the system 100 including one of the struts 133 of the clot treatment device 130 in accordance with additional embodiments of the present technology. As shown in FIG. 4A, one or more of the struts 133 can have a profile including multiple (e.g., two) bumps or peaks between the end portions 131a-b and that does not extend radially about the longitudinal axis L and the inner elongate member 102 (FIG. 1B). As shown in FIG. 4B, one or more of the struts 133 can have a profile including a smoothly sloping shape between the distal and proximal end portions 131a-b. As shown in FIG. 4C, one or more of the struts 133 can extend radially about (e.g., spiral about) the longitudinal axis L and the inner elongate member 102 (FIG. 1B) between the end portions 131a-b.

Figure 5:
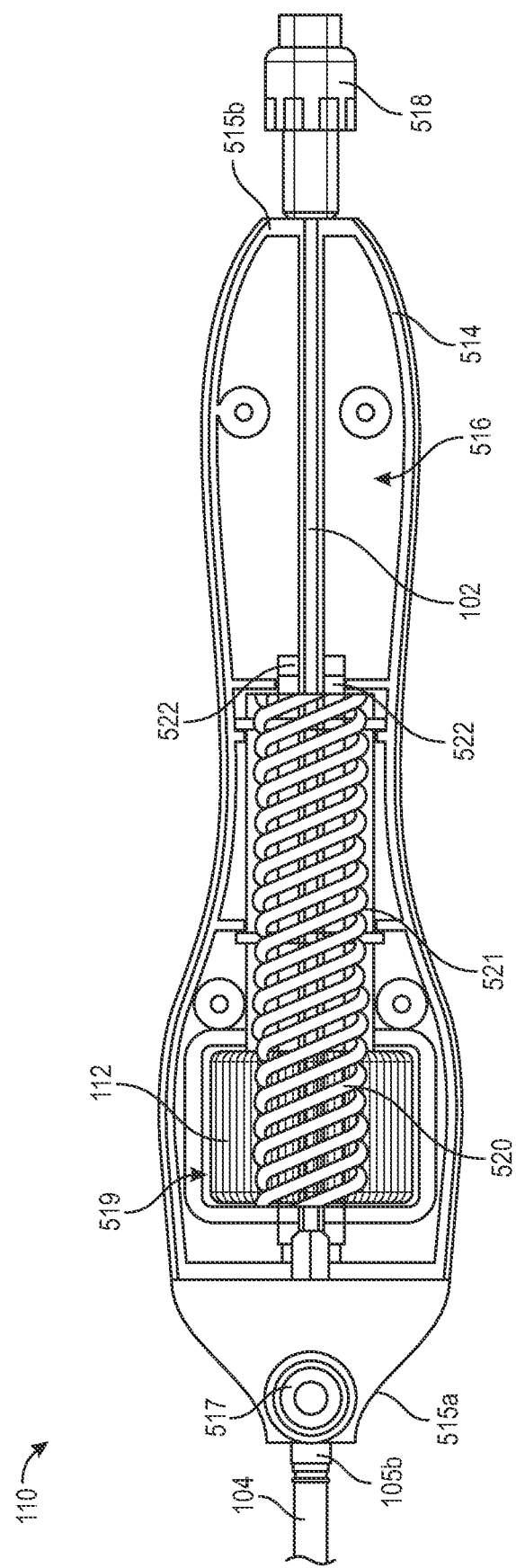
FIG. 5 is a partially cut-away view of a handle of the system of FIG. 1A in accordance with embodiments of the present technology.

FIG. 5 is a partially cut-away view of the handle 110 of the FIG. 1A in accordance with embodiments of the present technology. In the illustrated embodiment, the handle 110 includes a housing 514 having a distal portion 515a and a proximal portion 515b and defining an internal chamber or lumen 516. The housing 514 is shown as partially-cut away in FIG. 5 for clarity. A proximal portion 105b of the middle elongate member 104 can be fixedly coupled to the distal portion 515a of the housing 514. In some embodiments, the handle 110 includes a flush port 517 operably (e.g., fluidly) coupled to the lumen of the middle elongate member 104. The inner elongate member 102 can extend through the lumen of the middle elongate member 104, past the proximal portion 105b of the middle elongate member 104, and into the lumen 516 of the housing 514. In some embodiments, the inner elongate member 102 can extend entirely through the housing 514 to a flush port 518 coupled to the proximal portion 515 of the housing 514.

In the illustrated embodiment, the handle 110 further comprises a leadscrew 520 attached to the inner elongate member 102 and movably positioned within the lumen 516 over one or more guiderails 522 (e.g., a pair of guiderails 522). The leadscrew 520 can have a threaded outer surface configured to mate with a threaded inner surface of the actuator 112 (shown as partially transparent in FIG. 5 for clarity). Alternatively, the leadscrew 520 can have a threaded inner surface configured to mate with a threaded outer surface of the actuator 112 as described, for example, in detail below with reference to FIG. 26. The actuator 112 can extend out of the housing 514 from one or more openings 519 therein (e.g., a pair of openings on opposing sides of the housing 514) such that the actuator 112 is accessible outside the housing 514 by a user of the handle 110 (e.g., a physician). In some embodiments, the handle 110 further includes a leadscrew knob 521 (shown as partially transparent in FIG. 2 for clarity) coupled to the actuator 112 and configured to threadably engage the leadscrew 520 over an entire range of movement of the actuator 112.

Rotation of the actuator 112 relative to the housing 514 (e.g., by the user) can drive the leadscrew 520 to translate proximally and/or distally (e.g., between the distal and proximal portions 515a-b of the housing 514) to thereby drive the attached inner elongate member 102 to translate relative to the middle elongate member 104. This relative movement of the elongate members 102, 104 lengthens/shortens the clot treatment device 130 (FIGS. 1A-1C) to radially compress/expand the clot treatment device 130. More specifically, FIGS. 6A and 6B are side views of a distal portion of the system 100 including the clot treatment device 130 in a first position (e.g., a radially-expanded position) and a second position (e.g., a radially-compressed position), respectively, in accordance with embodiments of the present technology. Referring to FIGS. 5-6B together, in the first position (FIG. 6A) the clot treatment device 130 is radially expanded, having a first diameter $D_1$ and a first length $X_1$, and in the second position the clot treatment device 130 is radially compressed, having a second diameter $D_2$ less than the first diameter $D_1$ and a second length $X_2$ greater than the first length $X_1$. In both the first and second positions the clot treatment device 130 has been advanced distally out of the outer elongate member 106 (e.g., past the distal end portion 107a thereof).

To move the clot treatment device 130 from the first position to the second position, the user can rotate the actuator 112 in a first direction to drive the leadscrew 520 distally through the housing 514. This movement drives the inner elongate member 102 distally through the lumen of the middle elongate member 104, thereby driving the distal end portion 131a of the clot treatment device 130 distally relative to the proximal end portion 131b to radially compress the clot treatment device 130 while lengthening the clot treatment device 130. Conversely, to move the clot treatment device 130 from the second position to the first position, the user can rotate the actuator 112 in a second direction opposite the first direction to drive the leadscrew 520 proximally through the housing 514. This movement drives the inner elongate member 102 proximally through the lumen of the middle elongate member 104, thereby driving the distal end portion 131a of the clot treatment device 130 proximally relative to the proximal end portion 131b to radially expand the clot treatment device 130 while shortening the clot treatment device 130. Although two discrete positions are shown in FIGS. 6A and 6B, the clot treatment device can be expanded to any number of continuous positions therebetween, to a position further radially expanded than the first position, and/or to a position less radially expanded than the second position. Moreover, in other embodiments the middle elongate member 104 can be operably coupled to the leadscrew 520 and the actuator 112 instead of or in addition to the inner elongate member 102 such that actuation of the actuator 112 drives the middle elongate member 104 relative to the inner elongate member 102, or both the inner elongate member 102 and the middle elongate member 104 relative to the handle 110, to radially expand/compress the clot treatment device 130.

Referring to FIG. 1A, in some embodiments the handle 110 can further include an indicator 111, such as a slider, configured to provide a visual indication of an amount of radial expansion of the clot treatment device 130. The indicator 111 can, for example, indicate whether the clot treatment device 130 is in the first position or the second position. In some embodiments, the indicator 111 includes detents and/or other features that provide an indication (e.g., a "clicking" sound) as the clot treatment device 130 is incrementally expanded/collapsed (e.g., millimeter by millimeter). Similarly, the indicator 111 can include markings that indicate an expanded size of the clot treatment device 130 as described in, for example, detail below with reference to FIGS. 25A-26.

Referring to FIGS. 1A-1C together, in other embodiments a handle of the system 100 can include a first member coupled to the inner elongate member 102 and a second member coupled to the middle elongate member 104. One or both of the first and second members can be manually moved relative to one another (e.g., without any mechanical advantage provided by a leadscrew, gear, or the like) to radially expand/compress the clot treatment device 130 as shown in FIGS. 6A and 6B.

Figure 7:
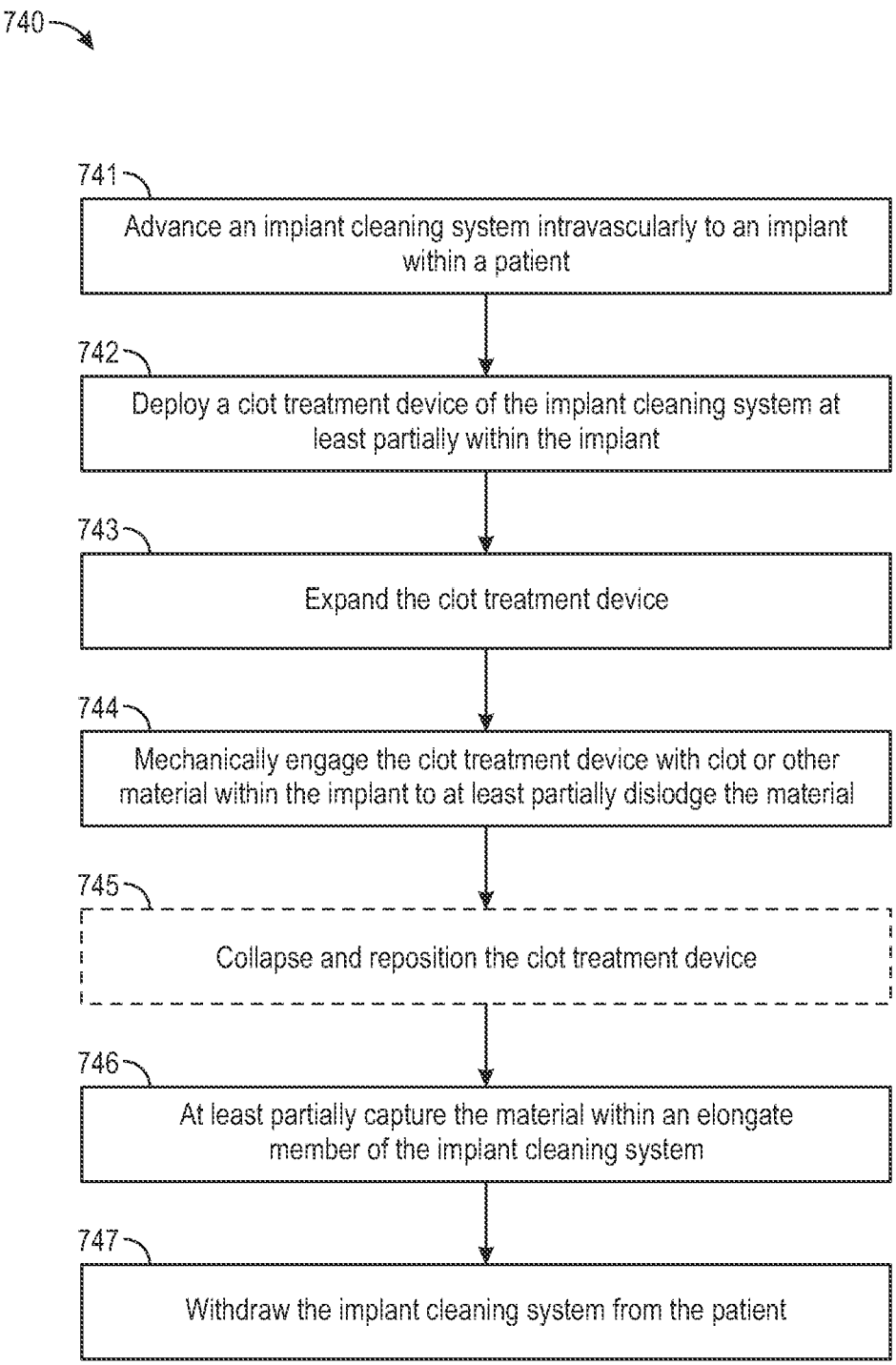
FIG. 7 is a flow diagram of a process or method for operating the system of FIG. 1A during an intravascular procedure to remove clot material from an implanted stent in accordance with embodiments of the present technology.

FIG. 7 is a flow diagram of a process or method 740 for operating the system 100 during an intravascular procedure to remove material from an implant with a patient in accordance with embodiments of the present technology. Although some features of the method 740 are described in the context of the embodiments shown in FIGS. 1A-6B for the sake of illustration, one skilled in the art will readily understand that the method 740 can be carried out using other suitable systems and/or devices described herein.

At block 741, the method 740 can include advancing the system 100 through the vasculature of a patient to at or proximate the implant implanted within the patient. The implant can be identified as having clot material or other unwanted material (e.g., intimal hyperplasia) adhered thereto that would be beneficial to remove. In some embodiments, the implant is a stent implanted within the venous vasculature of the patient. In other embodiments, the implant can be a graft, embolic filter, inferior vena cava (IVC) filter, and/or other type of implant. In other embodiments, the method 740 can be used to clean and remove clot material from a bare vessel of the patient. In some embodiments, the elongate members 102-106 can be advanced together through the vasculature with the clot treatment device 130 constrained within the outer elongate member 106. The tip 108 can provide for atraumatic advancement of the system 100 through the vasculature to the implant. In other embodiments, the outer elongate member 106 can be positioned within the vasculature first, and the clot treatment device 130 can then be advanced through the vasculature to the implant.

At block 742, the method 740 can include deploying the clot treatment device 130 within the implant. For example, the handle 110 can be advanced distally (e.g., pushed by a physician) relative to the outer elongate member 106 to advance the elongate members 102, 104 and the coupled clot treatment device 130 distally from the distal end portion 107a of the outer elongate member 106. In some embodiments, the clot treatment device 130 can at least partially radially expand (e.g., self-expand) when the clot treatment device 130 is no longer constrained by the outer elongate member 106.

At block 743, the method 740 can include further radially expanding the clot treatment device 130. For example, the clot treatment device 130 can be radially expanded by actuating the actuator 112 of the handle 110 to drive the inner elongate member 102 proximally relative to the middle elongate member 104 to thereby move the distal end portion 131a of the clot treatment device 130 toward the proximal end portion 131b—thereby causing the struts 133 to flex radially outwardly away from the longitudinal axis L. In some embodiments, the clot treatment device 130 is radially expanded outwardly to contact the clot material adhered to the implant or the implant itself. In some aspects of the present technology, such radial expansion can comprise a mechanical "ballooning" effect of the clot treatment device 130. For example, the clot treatment device 130 can be expanded within a deformed or compressed stent to balloon open the stent and/or to disrupt clot material, intimal hyperplasia, and/or other material within the stent such that clot treatment device 130 can more effectively engage and disrupt clot material within the stent (block 744). In some embodiments, the clot treatment device 130 can be expanded within a bare vessel (e.g., outside a stent) to perform angioplasty. The clot treatment device 130 can provide a radial outward mechanical force (e.g., pressure) of between about 0.1-30 atmospheres, between about 0.1-6 atmospheres, etc. The outward mechanical force can be determined by the width and thickness of the struts 133 and/or the amount the clot treatment device 130 can be expanded (e.g., how far the leadscrew 520 can travel)—with greater strut thickness, strut width, and/or device expansion causing a greater outward mechanical force (and vice versa) In some aspects of the present technology, the clot treatment device advantageously does not include a burst failure mode like many conventional balloon treatment devices.

Figure 8:
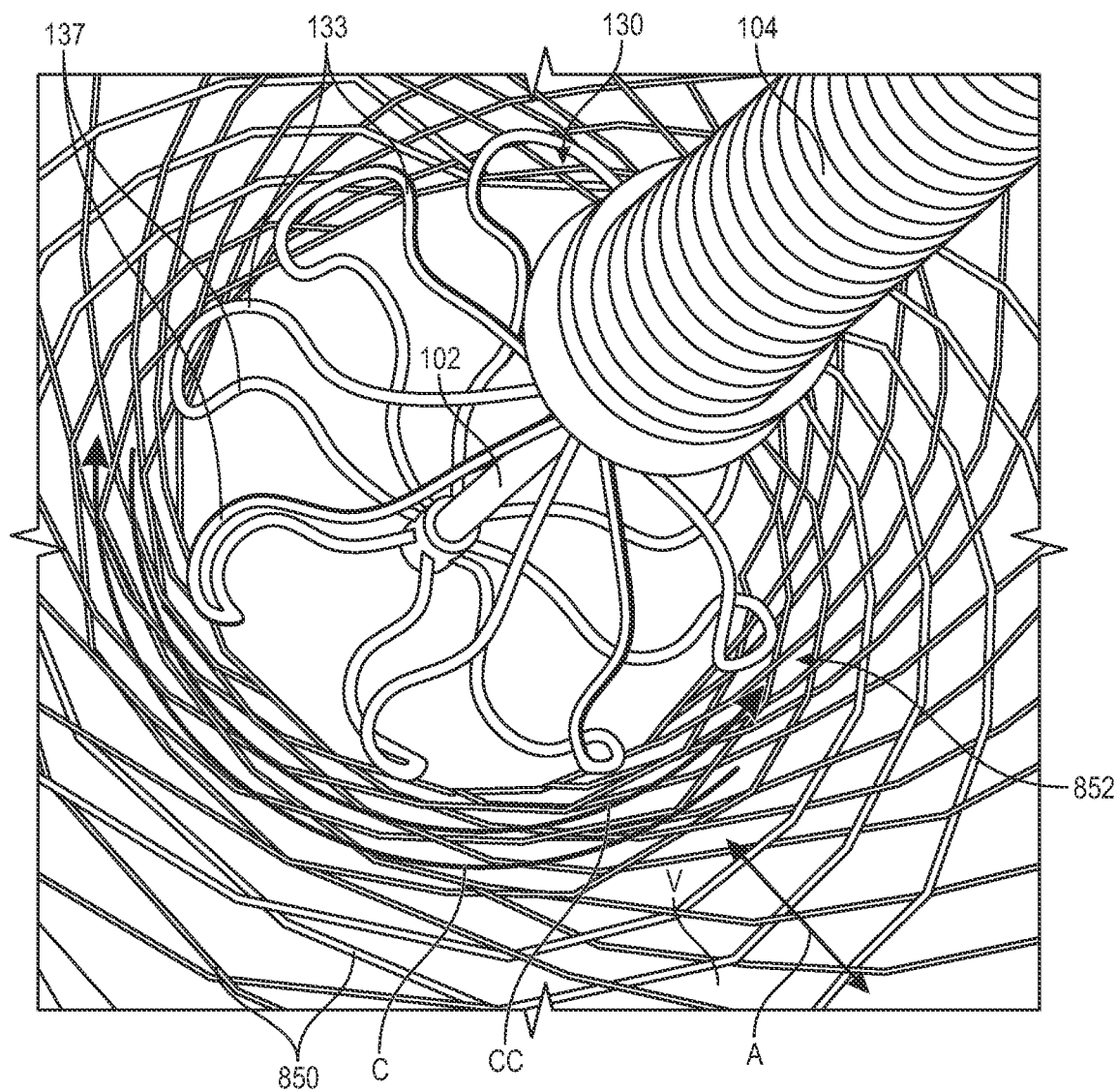
FIG. 8 is a distally-facing perspective view of a distal portion of the system of FIG. 1A including the clot treatment device expanded within a stent implanted in a vessel in accordance with embodiments of the present technology.

At block 744, the method 740 includes mechanically engaging the clot treatment device 130 with the clot material within the implant to at least partially dislodge the clot material. For example, the clot treatment device 130 can be rotated, translated, and/or radially compressed/expanded within the implant to engage and dislodge the clot material. Accordingly, in some aspects of the present technology the clot treatment device 130 can function similarly to a mechanical scoring balloon. More specifically, FIG. 8 is a distally-facing perspective view of a distal portion of the system 100 including the clot treatment device 130 expanded within an implant 850 (e.g., a stent) implanted in a vessel V in accordance with embodiments of the present technology. The clot material to be removed is omitted in FIG. 8 for clarity. The implant 850 can comprise a plurality of interconnected struts, graft material, a mesh, and/or other components know in the art of intravascularly implantable medical devices (e.g., stents)

In the illustrated embodiment, the clot treatment device 130 is expanded within a lumen 852 of the implant 850 such that the struts 133 contact an inner surface of the implant 850. In some embodiments, the struts 133 are the only part of the clot treatment device 130 that contacts the implant 850 when the clot treatment device 130 is expanded. With reference to FIGS. 1A and 8 together, the clot treatment device 130 can be (i) translated distally or proximally within the implant 850 (e.g., as indicated by arrow A in FIG. 8) by moving the handle 110 distally or proximally and/or (ii) rotated clockwise or counterclockwise within the implant 850 (e.g., as indicated by arrows C and CC, respectively, in FIG. 8) by rotating the handle 110. As described in detail above, the elongate members 102, 104 can be formed to be highly torqueable and to have high compression/tension resistance such that the movements of the handle 110 are translated without much loss to the clot treatment device 130. In some aspects of the present technology, the struts 133 are configured not to catch, grab, or damage the implant 850 when the clot treatment device 130 is moved relative to the implant 850 as, for example, the struts 133 extend generally axially along the direction of translation and do not include any cross-members or open cells. Additionally, the undulating shapes of the struts 133 (e.g., the circumferential portions 137) together define an abrasive surface for disrupting, cutting, and/or dislodging the clot material adhered to the implant 850. Accordingly, in some aspects of the present technology the system 100 can be used to remove chronic adherent clot while significantly reducing the risk of damaging the implant 850.

Figure 9A:
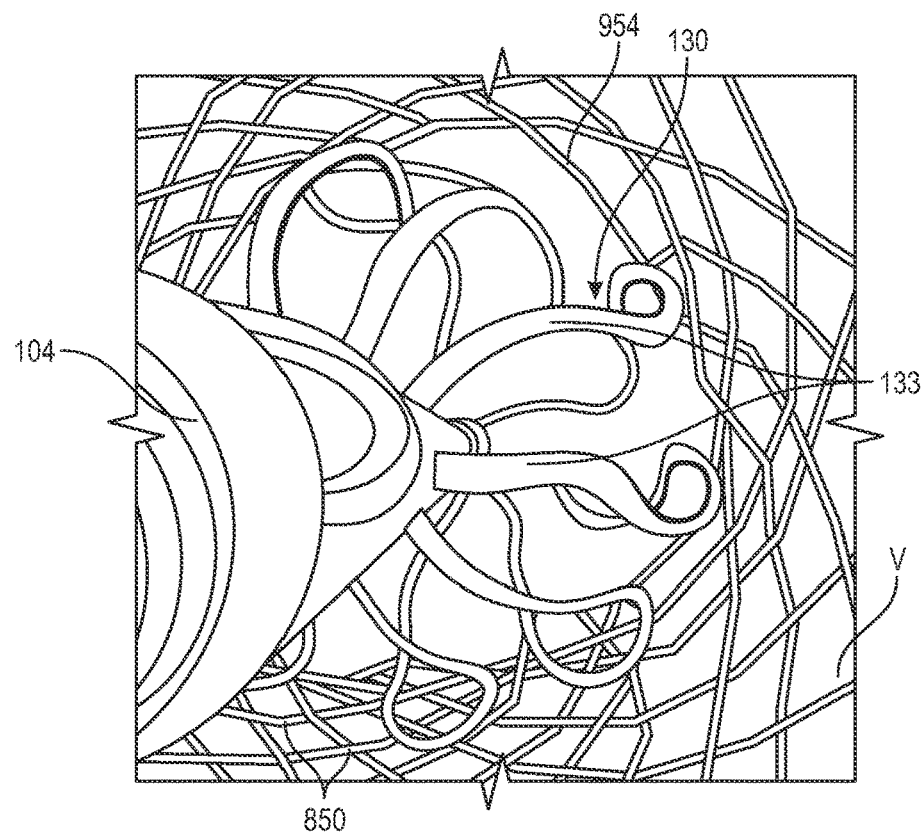
FIGS. 9A and 9B are distally-facing perspective views of a distal portion of the system of FIG. 1A including the clot treatment device positioned within the stent of FIG. 6 in accordance with embodiments of the present technology.
Figure 9B:
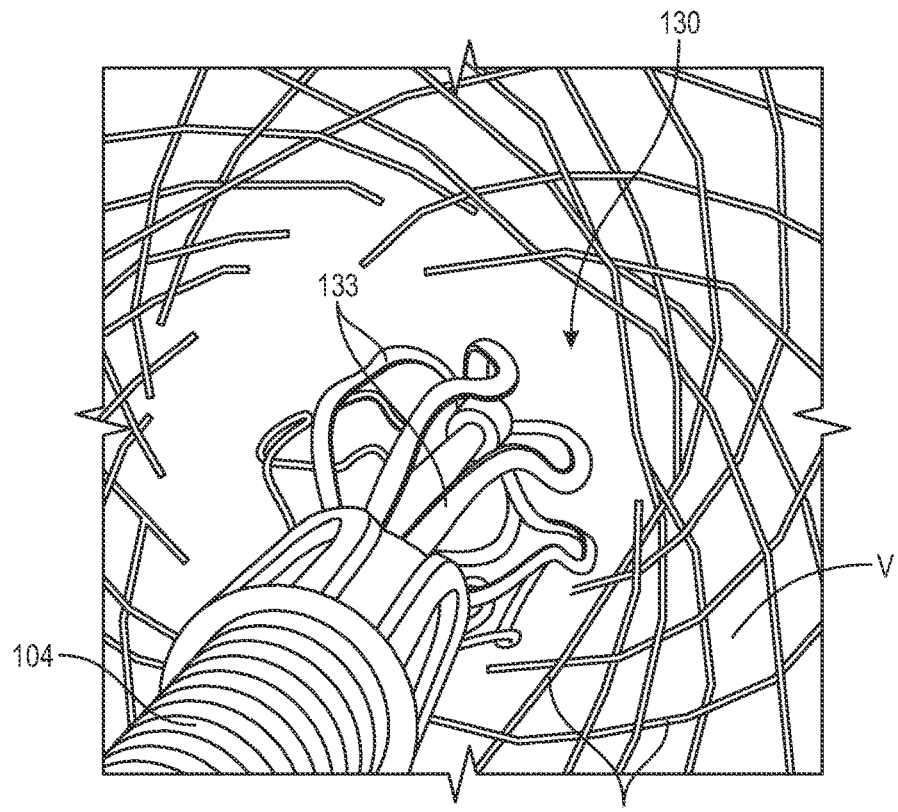

Referring again to FIG. 7, at block 745, the method 740 optionally includes collapsing and repositioning the clot treatment device 130. For example, if the clot treatment device 130 catches or becomes entangled with the implant, the clot treatment device 130 can be radially compressed (e.g., from the first position to the second position shown in FIGS. 6A and 6B, respectively) to disengage the implant. For example, FIGS. 9A and 9B are distally-facing perspective views of a distal portion of the system 100 including the clot treatment device 130 positioned within the implant 850 in the vessel V in accordance with embodiments of the present technology. FIG. 9A illustrates the clot treatment device 130 in a radially-expanded position and at least partially entangled with an end portion 954 of the implant 850. If such entanglement occurs, the clot treatment device 130 can be radially compressed as shown in FIG. 9B to free the struts 133 from the implant 850. In some aspects of the present technology, because the clot treatment device 130 does not include any cross-members between the struts 133, radially compressing the clot treatment device 130 can disengage the struts 133 from the implant 850 without catching or pulling the implant 850 therewith.

Referring again to FIG. 7, at block 746, the method 740 can include at least partially capturing the dislodged clot material within, for example, the outer elongate member 106. In some embodiments, the clot material dislodged from the implant (block 744) can flow into the outer elongate member 106 via the blood pressure within the vessel. In some embodiments, the clot treatment device 130 can be retracted proximally into the outer elongate member 106 to pull the clot material into the outer elongate member 106.

Finally, at block 747, the system 100 can be withdrawn from the patient. For example, the clot treatment device 130 can be retracted proximally into the outer elongate member 106 (e.g., by proximally withdrawing the handle 110 relative to the outer elongate member 106) and radially constrained therein. The outer elongate member 106 and the constrained clot treatment device 130 can then be withdrawn together from the patient.

Figure 10A:
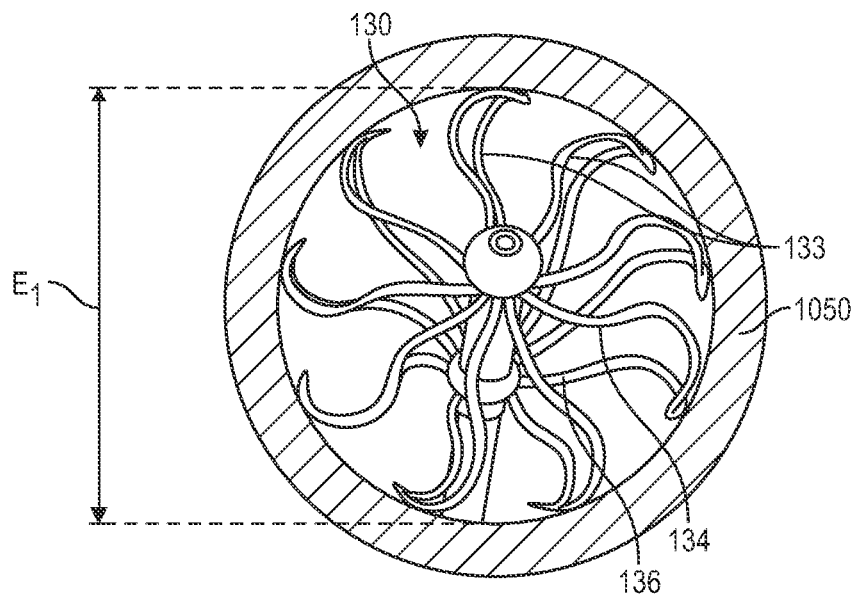
FIGS. 10A-10C are distally-facing perspective views of a distal portion of the system of FIG. 1A including the clot treatment device deployed within an implant with differing amounts of radial expansion in accordance with embodiments of the present technology.
Figure 10B:
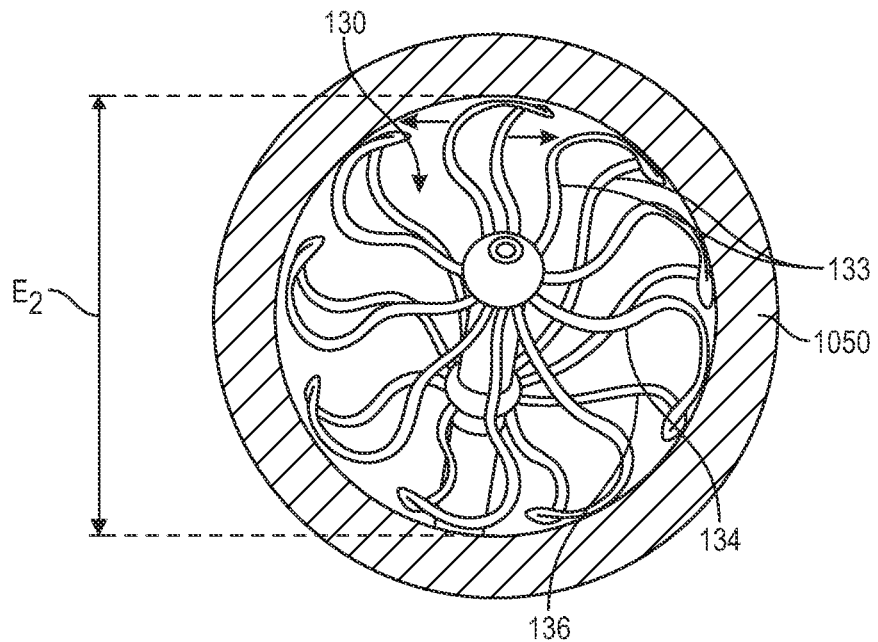
Figure 10C:
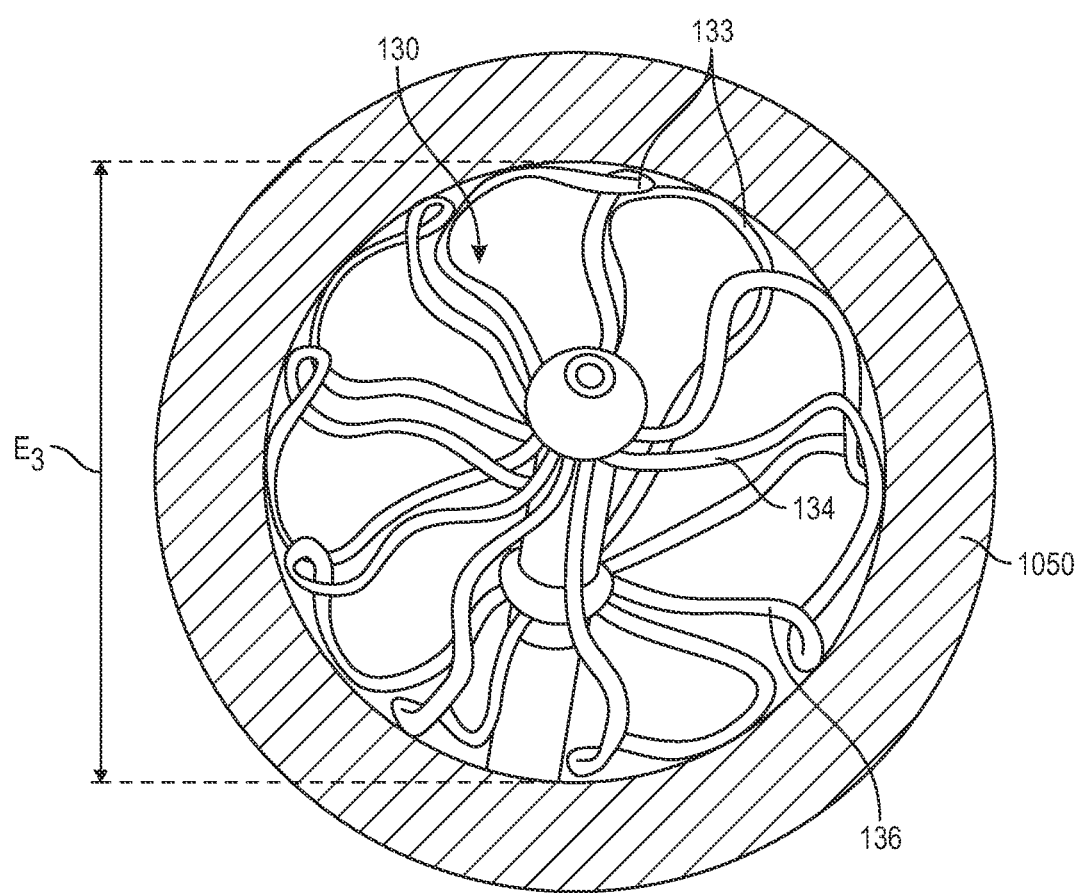

FIGS. 10A-10C are distally-facing perspective views of a distal portion of the system 100 including the clot treatment device 130 expanded within an implant 1050 with differing amounts of radial expansion in accordance with embodiments of the present technology. More specifically, FIGS. 10A-10C illustrate progressively increasing amounts of radial expansion caused by for, example, further actuation of the actuator 112 of the handle 110 to move the distal end portion 131a of the clot treatment device 130 proximally toward proximal end portion 131b of the clot treatment device as shown in and described in detail with reference to FIGS. 1A-6B. Alternatively, FIGS. 10A-10C illustrate the same amount of radial expansion of the clot treatment device 130 where the implant 1050 has a progressively decreasing diameter E1-E3.

Referring to FIGS. 10A-10C together, as the clot treatment device 130 is further expanded within the implant 1050, the struts 133 can progressively flex inward and turn to each have a scoop-like shape. More specifically, the distal and proximal portions 134, 136 of each strut can flex to be circumferentially offset relative to the longitudinal axis L (FIG. 1B) of the clot treatment device 130. Such radial offset can be facilitated by the different properties of the elongate members 104, 106. For example, as described in detail above, the inner elongate member 102 can comprise a solid tube while the middle elongate member 104 can comprise a hollow helical spiral such that there is more rotational give in the middle elongate member 104. Accordingly, when the clot treatment device 130 is rotated when it is engaged with a stent or other implant, the friction/engagement forces on the clot treatment device 130 can cause the relatively more flexible middle elongate member 104 to rotate less than the inner elongate member 102—thereby rotating the distal end portion 131a (FIGS. 6A and 6B) of the clot treatment device 130 more than the proximal end portion 131b (FIGS. 6A and 6B) and causing the scoop-like shape. In some aspects of the present technology, the scoop-like shape of the struts 133 shown in FIGS. 10B and 10C can facilitate a more effective removal of clot material from implant 1050. In other embodiments, the elongate members 104, 106 can be coupled to a handle configured to rotate the elongate members 104, 106 at different speeds to circumferentially offset the distal and proximal end portions of the struts 133 to thereby facilitate the scoop-like shape.

Figure 11A:
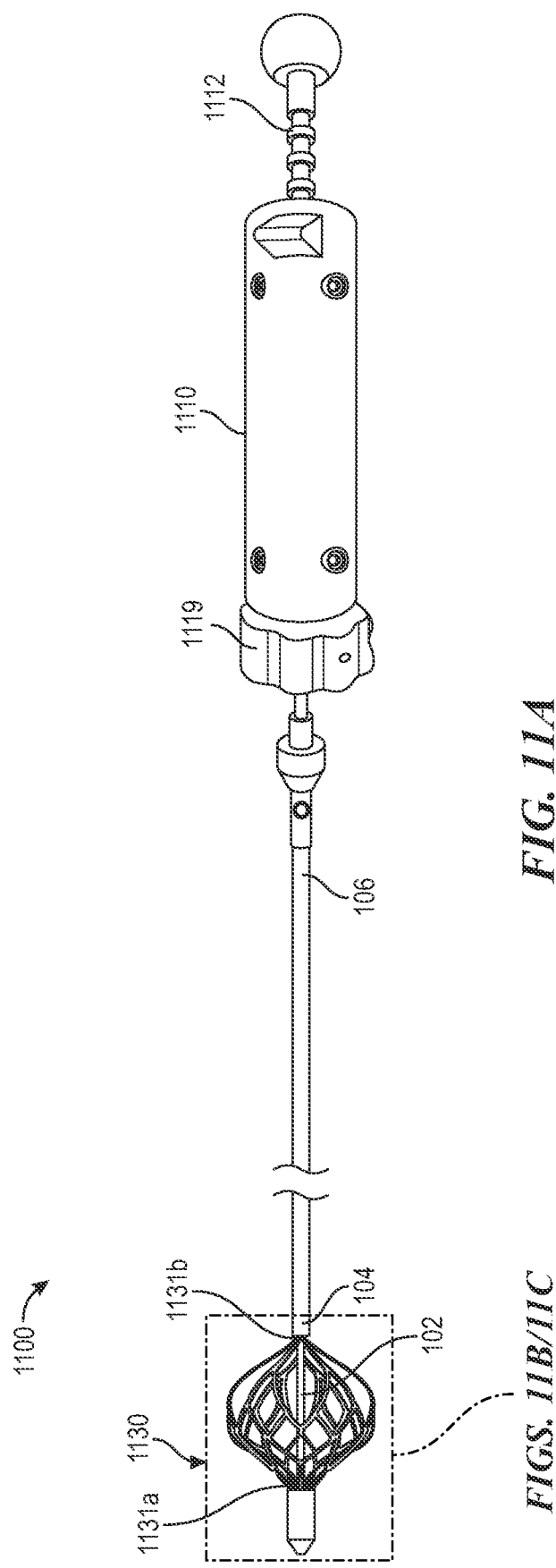
FIG. 11A is a side view of a stent cleaning system in accordance with embodiments of the present technology.

FIG. 11A is a side view of a stent cleaning system 1100 ("system 1100") in accordance with embodiments of the present technology. The system 1100 can include some features that are at least generally similar in structure and function, or identical in structure and function, to the corresponding features of the system 1100 described in detail above with reference to FIGS. 1A-10C, and can operate in a generally similar or identical manner to the system 100. For example, in the illustrated embodiment, the system 1100 includes a clot treatment device 1130 having a distal end portion 1131a coupled to the inner elongate member 102 and a proximal end portion 1131b coupled to the middle elongate member 104. The elongate members 102, 104 extend through the outer elongate member 106 and are operably coupled to a handle 1110 configured to radially expand/compress the clot treatment device 1130. In some embodiments, the system 1100 is configured for use in the peripheral vasculature to treat chronic peripheral clot either within a stent or other implant, or within a bare vessel.

Figure 11B:
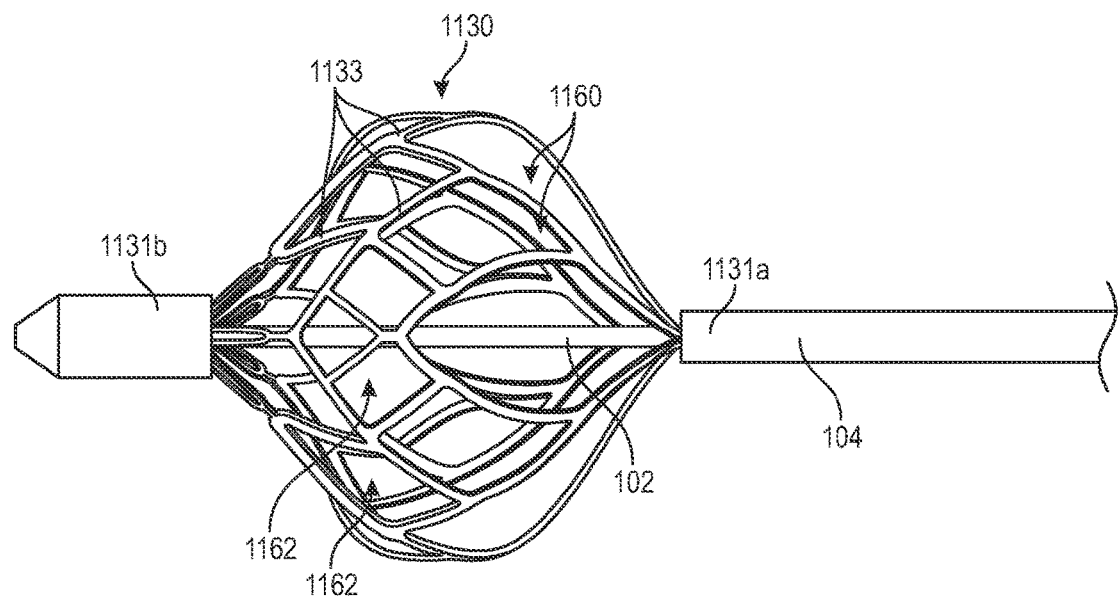
FIGS. 11B and 11C are side views of a distal portion of the system of FIG. 11A including a clot treatment device in a first position and a second position, respectively, in accordance with embodiments of the present technology.
Figure 11C:
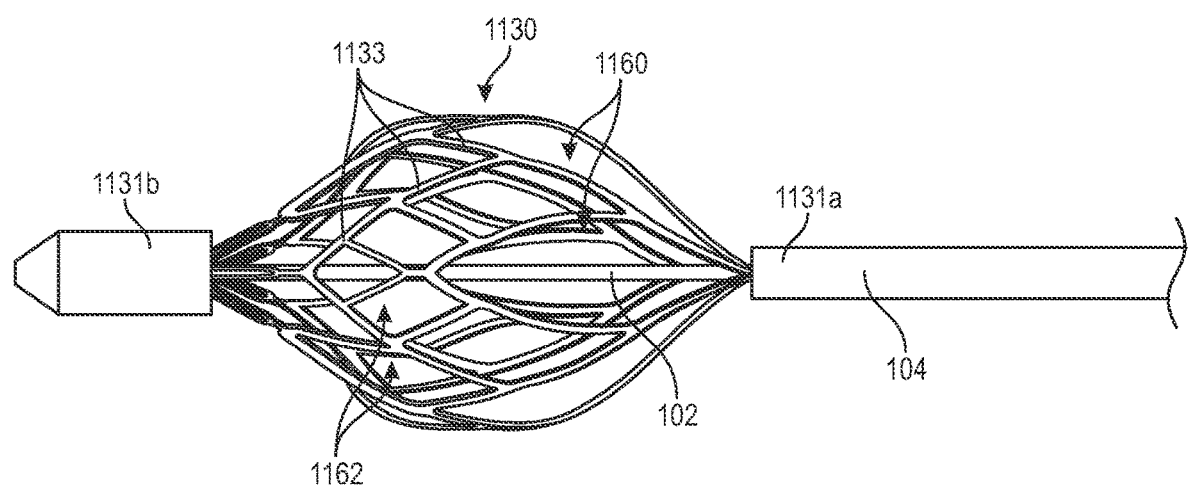

FIGS. 11B and 11C are side views of a distal portion of the system 1100 including the clot treatment device 1130 in a first position (e.g., a radially-expanded position) and a second position (e.g., a radially-compressed position), respectively, in accordance with embodiments of the present technology. In the illustrated embodiment, the clot treatment device 1130 includes a plurality of interconnected struts 1133 that extend between the distal and proximal end portions 1131a-b. In some embodiments, the struts 1133 define a plurality of proximal cells 1160 and a plurality of distal cells 1162. In the illustrated embodiment, the proximal cells 1160 are larger than the distal cells 1162. That is, the clot treatment device 1130 can have fewer of the struts 1133 near the proximal end portion 1131*b* than near the distal end portion 1131*a*. The clot treatment device 1130 can be formed of a self-expanding material, such as nitinol, and can be a unitary/integral structure. In some embodiments, the clot treatment device 1130 can be at least generally similar in structure and function, or identical in structure and function, to any of the clot treatment devices disclosed in U.S. patent application Ser. No. 17/072,909, titled "SYSTEMS, DEVICES, AND METHODS FOR TREATING VASCULAR OCCLUSIONS," and filed Oct. 16, 2020, which is incorporated herein by reference in its entirety.

Referring again to FIG. 11A, the handle 1110 can include a first actuator 1112 coupled to one of the elongate members 102, 104 (e.g., the inner elongate member 102). The other one of the elongate members 102, 104 (e.g., the middle elongate member 104) can be fixedly coupled to the handle 1110. In the illustrated embodiment, the first actuator 1112 is a pull member configured to be pulled proximally or advanced distally to move the elongate members 102, 104 relative to one another to radially compress or expand the clot treatment device 1130. In some embodiments, the handle 1110 further includes a second actuator 1119 operably coupled to both of the elongate members 102, 104 and configured to be rotated to rotate the elongate members 102, 104 together to rotate the clot treatment device 1130.

Referring to FIGS. 11A-11C together, in operation, the handle 1110 can be advanced distally and withdrawn proximally relative to the outer elongate member 106 to advance the clot treatment device 1130 from within the outer elongate member 106 and/or to withdraw the clot treatment device 1130 into the outer elongate member 106. When the clot treatment device 1130 is advanced out of the outer elongate member 106, the clot treatment device 1130 can self-expand within, for example, a stent or other implant to be cleaned. The first actuator 1112 can be pulled/withdrawn to move the clot treatment device 1130 between the first and second positions shown in FIGS. 11B and 11C. For example, when the first actuator 1112 is coupled to the inner elongate member 102, the first actuator 1112 can be advanced distally to drive the inner elongate member 102 distally relative to the middle elongate member 104 to drive the distal end portion 1131*a* of the clot treatment device 1130 distally relative to the proximal end portion 1131*b* to compress the clot treatment device 1130 (e.g., to move the clot treatment device 1130 from the first position to the second position). Likewise, the first actuator 1112 can be retracted proximally to drive the inner elongate member 102 proximally relative to the middle elongate member 104 to drive the distal end portion 1131*a* of the clot treatment device 1130 proximally relative to the proximal end portion 1131*b* to expand the clot treatment device 1130 (e.g., to move the clot treatment device 1130 from the second position to the first position). The second actuator 1119 can be rotated to rotate elongate members 102, 104 together to rotate the clot treatment device 1130 in either the first or second positions. Accordingly, when expanded within a stent or other implant, the system 1100 is operable to radially expand, translate, and/or rotate the clot treatment device 1130 within the stent to mechanically engage and dislodge clot or other material adhered thereto.

Figure 12:
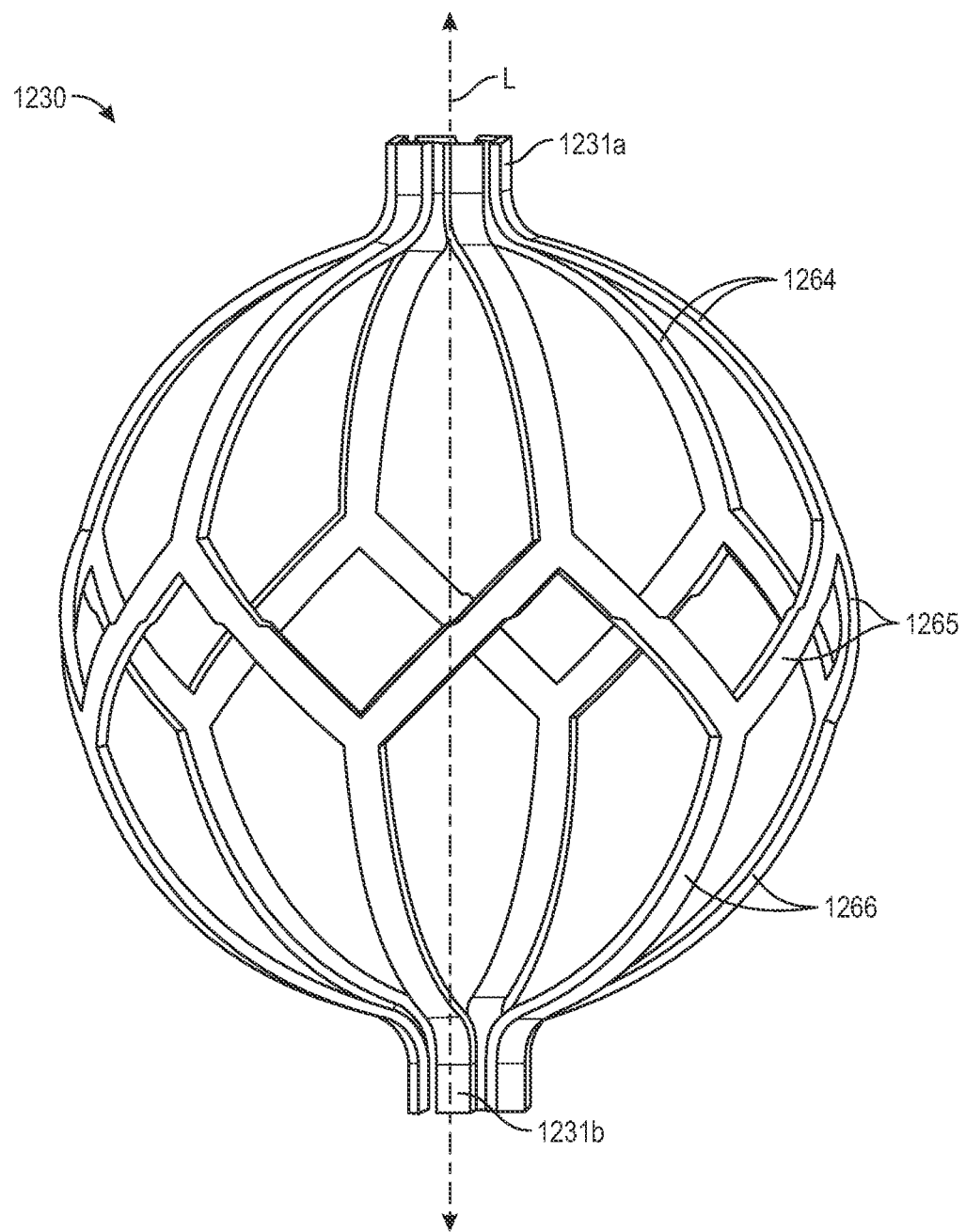
FIG. 12 is a side view of a clot treatment device in accordance with embodiments of the present technology.

FIG. 12 is a side view of a clot treatment device 1230 in accordance with embodiments of the present technology. The clot treatment device 1230 can include some features that are at least generally similar in structure and function, or identical in structure and function, to the corresponding features of the clot treatment devices 130 and/or 1130 described in detail above with reference to FIGS. 1A-11C, and can be employed within a clot treatment system (e.g., the systems 100 or 110) in a generally similar or identical manner to mechanically engage and dislodge clot material within an implanted stent or other implant.

In the illustrated embodiment, the clot treatment device 1230 includes a plurality of interconnected struts extending between a distal end portion 1231*a* and a proximal end portion 1231*b*. More specifically, the clot treatment device 1230 can include (i) distal struts 1264 that extend from the distal end portion 1231*a* generally axially relative to a longitudinal axis L of the clot treatment device 1230, (ii) proximal struts 1266 that extend from the proximal end portion 1231*b* generally axially relative to the longitudinal axis L of the clot treatment device 1230, and (iii) bracing struts 1265 connecting the distal struts 1264 to the proximal struts 1266. The bracing struts 1265 can extend at least partially circumferentially relative to the longitudinal axis L in a middle region of the clot treatment device 1230 and can have a chevron- or ring-like pattern. In some aspects of the present technology, the bracing struts 1265 can facilitate an increased torque response of the clot treatment device 1230, while the distal and proximal struts 1264, 1266 extend generally axially to allow the clot treatment device 1230 to be advanced and retracted through an implanted stent without catching on the stent, which could potentially damage or move the stent.

Figure 13:
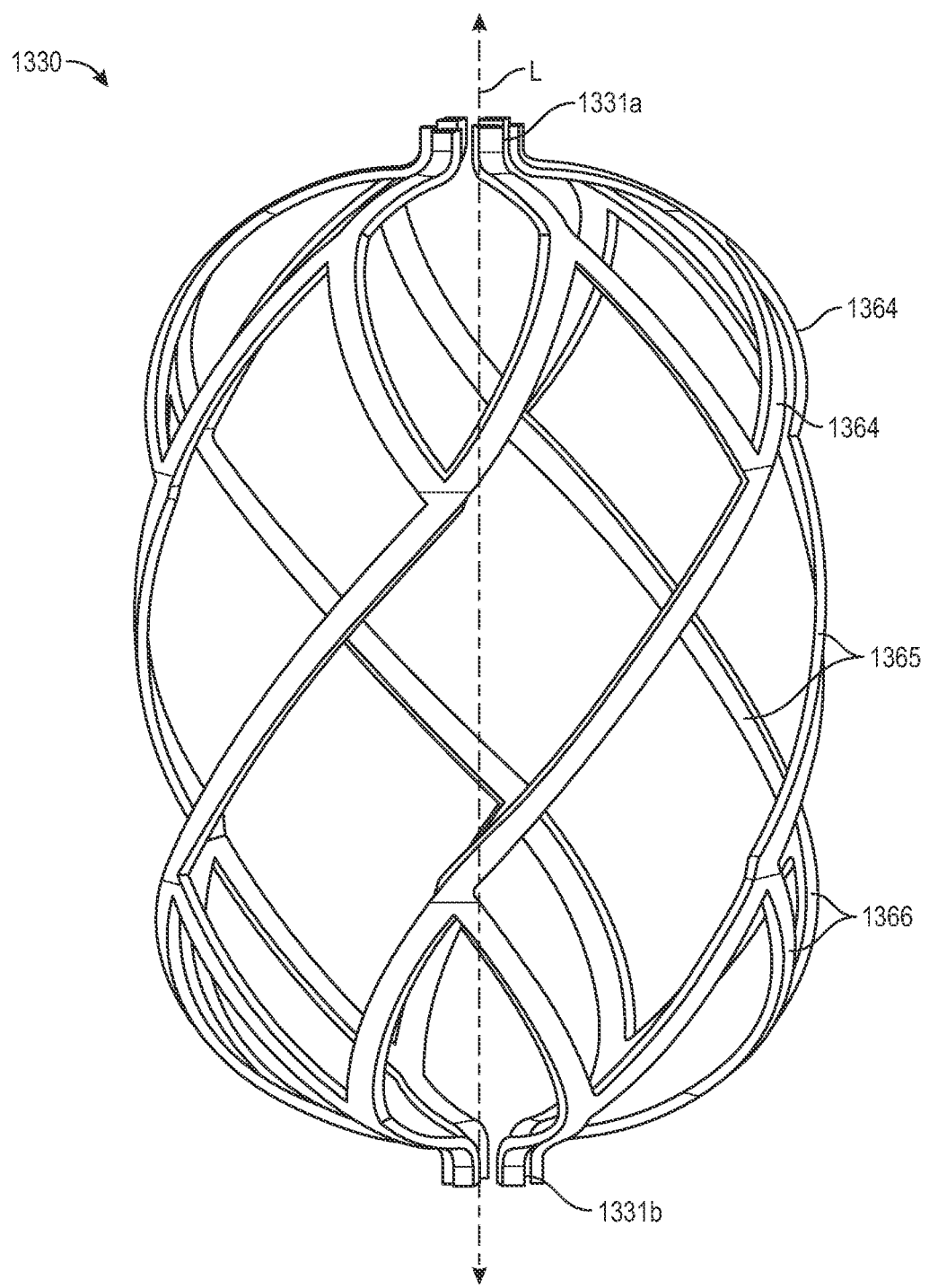
FIG. 13 is a side view of a clot treatment device in accordance with embodiments of the present technology.

FIG. 13 is a side view of a clot treatment device 1330 in accordance with embodiments of the present technology. The clot treatment device 1330 can include some features that are at least generally similar in structure and function, or identical in structure and function, to the corresponding features of the clot treatment devices 130, 1130, and/or 1230 described in detail above with reference to FIGS. 1A-12, and can be employed within a clot treatment system (e.g., the systems 100 or 1100) in a generally similar or identical manner to mechanically engage and dislodge clot material within an implanted stent or other implant.

In the illustrated embodiment, the clot treatment device 1330 includes a plurality of interconnected struts extending between a distal end portion 1331*a* and a proximal end portion 1331*b*. More specifically, the clot treatment device 1330 can include (i) distal struts 1364 extending from the distal end portion 1331*a*, (ii) proximal struts 1366 extending from the proximal end portion 1331*b*, and (iii) middle struts 1365 (e.g., spanning struts, axial struts) extending between the distal and proximal struts 1364, 1366. In some embodiments, the clot treatment device 1330 includes fewer of the middle struts 1365 than the distal and proximal struts 1364, 1366, and the middle struts 1365 can be longer than the distal and proximal struts 1364, 1366. In the illustrated embodiment, the middle struts 1365 extend in a spiral or helical pattern relative to a longitudinal axis L of the clot treatment device 1330. The distal and proximal struts 1364, 1366 can have a chevron- or ring-like pattern. In some aspects of the present technology, the spiral shape of middle struts 1365 can facilitate an increased torque response of the clot treatment device 1330 while also reducing engagement of the clot treatment device 1330 with an implanted stent. In some embodiments, the clot treatment device 1330 can be rotated such that the middle struts 1365 turn away from the ends of an implanted stent (e.g., by rotating the distal and proximal end portions 1331*a-b* in opposite directions) to further reduce stent engagement.

Figure 14:
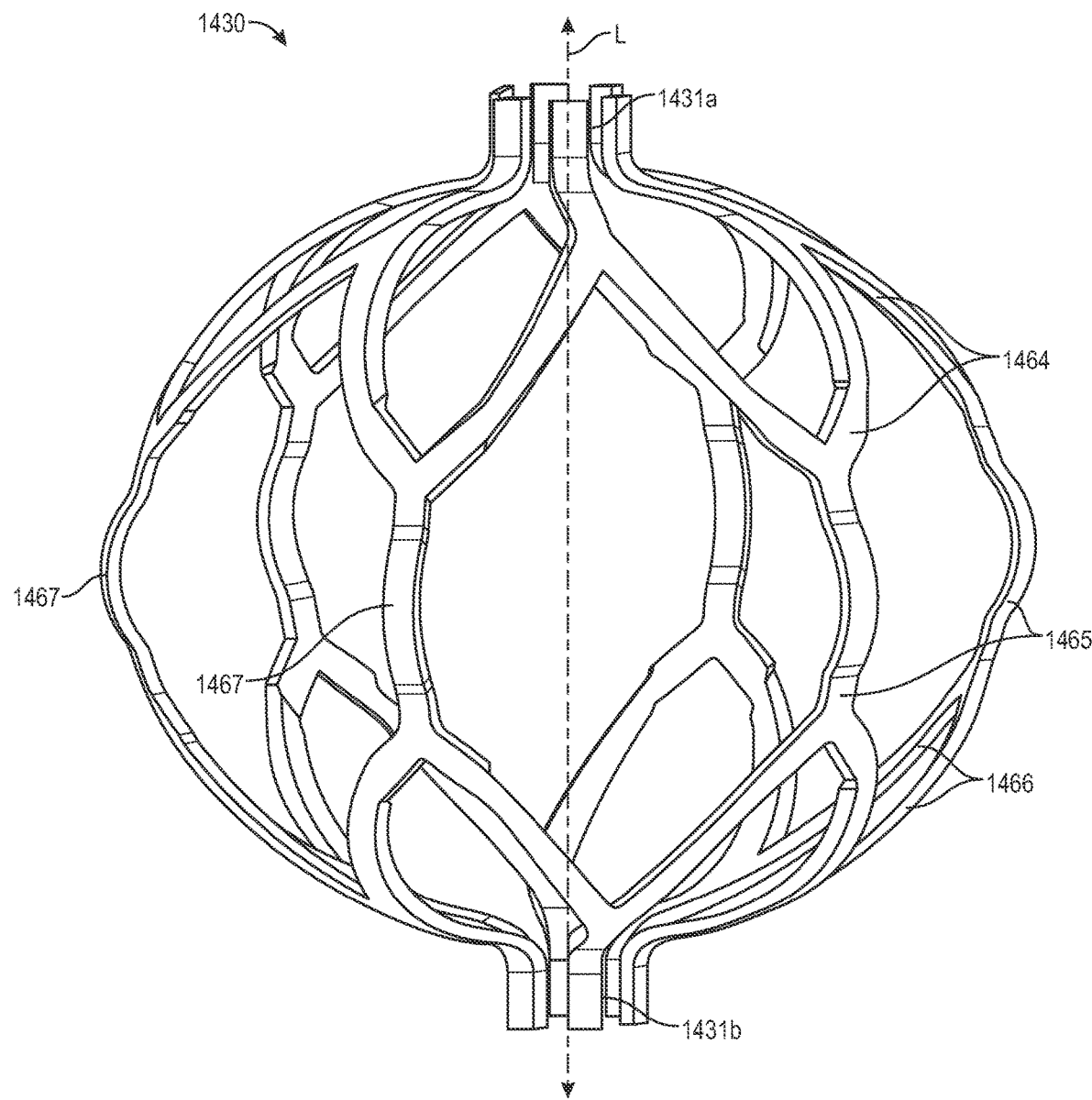
FIG. 14 is a side view of a clot treatment device in accordance with embodiments of the present technology.

FIG. 14 is a side view of a clot treatment device 1430 in accordance with embodiments of the present technology. The clot treatment device 1430 can include some features that are at least generally similar in structure and function, or identical in structure and function, to the corresponding features of the clot treatment devices 130, 1130, 1230, and/or 1330 described in detail above with reference to FIGS. 1A-13, and can be employed within a clot treatment system (e.g., the systems 100 or 1100) in a generally similar or identical manner to mechanically engage and dislodge clot material within an implanted stent or other implant.

In the illustrated embodiment, the clot treatment device 1430 includes a plurality of interconnected struts extending between a distal end portion 1431a and a proximal end portion 1431b. More specifically, the clot treatment device 1430 can include (i) distal struts 1464 extending from the distal end portion 1431a, (ii) proximal struts 1466 extending from the proximal end portion 1431b, and (iii) middle struts 1465 (e.g., spanning struts, axial struts) extending between the distal and proximal struts 1464, 1466 and generally axially relative to a longitudinal axis L of the clot treatment device 1430. In some embodiments, the clot treatment device 1430 includes fewer of the middle struts 1465 than the distal and proximal struts 1464, 1466, and the middle struts 1465 can be longer than the distal and proximal struts 1464, 1466. In some aspects of the present technology, the distal and proximal struts 1464, 1466 can facilitate an increased torque response of the clot treatment device 1430, while the axially-extending middle struts 1465 reduce engagement of the clot treatment device 1430 with an implanted stent. In some embodiments, the clot treatment device 1430 further includes bumps 1467 (e.g., radially-extending portions) on the middle struts 1465 configured to increase the radial force of the clot treatment device 1430 for, for example, engaging and dislodging the most adhered clot or other material within the implanted stent.

Figure 15:
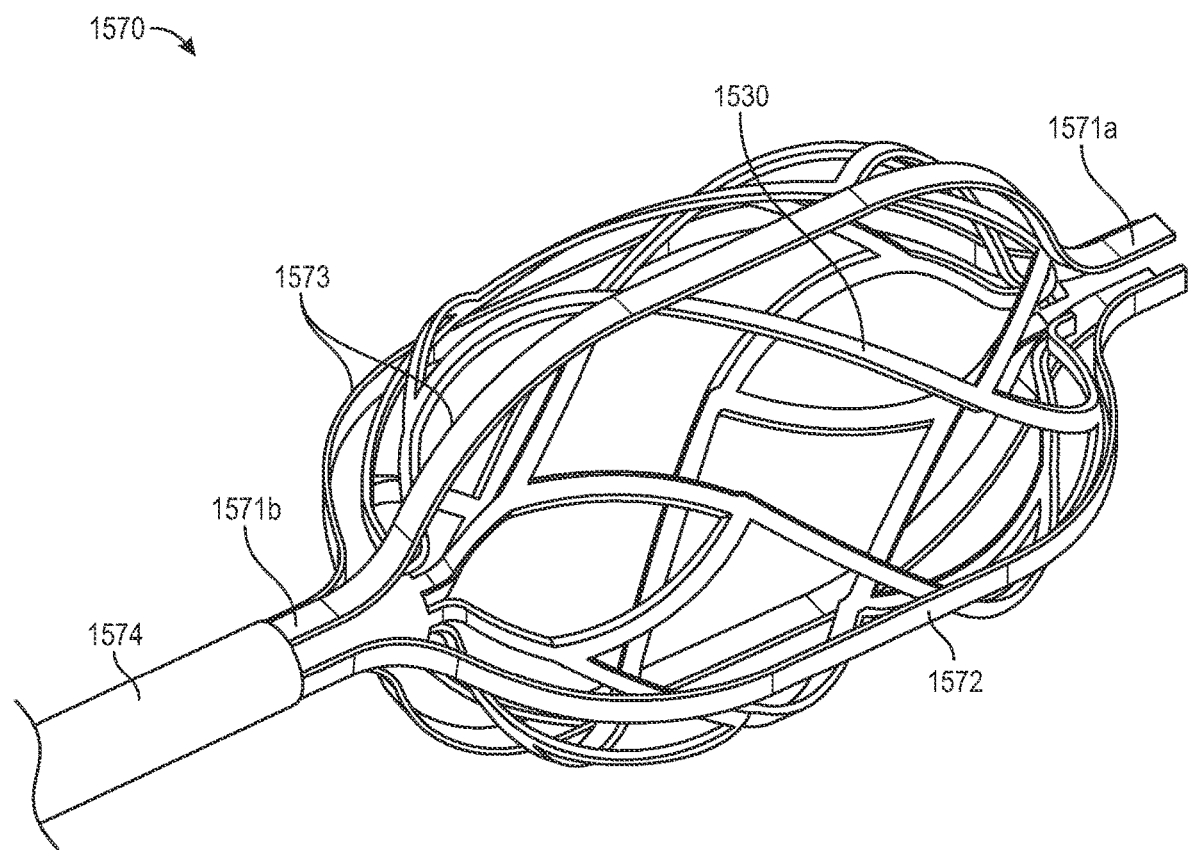
FIG. 15 is a side view of a clot treatment device in accordance with embodiments of the present technology.

FIG. 15 is a side view of a clot treatment device 1570 in accordance with embodiments of the present technology. The clot treatment device 1570 can include some features that are at least generally similar in structure and function, or identical in structure and function, to the corresponding features of the clot treatment devices 130, 1130, 1230, 1330, and/or 1430 described in detail above with reference to FIGS. 1A-14, and can be employed within a clot treatment system (e.g., the systems 100 or 1100) in a generally similar or identical manner to mechanically engage and dislodge clot material within an implanted stent or other implant.

In the illustrated embodiment, the clot treatment device 1570 includes an inner clot treatment device 1530 and an outer clot treatment device 1572 (e.g., a stent protection element) that houses the inner clot treatment device 1530. The inner clot treatment device 1530 can be identical to any of the clot treatment devices 130, 1130, 1230, 1330, and/or 1430 described in detail above with reference to FIGS. 1A-14 and, in the illustrated embodiment, is identical to the clot treatment devices 1330 of FIG. 13. In the illustrated embodiment, the outer clot treatment device 1572 includes a distal end portion 1571a, a proximal end portion 1571b, and a plurality of struts 1573 extending (e.g., axially) between the distal and proximal end portions 1571a-b. The proximal end portion 1571b can be coupled to an elongate member 1574, and the inner clot treatment device 1530 can be advanceable through a lumen of the elongate member 1574 or fixed relative to the elongate member 1574. In some embodiments, the outer clot treatment device 1572 is configured to be radially expanded and/or compressed via movement of the inner clot treatment device 1530. For example, the outer clot treatment device 1572 can be formed of nitinol or another relatively flexible material such that expansion (e.g., via any of the handles described above) of the inner clot treatment device 1530 also expands the outer clot treatment device 1572.

During a clot treatment procedure, the outer clot treatment device 1572 can directly engage an implanted stent while the inner clot treatment device 1530 is rotated therein and/or while the clot treatment device 1570 is translated distally and/or proximally within the implanted stent. Moreover, the outer clot treatment device 1572 can be fixed so that it does not rotate with the inner clot treatment device 1530 via its connection to the elongate member 1574. In some aspects of the present technology, the outer clot treatment device 1572 can partially or fully protect the implanted stent from being directly contacted by the inner clot treatment device 1530—thereby reducing stent engagement that might damage or disrupt the stent. Further, the outer clot treatment device 1572 can still provide a large inner diameter that allows the inner clot treatment device 1530 to engage and disrupt clot or other material adhered to the stent.

Figure 16A:
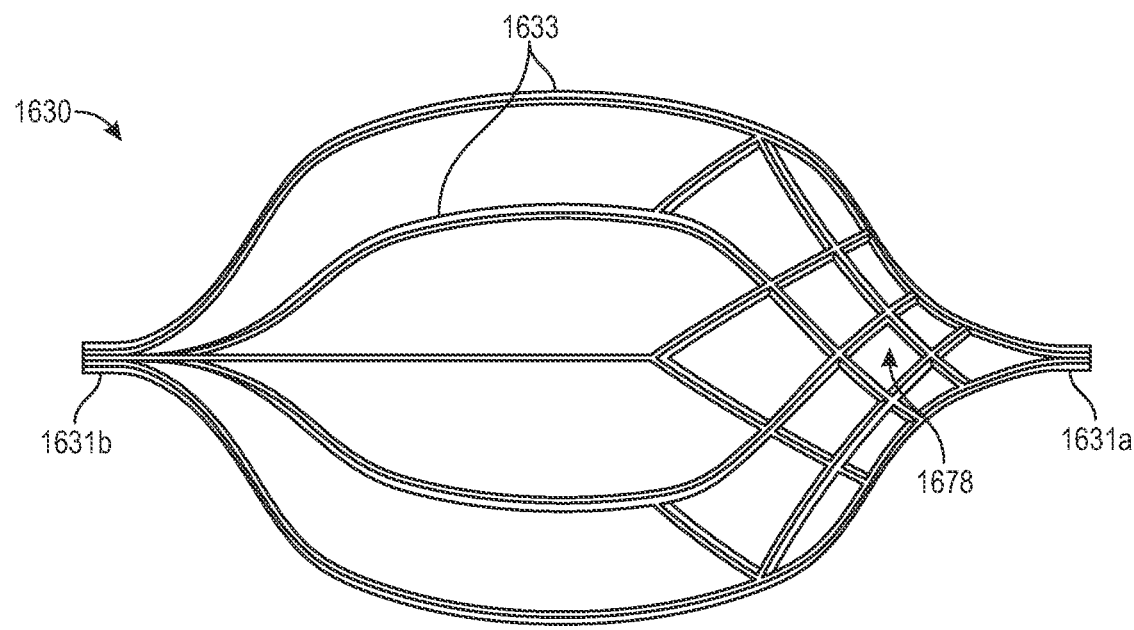
FIGS. 16A-16C are side views of a clot treatment device in accordance with embodiments of the present technology.
Figure 16B:
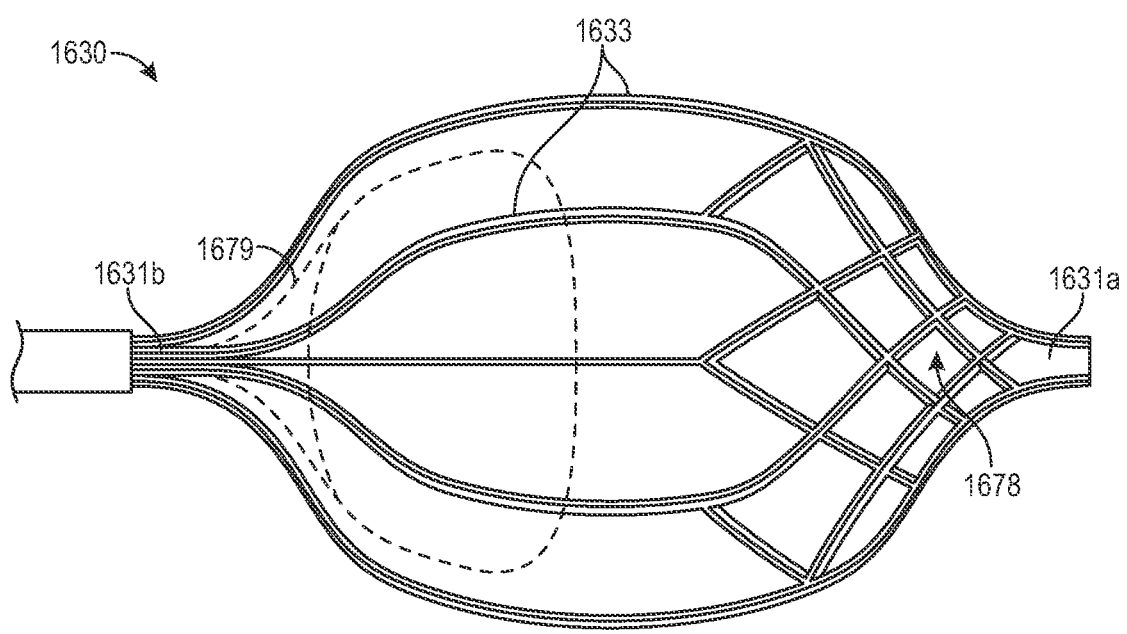
Figure 16C:
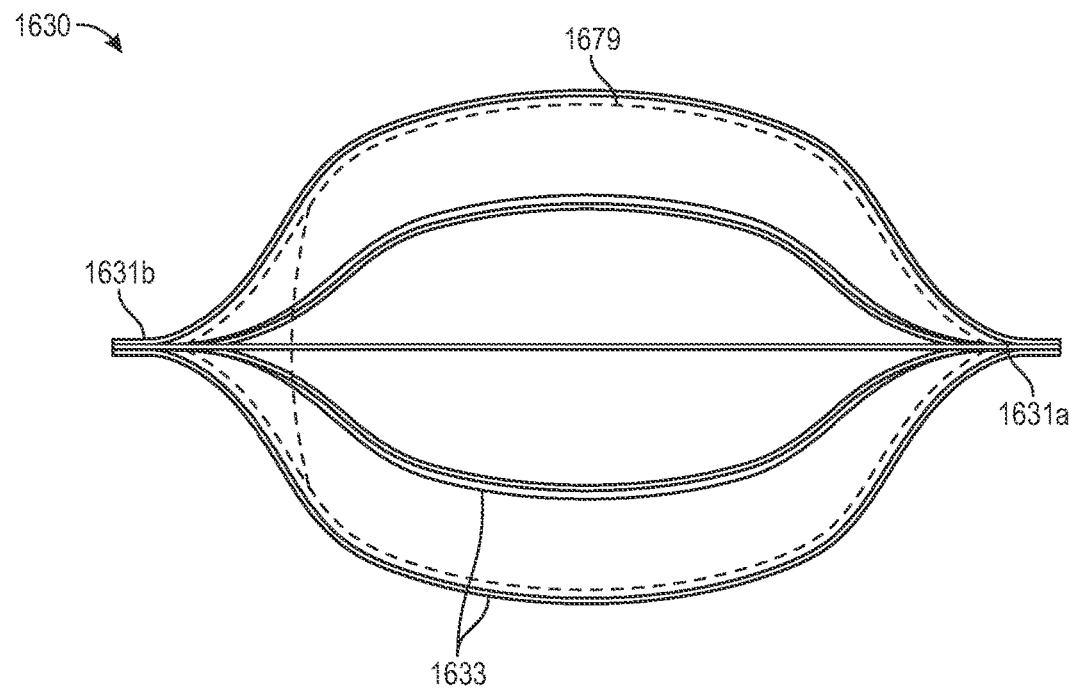

FIGS. 16A-16C are side views of a clot treatment device 1630 in accordance with embodiments of the present technology. The clot treatment device 1630 can include some features that are at least generally similar in structure and function, or identical in structure and function, to the corresponding features of the clot treatment devices 130, 1130, 1230, 1330, 1430, and/or 1530 described in detail above with reference to FIGS. 1A-15, and can be employed within a clot treatment system (e.g., the systems 100 or 1100) in a generally similar or identical manner to mechanically engage and dislodge clot material within an implanted stent or other implant.

Referring to FIGS. 16A-16C together, the clot treatment device 1630 includes a plurality of struts 1633 extending between a distal end portion 1631a and a proximal end portion 1631b. Referring to FIG. 16A, the clot treatment device 1630 can include a distal clot collection member 1678. The clot collection member 1678 can comprise a plurality of dense cells formed by the struts 1633, or a separate member attached to the struts 1633, such as a bag (e.g., a mesh bag, a short nitinol bag, and/or the like). In some aspects of the present technology, the clot collection member 1678 can capture clot material as the clot treatment device 1630 is moved (e.g., translated, rotated) within an implanted stent. Referring to FIG. 16B, in some embodiments the clot treatment device 1630 can further include an expandable member 1679, such as a balloon, positioned radially within the struts 1633. The expandable member 1679 can be expanded to force the struts 1633 radially outward to, for example, provide additional support for dislodging adherent clot material from an implanted stent. In the illustrated embodiment, the expandable member 1679 is positioned only within a proximal portion of the clot treatment device 1630. In other embodiments, the expandable member 1679 can be positioned along the entire length of the clot treatment device 1630, or in a different portion of the clot treatment device 1630 (e.g., a distal portion). For example, as shown in FIG. 16C, the expandable member 1679 is positioned along an entire length of the clot treatment device 1630. Moreover, in the illustrated embodiment the clot collection member 1678 is omitted.

Figure 17A:
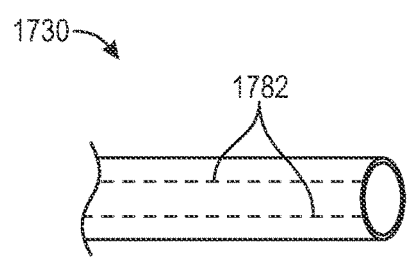
FIGS. 17A and 17B are side views of a distal portion of a stent cleaning system in accordance with embodiments of the present technology.
Figure 17B:
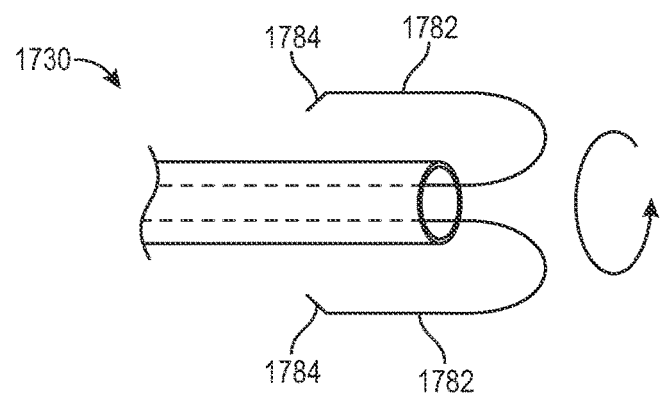

FIGS. 17A and 17B are side views of a distal portion of a stent cleaning system 1700 ("system 1700") in accordance with embodiments of the present technology. Referring to FIGS. 17A and 17B together, the system 1700 includes an elongate member 1706 and a clot treatment device 1780 advanceable through the elongate member 1706. The clot treatment device 1780 includes a pair of expandable arms 1782 that can be formed of nitinol or similar materials. In FIG. 17A, the clot treatment device 1780 is constrained within the elongate member 1706 such that the arms 1782 extend generally linearly through the lumen of the elongate member 1706. FIG. 17B illustrates the clot treatment device 1780 after advancement of the clot treatment device 1780 from the elongate member 1706. In the illustrated embodiment, the arms 1782 are configured to expand radially and curve back proximally (e.g., each forming a U-like shape) when unconstrained by the elongate member 1706. The clot treatment device 1780 can be deployed within an implanted stent and rotated to engage and dislodge (e.g., cut) clot or other material adhered to the stent. In some embodiments, the arms 1782 can each have a tapered end portion 1784 configured to inhibit the arms 1782 from interacting with or damaging the stent.

Figure 18:
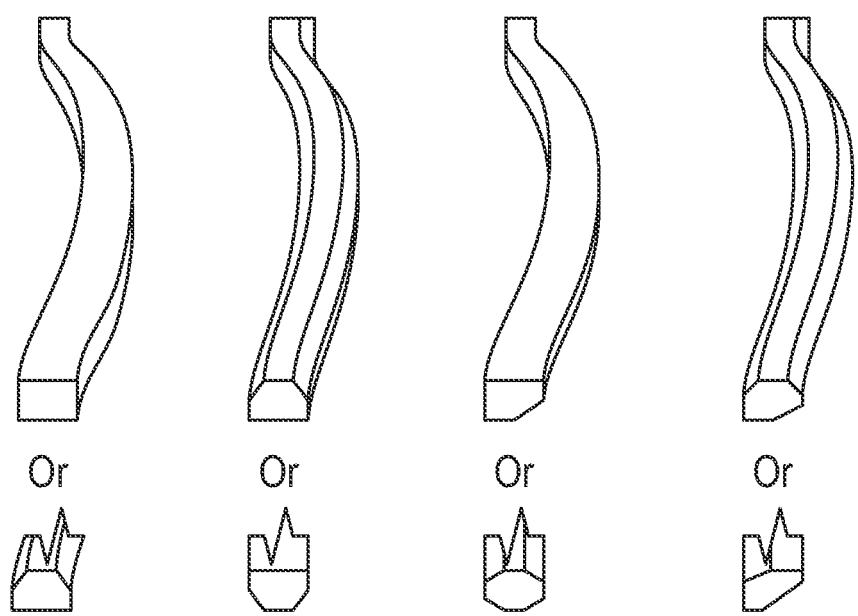
FIG. 18 illustrates several different chamfers that can be used in a clot treatment device in accordance with embodiments of the present technology.
Figure 19:
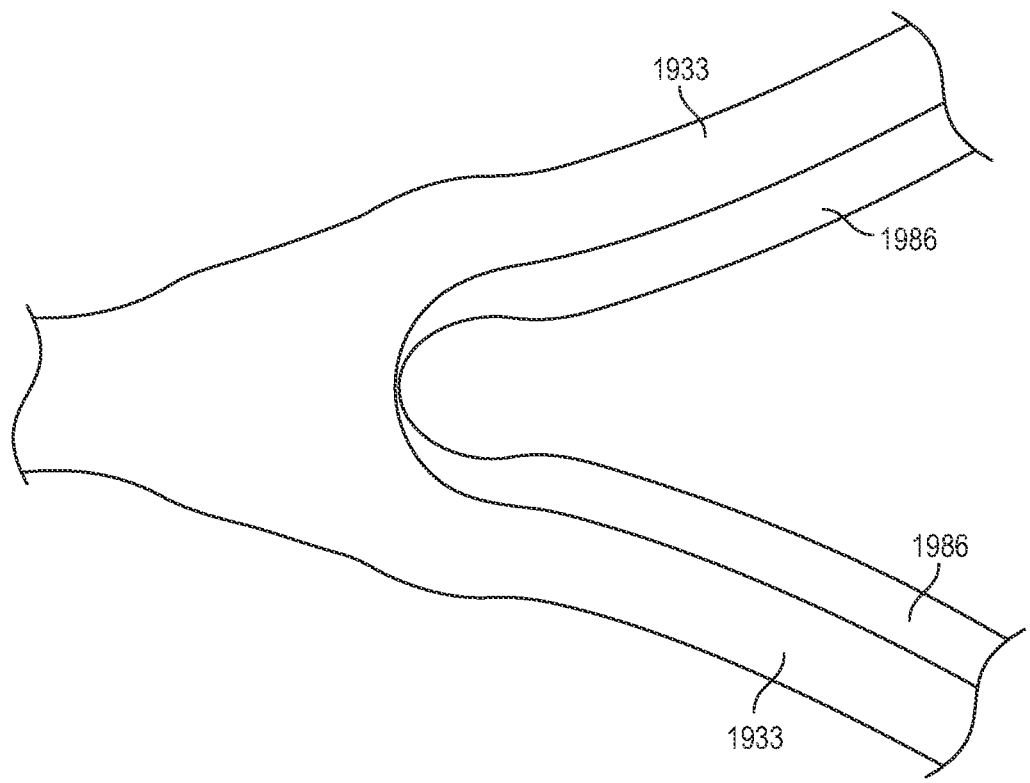
FIG. 19 is an enlarged side view of a pair of struts of a clot treatment device in accordance with embodiments of the present technology.

In any of the embodiments described above with reference to FIGS. 1A-17B, a clot treatment device can include struts with a chamfer or angle to improve the ability of the clot treatment device to cut through adhered clot surfaces. At the same time, such a chamfer can allow the struts to be made relatively thick to increase their radial force. More specifically, for example, FIG. 18 illustrates several struts having different chamfers that can be used in a clot treatment device in accordance with embodiments of the present technology. FIG. 19 is and enlarged side view of a pair of struts 1933 of a clot treatment device each having a chamfered edge 1986 in accordance with embodiments of the present technology.

In other embodiments, a handle in accordance with the present technology can have other configurations for (i) driving a pair of elongate members (e.g., the elongate members 102, 104 of FIGS. 1A-1C) relative to one another to radially expand/compress a clot treatment device (e.g., the clot treatment device 130) and/or (ii) rotating the clot treatment device. FIGS. 21-27, for example, illustrate handles and/or handle components in accordance with embodiments of the present technology that can be incorporated into the system 100, the system 1100, and/or another suitable system instead of or in addition to the handle 110 and/or the handle 1110. The various handles can include some features that are at least generally similar in structure and function, or identical in structure and function, to the corresponding features of one another, the handle 110 described in detail above with reference to FIGS. 1A-C and 5, and/or the handle 1110 described in detail above with reference to FIGS. 11A-11C, and can operate in a generally similar or identical manner to one another, the handle 110, and/or the handle 1110. Moreover, although frequently described in the context of manipulating the clot treatment device 130 shown in FIGS. 1A-1C, the handles of the present technology can be used to manipulate/control any of the clot treatment devices of the present technology.

Figure 20:
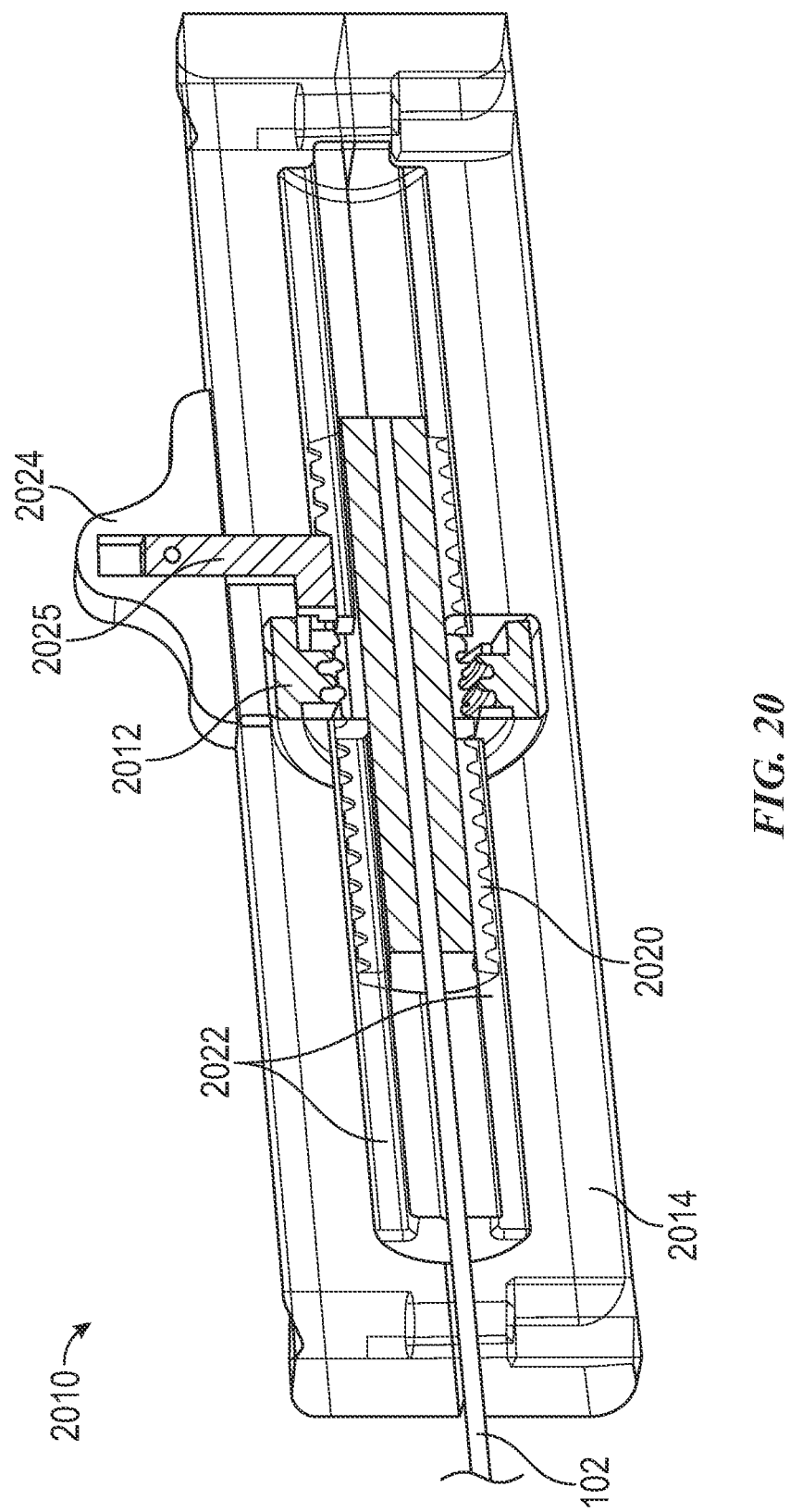
FIG. 20 is a side cross-sectional view of a handle in accordance with additional embodiments of the present technology that can be used in the system of FIG. 1A.

FIG. 20, for example, is a side cross-sectional view of a handle 2010 in accordance with embodiments of the present technology that can be incorporated into (e.g., used in) the system 100 (e.g., instead of the handle 110). In the illustrated embodiment, the handle 2010 includes a housing 2014 and a leadscrew 2020 movably positioned within the housing 2014 and constrained by/over one or more guiderails 2022 (e.g., a pair of the guiderails 2022). The leadscrew 2020 can have a threaded outer surface configured to mate with a threaded inner surface of an actuator 2012, which extends out of the housing 2014 such that the actuator 2012 is accessible outside the housing 2014 by a user of the handle 2010 (e.g., a physician). The inner elongate member 102 can be fixed to the leadscrew 2020, and the middle elongate member 104 (not shown) can be fixed to the housing 2014. Accordingly, actuation (e.g., rotation) of the actuator 2012 can drive the leadscrew 2020 proximally/distally through the housing 2014 to drive the inner elongate member 102 relative to the middle elongate member 104 to radially compress/expand the clot treatment device 130 as shown in FIGS. 6A and 6B.

In the illustrated embodiment, the handle 2010 further includes a lock mechanism 2024 coupled to the housing 2014. The lock mechanism 2024 can include a lock member 2025 configured to engage the leadscrew 2020 and/or the actuator 2012 to inhibit movement of the leadscrew 2020 through the housing 2014. In the illustrated embodiment, the lock mechanism 2024 is in a locked position in which the lock member 2025 engages the actuator 2012 to inhibit movement of the actuator 2012 and the leadscrew 2020. In some embodiments, the user can actuate (e.g., push, translate, rotate, depress) the lock mechanism 2024 to withdraw the lock member 2025 away from the actuator 2012 to allow the leadscrew 2020 to move through the housing 2014. Accordingly, with additional reference to FIGS. 6A and 6B, the user can selectively engage the lock mechanism 2024 to lock the clot treatment device 130 in the first position, the second position, or and/or another position.

Figure 21:
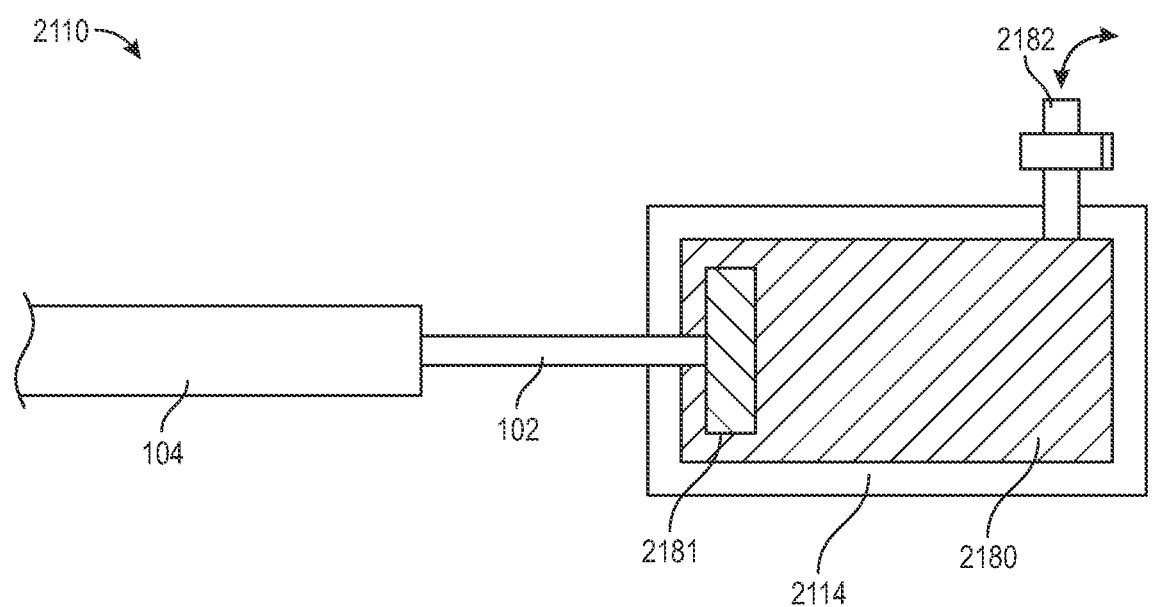
FIG. 21 is a side cross-sectional view of a handle in accordance with additional embodiments of the present technology that can be used in the system of FIG. 1A.

FIG. 21 is a side cross-sectional view of a handle 2110 in accordance with additional embodiments of the present technology that can be incorporated into the system 100 (e.g., instead of the handle 110). In the illustrated embodiment, the handle 2110 includes a housing 2114 containing a working fluid 2180. A fluid port 2182 is coupled to the housing 2114 and configured to remove/insert the working fluid 2180 into the housing 2114 via a fluid control system (not shown). The inner elongate member 102 can be coupled to a flange 2181 positioned within the housing 2114 and configured to sealingly engage the housing 2114 such that the working fluid 2180 is positioned only between the flange 2181 and the fluid port 2182. Accordingly, in operation, the working fluid 2180 can be pumped into/out of the housing 2114 to drive the flange 2181 distally/proximally through the housing 2114 to drive the inner elongate member 102 relative to the middle elongate member 104 to radially expand/compress the clot treatment device 130 as shown in FIGS. 3A and 3B. Therefore, in some aspects of the present technology the handle 2110 can be a pneumatically and/or hydraulically operated handle.

Figure 22:
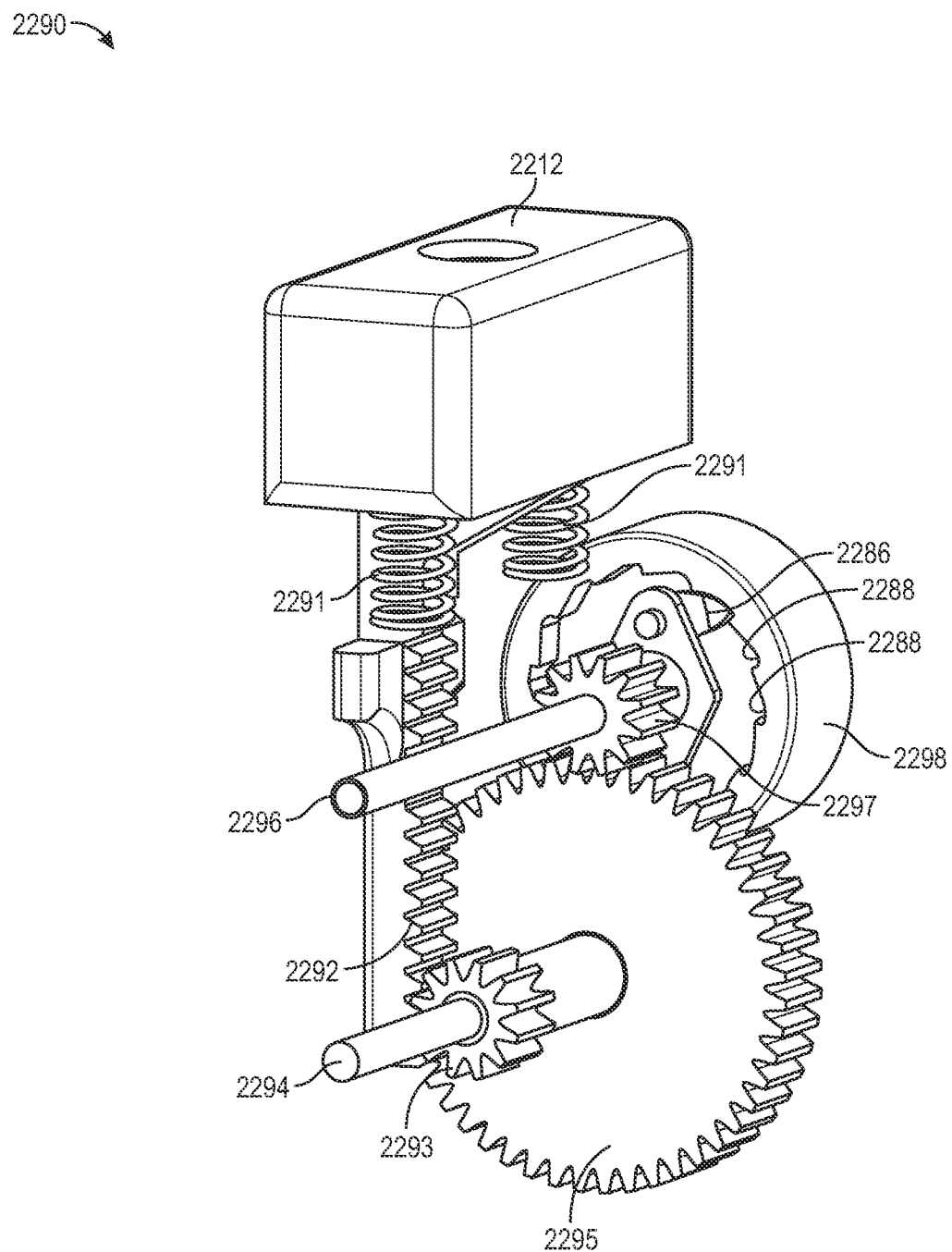
FIG. 22 is a side cross-sectional view of an actuation mechanism of a handle in accordance with embodiments of the present technology that can be used in the system of FIG. 1A.

FIG. 22 is an isometric view of an actuation mechanism 2290 of a handle that can be incorporated into the system 100 in accordance with embodiments of the present technology. In the illustrated embodiment, the actuation mechanism 2290 includes an actuator 2212 that is operably coupled to a housing or other component of the handle (not shown) via one or more biasing members 2291, such as coil springs. The actuator 2212 can be operably coupled to (e.g., integrally formed with) a gear rack 2292 having a plurality of teeth configured to engage a first gear 2293 mounted on a first shaft 2294. A second gear 2295 can be mounted on the first shaft 2294, coupled to the first gear 2293, and configured to engage a third gear 2297 mounted on a second shaft 2296. In some embodiments, the second gear 2295 is larger than the first gear 2293. In the illustrated embodiment, the second shaft 2296 is coupled to a unidirectional ratchet mechanism 2298 including, for example, a tooth 2286 that interfaces with circumferentially disposed indents 2288 to allow only counterclockwise rotation.

Accordingly, in operation, a user can press the actuator 2212 linearly against the biasing force of the biasing members 2291 to drive the gear rack 2292 linearly relative to the first gear 2293. The movement of the gear rack 2292 rotates the first gear 2293 via the engagement of the gear rack 2292 and the first gear 2293. The rotation of the first gear 2293 rotates the coupled second gear 2295, which in turn rotates the third gear 2297 via the engagement of the second and third gears 2295, 2297. In some embodiments, the larger size of the second gear 2295 steps up the rotation speed of the first gear 2293. In some embodiments, the second gear can 2295 can be omitted and the first gear 2293 can directly engage the third gear 2297 or the first shaft 2294 can directly engage the ratchet mechanism 2298. The ratchet mechanism 2298 inhibits or even prevents the third gear 2297 from rotating in multiple directions, such as when the biasing members 2291 return the actuator 2212 to an initial position after being depressed. Accordingly, the actuation mechanism 2290 translates the linear motion of the actuator 2212 to unidirectional rotation of the ratchet mechanism 2298 and the third gear 2297. The ratchet mechanism 2298 and/or the third gear 2297 can be coupled directly to one or both of the elongate members 102, 104 (FIGS. 1A-1C) such that the actuation mechanism 2290 is configured to rotate the elongate members 102, 104, or the ratchet mechanism 2298 and/or the third gear 2297 can be coupled to a leadscrew or other device such that the actuation mechanism 2290 is configured to drive the elongate members 102, 104 relative to one another to radially expand/compress the clot treatment device 130 as shown in FIGS. 3A and 3B, as described in detail above.

Figure 23:
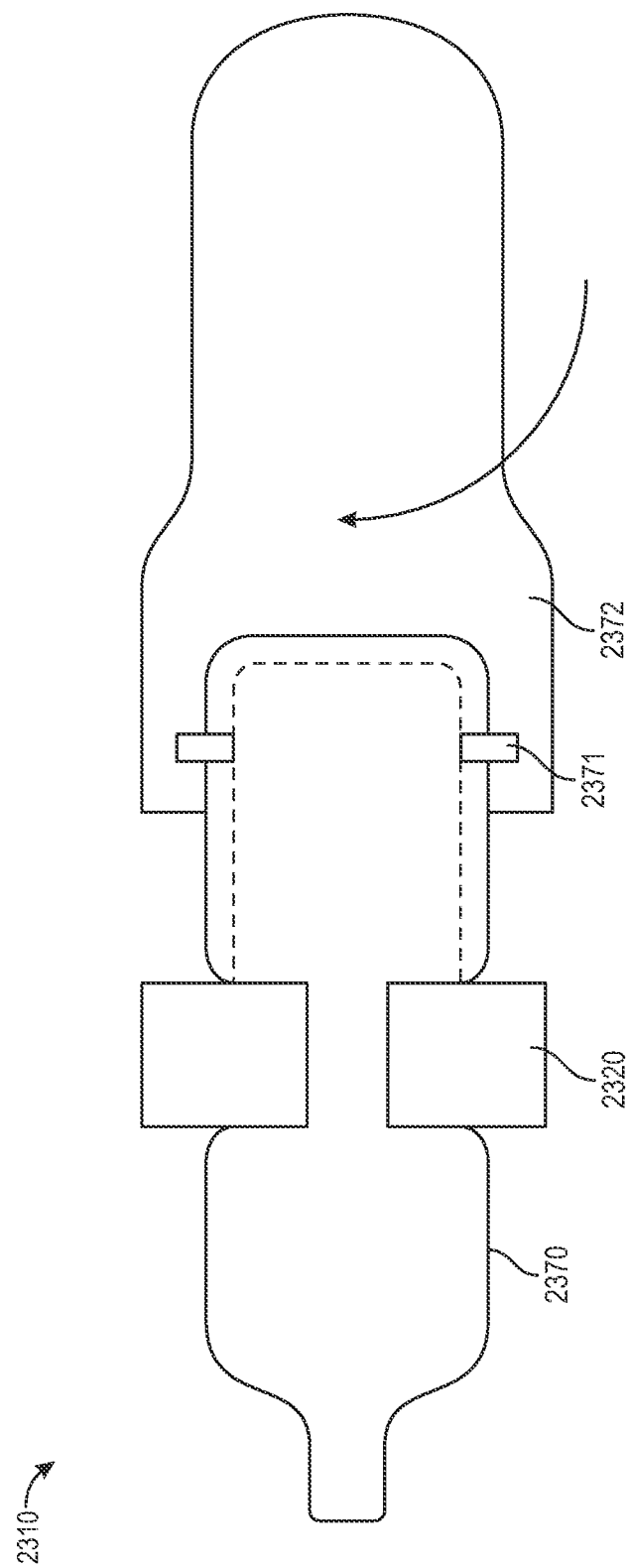
FIG. 23 is a side cross-sectional view of a handle in accordance with additional embodiments of the present technology that can be used in the system of FIG. 1A.

In some embodiments, a handle coupled to a clot treatment device can include one or more features for inhibiting or even preventing over expansion and/or over torquing of the clot treatment device. FIG. 23, for example, is a side view of a handle 2310 in accordance with additional embodiments of the present technology that can be incorporated into the system 100 (e.g., instead of the handle 110). In the illustrated embodiment, the handle 2310 includes a distal handle portion 2370 and a proximal handle portion 2372. The distal handle portion 2370 can be coupled to a leadscrew 2320 that is coupled to one of the elongate members 102, 104 (e.g., the inner elongate member 102). In the illustrated embodiment, the distal handle portion 2370 is coupled to the proximal handle portion 2372 via a plurality of balls 2371, such as spring-loaded ball bearings, positioned in corresponding detents formed between the distal and proximal handle portions 2370, 2372. Accordingly, in operation, rotation of the proximal handle portion 2372 below a predetermined torque level determined by the balls 2371 and associated detents rotates the distal handle portion 2370 and the leadscrew 2320 to advance one of the elongate members 102, 104 (e.g., the inner elongate member 102) relative to the other one of the elongate members 102, 104 and radially compress/expand the attached clot treatment device 130. However, rotation of the proximal handle portion 2372 above the predetermined torque level (e.g., when a user turns the proximal handle portion 2372 too fast and/or continues to torque the proximal handle portion 2372 when the clot treatment device 130 is significantly engaged with an implant) will cause the balls 2371 to slip from the detents such that the proximal handle portion 2372 rotates relative to the distal handle portion 2370 without rotating the distal handle portion 2370. In this manner, the handle 2310 is configured to maintain a torque level of the clot treatment device 130 and associated force on an implant below a predetermined level.

In other embodiments, some or all of the balls 2371 and corresponding detents can be replaced with other mechanisms for inhibiting over torquing of the clot treatment device 130. For example, some or all of the balls 2371 can be replaced with pairs of magnets including a first one of the pair coupled to the distal handle portion 2370 and a second one of the pair coupled to the proximal handle portion 2372. The magnets can be selected such that, when the handle 2310 is over torqued, the pairs of magnets disengage (e.g., shear apart) from one another to permit the proximal handle portion 2372 to rotate relative to the distal handle portion 2370 without rotating the distal handle portion 2370.

Figure 24:
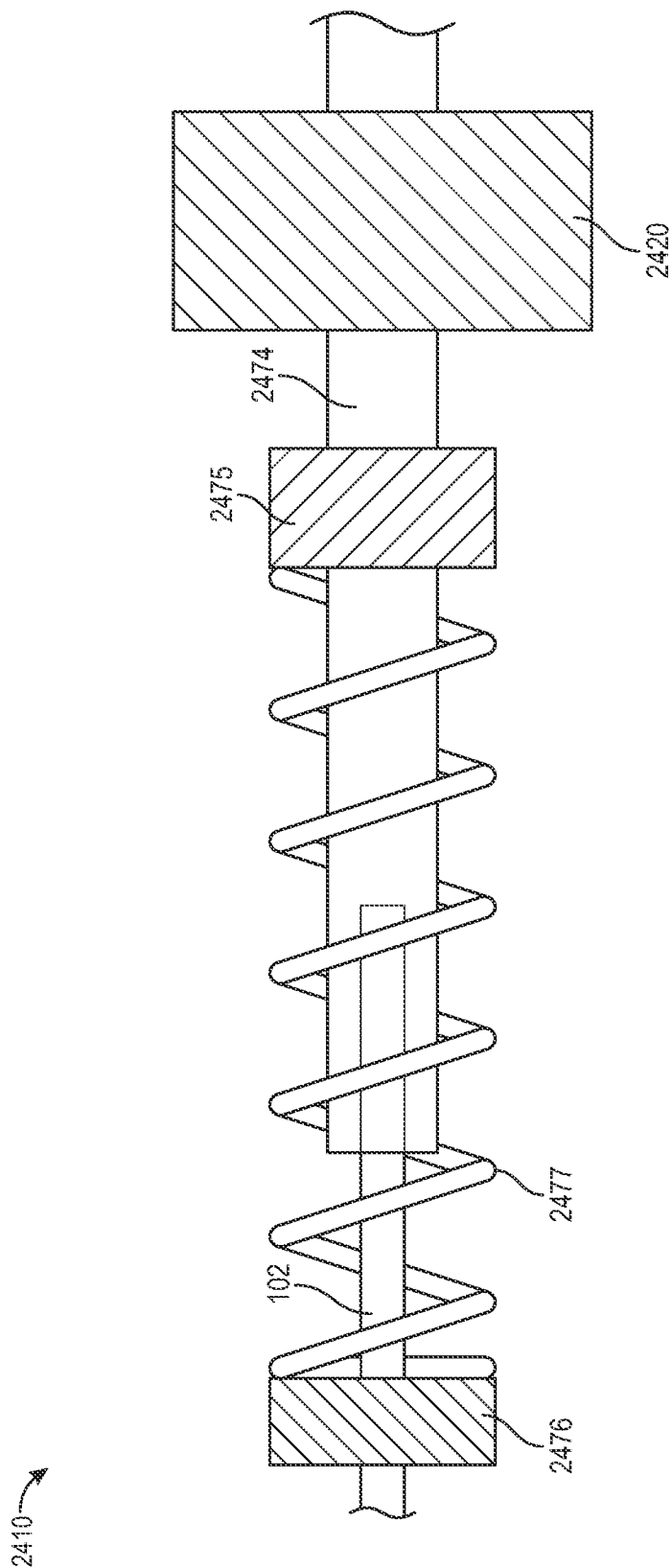
FIG. 24 is a side cross-sectional view of a handle in accordance with additional embodiments of the present technology that can be used in the system of FIG. 1A.

FIG. 24 is a side view of a handle 2410 in accordance with additional embodiments of the present technology that can be incorporated into the system 100 (e.g., instead of the handle 110). In the illustrated embodiment, the handle 2410 includes a leadscrew 2420 coupled to an intermediary shaft 2474 having a first stop 2475. Rotation of the leadscrew 2420 in a first direction can drive the intermediary shaft 2474 to translate distally, and rotation of the leadscrew 2420 in a second direction can drive the intermediary shaft 2474 to translate proximally. In the illustrated embodiment, the inner elongate member 102 is configured to at least partially telescope within the intermediary shaft 2474 and includes a second stop 2476. A biasing member 2477 (e.g., a coil spring) can extend between the first stop 2475 and the second stop 2476 to couple the inner elongate member 102 to the intermediary shaft 2474. In operation, when the intermediary shaft 2474 is driven proximally via the leadscrew 2420, the biasing member 2477 pulls the inner elongate member 102 proximally to radially expand the clot treatment device 130. However, the proximal movement also forces the biasing member 2477 to elongate—reducing the proximal movement of the inner elongate member 102 compared to, for example, embodiments where the inner elongate member 102 is directly coupled to the leadscrew 2420. Accordingly, in some aspects of the present technology the biasing member 2477 can limit the radial expansion of the clot treatment device 130 to inhibit over expansion that may damage an implant.

Figure 25A:
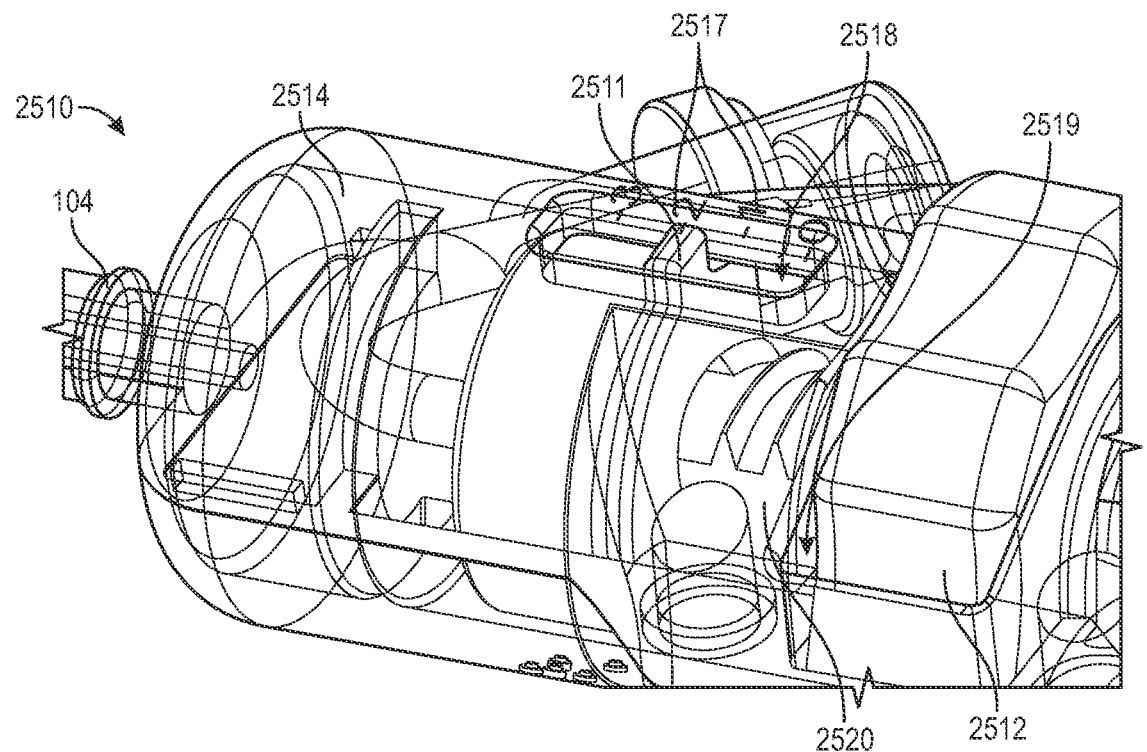
FIGS. 25A-25C are an enlarged perspective view, an enlarged side view, and an enlarged cross-sectional side view, respectively, of a handle in accordance with additional embodiments of the present technology that can be used in the system of FIG. 1A.
Figure 25B:
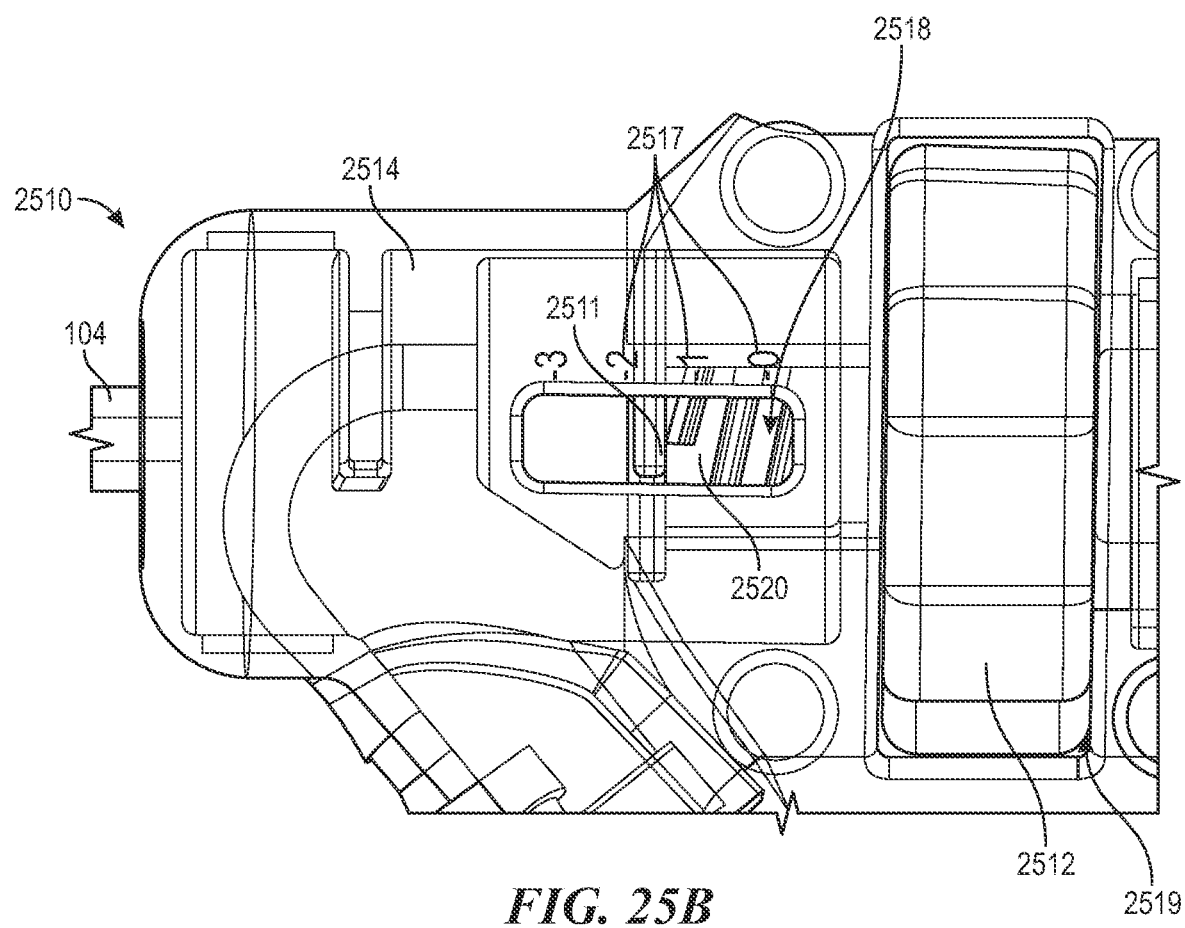
Figure 25C:
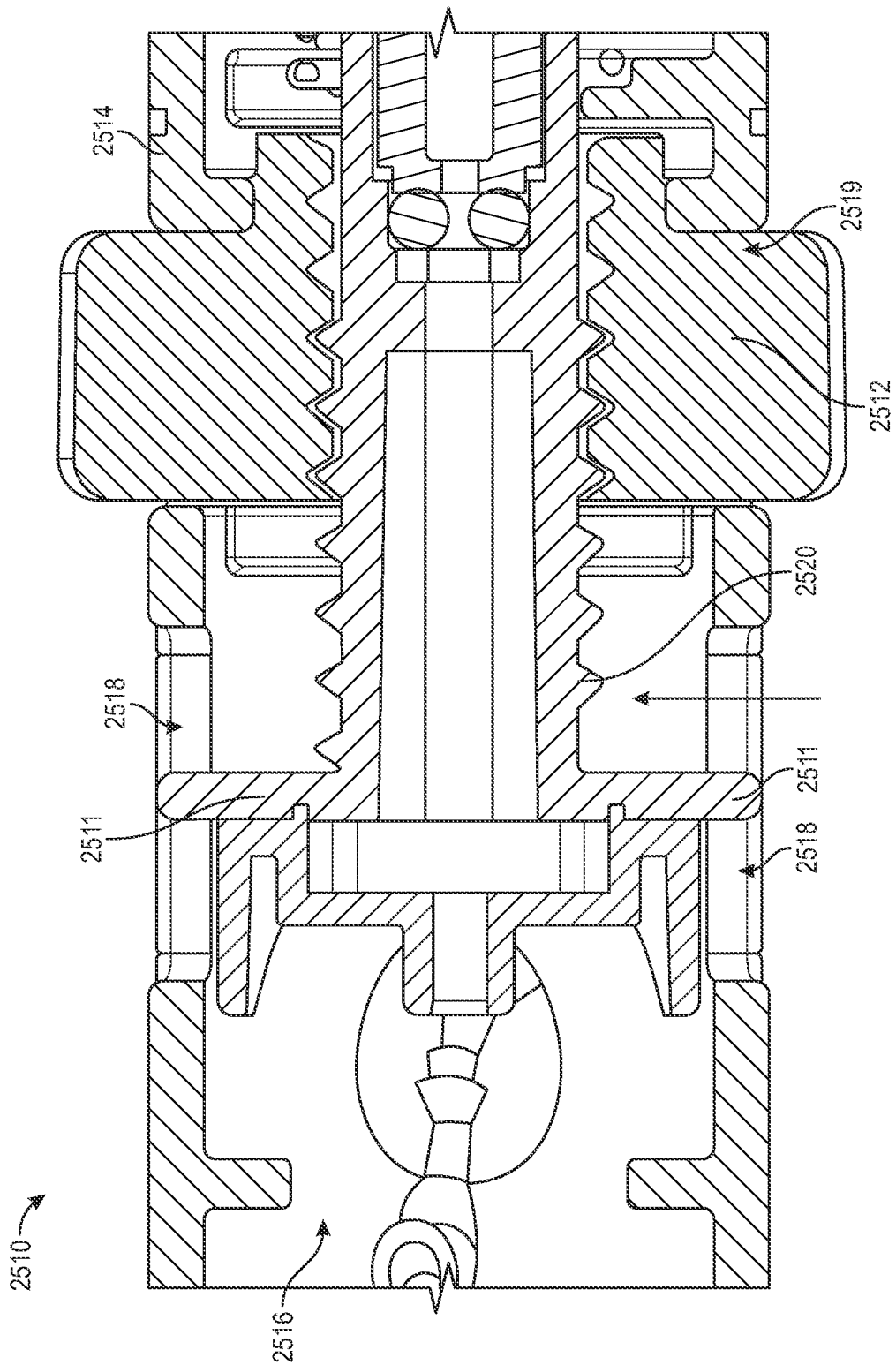

FIGS. 25A-25C are an enlarged perspective view, an enlarged side view, and an enlarged cross-sectional side view, respectively, of a handle 2510 in accordance with additional embodiments of the present technology that can be incorporated into the system 100 (e.g., instead of the handle 110). Referring to FIGS. 25A-25C together, in the illustrated embodiment, the handle 2510 includes a housing 2514 (shown as partially transparent in FIGS. 25A and 25B for clarity) defining an internal chamber or lumen 2516 (FIG. 25C). The middle elongate member 104 can be fixedly coupled to the housing 2514. The inner elongate member 102 (not shown; FIGS. 1A-1C) can extend through the lumen of the middle elongate member 104 into the lumen 2516 of the housing 2514. The handle 2510 can further comprise a leadscrew 2520 attached to the inner elongate member 102 and an actuator 2512 (e.g., a rotatable knob). The leadscrew 2520 is movably positioned within the lumen 2516 and can have a threaded outer surface configured to mate with a threaded inner surface of the actuator 2512. The actuator 112 can extend out of the housing 2514 from one or more first openings 2519 therein (e.g., a pair of openings on opposing sides of the housing 2514) such that the actuator 2512 is accessible outside the housing 2514 by a user of the handle 2510 (e.g., a physician). In operation, the actuator 2512 can be rotated relative to the housing 2514 to drive the leadscrew 2520 proximally and/or distally through the housing 2514 to thereby drive the attached inner elongate member 102 to translate relative to the middle elongate member 104 and thereby radially expand/collapse the clot treatment device 130.

In the illustrated embodiment, the handle 2510 further comprises an indicator 2511 coupled to the leadscrew 2520. The indicator 2511 can be coupled to (e.g., integrally formed with, rotatably mounted to) the leadscrew 2520 and can project into and/or otherwise be visible through one or more second openings 2518 (e.g., slots) in the housing 2514 (e.g., a pair of openings on opposing sides of the housing 2514). The housing 2514 can further include one or more markings 2517 (FIGS. 25A and 25B) adjacent to one or more of the second openings 2518 that indicate an amount of expansion of the clot treatment device 130 (e.g., a measurement of the radial expansion of the clot treatment device 130, a state of the clot treatment device 130, a position of the clot treatment device 130, and/or the like). For example, when the actuator 2512 is actuated to drive the inner elongate member 102 and expand/collapse the clot treatment device 130, the indicator 2511 can move with the leadscrew 2520 through and/or along the second openings 2518, and the one of the markings 2517 adjacent the indicator 2511 can indicate the amount of expansion (e.g., in millimeters). In some aspects of the present technology, combining the indicator 2511 with the leadscrew 2520 in such a manner allows to indicator 2511 to more accurately indicate the amount of radial expansion of the clot treatment device 130 because additional component attachment and manufacturing steps for forming the indicator are not needed.

Figure 26:
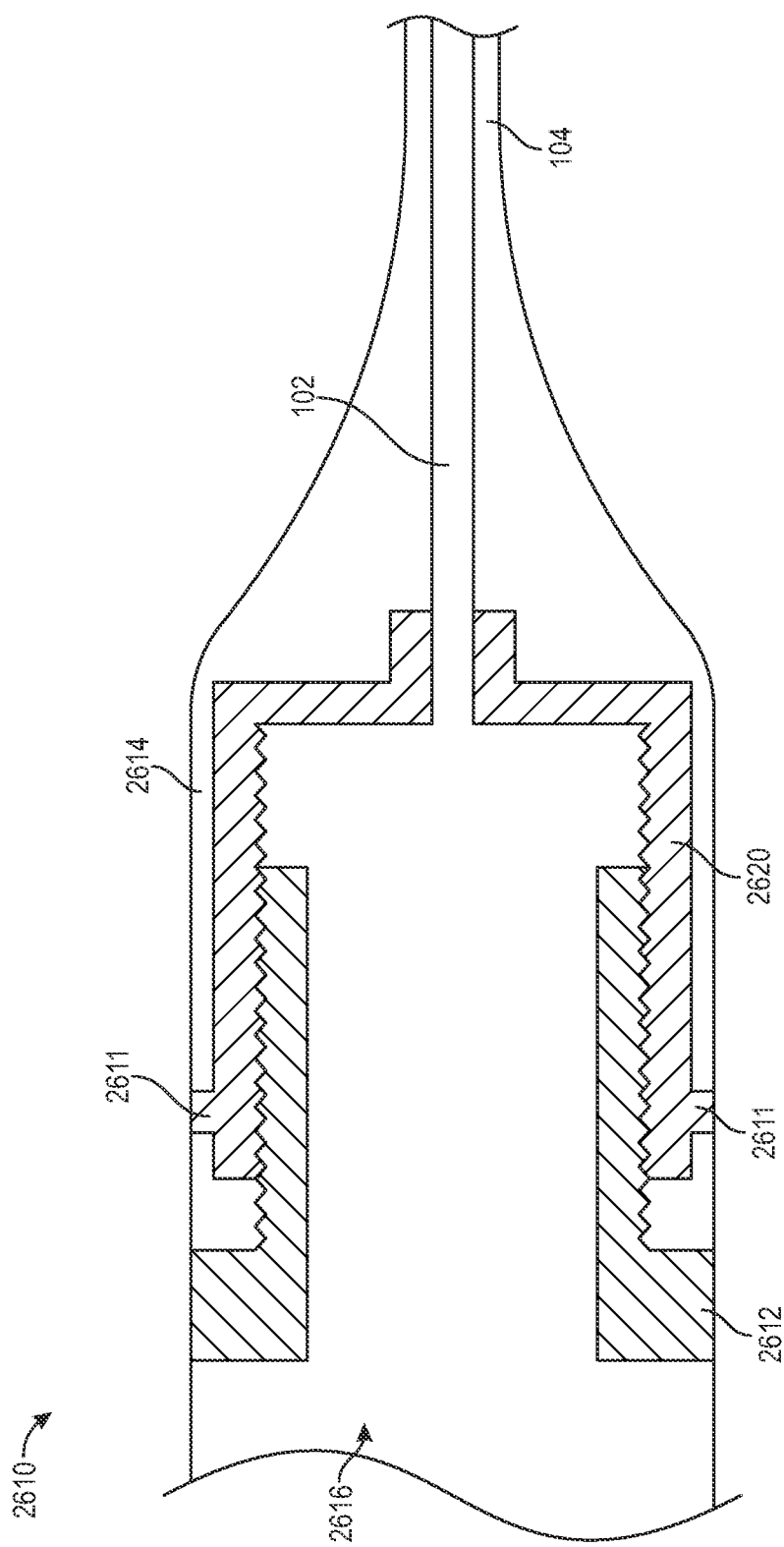
FIG. 26 is an enlarged cross-sectional side view of a handle in accordance with additional embodiments of the present technology that can be used in the system of FIG. 1A.

FIG. 26 is an enlarged cross-sectional side view of a handle 2610 in accordance with additional embodiments of the present technology that can be incorporated into the system 100 (e.g., instead of the handle 110). In the illustrated embodiment, the handle 2610 includes a housing 2614 defining an internal chamber or lumen 2616. The middle elongate member 104 can be fixedly coupled to the housing 2614. The inner elongate member 102 can extend through the lumen of the middle elongate member 104 into the lumen 2616 of the housing 2614. The handle 2610 can further comprise a leadscrew 2620 attached to the inner elongate member 102 and an actuator 2612 (e.g., a rotatable knob). The leadscrew 2620 is movably positioned within the lumen 2616 and, in the illustrated embodiment, has a threaded inner surface configured to mate with a threaded outer surface of the actuator 2612. That is, the threaded surfaces of the leadscrew 2620 and the actuator 2612 are opposite those shown in FIGS. 5 and 25A-25C. The actuator 112 can extend out of the housing 2614 such that a user can rotate the actuator 2612 relative to the housing 2614 to drive the leadscrew 2620 to proximally and/or distally through the housing 2614 to thereby drive the attached inner elongate member 102 to move relative to the middle elongate member 104 and radially expand/collapse the clot treatment device 130.

In the illustrated embodiment, the handle 2610 further comprises an indicator 2611 coupled to the leadscrew 2620 and that is visible through one or more slot/openings in the housing 2614 to provide an indication of an amount of radial expansion of the clot treatment device 130. In some aspects of the present technology, forming the outer surface of the actuator 2612 and the corresponding inner surface of the leadscrew 2620 to be threaded can allow for easier visualization of the indicator 2611, as the actuator 2612 does not block the view of the indicator 2611 and the leadscrew 2620 anywhere along the path of the leadscrew 2620.

Figure 27:
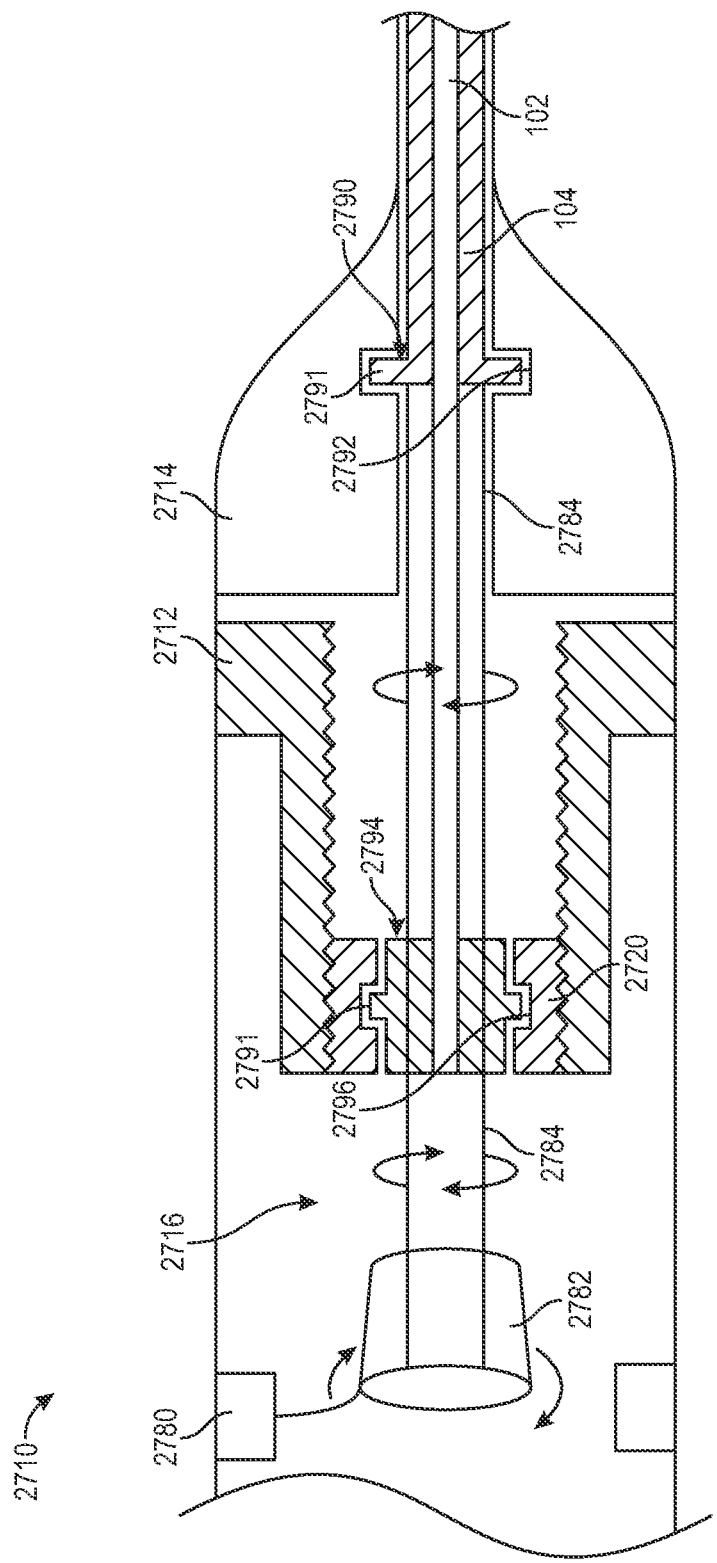
FIG. 27 is an enlarged cross-sectional side view of a handle in accordance with additional embodiments of the present technology that can be used in the system of FIG. 1A.

FIG. 27 is an enlarged cross-sectional side view of a handle 2710 in accordance with additional embodiments of the present technology that can be incorporated into the system 100 (e.g., instead of the handle 110). In the illustrated embodiment, the handle 2710 includes a housing 2714 defining an internal chamber or lumen 2716. The middle elongate member 104 can be rotatably coupled to the housing 2714 via a first adaptor 2790 (e.g., a mid-adaptor). In some embodiments, the first adaptor 2790 comprises a flange 2791 configured (e.g., shaped, sized, positioned) to be positioned in and rotatably retained within a corresponding circumferential groove or recess 2792 in the housing 2714. The inner elongate member 102 can extend through the lumen of the middle elongate member 104 into the lumen 2716 of the housing 2714. The handle 2710 can further comprise a leadscrew 2720 rotatably coupled to the inner elongate member 102 via a second adaptor 2794 and an actuator 2712 (e.g., a rotatable knob). In some embodiments, the second adaptor 2794 comprises a flange 2795 configured (e.g., shaped, sized, positioned) to be positioned in and rotatably retained within a corresponding circumferential groove or recess 2796 in the leadscrew 2720. The first adaptor 2790 can be fixedly attached to the middle elongate member 104, and the second adaptor 2794 can be fixedly attached to the inner elongate member 102 such that rotation of the elongate guide members 2784 rotates the elongate members 102, 104 together to rotate the clot treatment device 130 attached thereto. The leadscrew 2720 is movably positioned within the lumen 2716 and, in the illustrated embodiment, has a threaded outer surface configured to mate with a threaded inner surface of the actuator 2712. In operation, the actuator 2712 can be rotated relative to the housing 2714 to drive the leadscrew 2720 proximally and/or distally through the housing 2714 to thereby drive the attached inner elongate member 102 to move relative to the middle elongate member 104 and radially expand/collapse the clot treatment device 130.

In the illustrated embodiment, the handle 2710 further comprises one or more elongate guide members 2784 (e.g., torque guide pins) coupling the first adaptor 2790 to the second adaptor 2740 and a rotary motor 2782. The rotary motor 2782 can be operably coupled to an actuator 2780 (e.g., a switch, a button), a power source, a controller, and/or the like, and is actuatable to cause the rotary motor 2782 to rotate the elongate guide members 2784 to thereby rotate the first and second adaptors 2790, 2794 to thereby rotate the elongate members 102, 104. Accordingly, the handle 2710 is motorized to rotate the clot treatment device 130 (e.g., via actuation of the actuator 2780 and operation of the rotary motor 2782) while still being manually actuatable by a user (e.g., via actuation of the actuator 2712 and corresponding movement of the leadscrew 2720) to radially expand the clot treatment device 130.

In some embodiments, the rotary motor 2782 is configured to fully rotate (e.g., 360°) the clot treatment device 130 in one or both of the clockwise and counterclockwise directions. In some embodiments, the rotary motor 2782 is configured to only partially rotate the clot treatment device 130 (e.g., by about 10°-60°) in the clockwise and/or counterclockwise directions. In some embodiments, of the rotary motor 2782 (e.g., a controller operably coupled thereto) and/or other aspects of the present technology described herein may take the form of computer- or machine- or controller-executable instructions, including routines executed by a programmable computer or controller. Those skilled in the relevant art will appreciate that the technology can be practiced on computer/controller systems other than those shown and described below. The technology can be embodied in a special-purpose computer, controller or data processor that is specifically programmed, configured or constructed to perform one or more of the computer-executable instructions described below. Accordingly, the terms "computer" and "controller" as generally used herein refer to any data processor and can include Internet appliances and hand-held devices (including palm-top computers, wearable computers, cellular or mobile phones, multi-processor systems, processor-based or programmable consumer electronics, network computers, mini computers and the like). Information handled by these computers can be presented at any suitable display medium, including a liquid crystal display (LCD).

The technology can also be practiced in distributed environments, where tasks or modules are performed by remote processing devices that are linked through a communications network. In a distributed computing environment, program modules or subroutines may be located in local and remote memory storage devices. Aspects of the technology described below may be stored or distributed on computer-readable media, including magnetic or optically readable or removable computer disks, as well as distributed electronically over networks. Data structures and transmissions of data particular to aspects of the technology are also encompassed within the scope of the embodiments of the technology.

Figure 28:
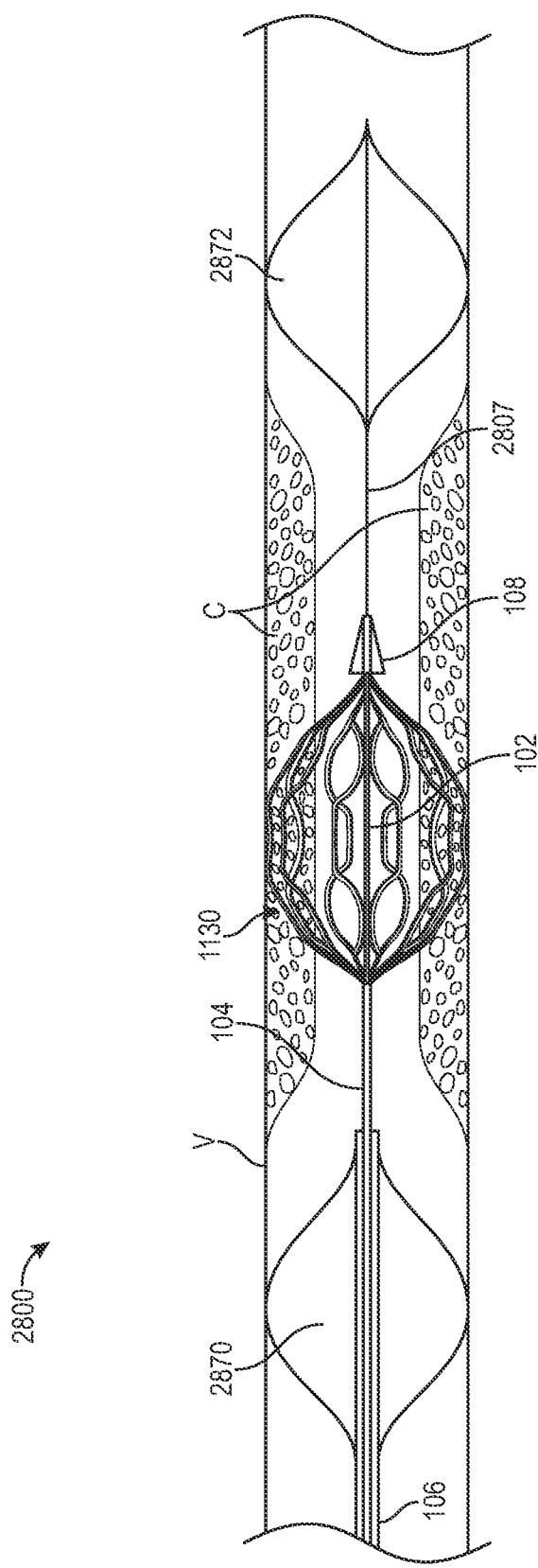
FIG. 28 is a side view of a distal portion of a clot removal system positioned within a vessel to treat clot material in accordance with embodiments of the present technology.

FIG. 28 is a side view of a distal portion of a clot removal system 2800 ("system 2800") positioned within a vessel V to treat clot material C in accordance with embodiments of the present technology. The system 2800 can include some features that are at least generally similar in structure and function, or identical in structure and function, to the corresponding features of the system 100 described in detail above with reference to FIGS. 1A-10C, and can operate in a generally similar or identical manner to the system 100. For example, in the illustrated embodiment, the system 2800 includes the clot treatment device 130, the inner elongate member 102 (obscured in FIG. 28), the middle elongate member 104, the outer elongate member 106, and the tip 108.

In the illustrated embodiment, the system 2800 further includes a first balloon 2870 coupled to the outer elongate member 106 (e.g., coupled to a distal portion thereof) and a second balloon 2872 coupled to an innermost (e.g., fourth) elongate member 2807. The innermost elongate member 2807 can be moved (e.g., advanced and/or retracted) through the lumen in the tip 108 and the inner elongate member 102. The first and second balloons 2870, 2872 can be inflated via one or more components of the handle 110 (FIG. 5), a separate handle, and/or a different inflation component to an inflated state shown in FIG. 28 in which the balloons at least partially engage the wall of the vessel V. Accordingly, the outer elongate member 106, the innermost elongate member 2807, and/or other components of the system 2800 can include one or more inflation lumens (not shown) for inflating the first and second balloons 2870, 2872.

The system 2800 can be used to treat the clot material C when the clot material C is positioned within a bare vessel and/or an implant. The clot material C can be chronic or adherent clot material that may otherwise be difficult to treat and remove. In operation, during a clot removal procedure, the outer elongate member 106 can be positioned proximal to the clot material C such that the first balloon 2870 is positioned proximal to the clot material C within the vessel V. The innermost elongate member 2807 can be positioned such that the second balloon 2872 is distal to the clot material C within the vessel V. The clot treatment devices 130 can be deployed between the first and second balloons 2870, 2872 within the clot material C. With the first and second balloons 2870, 2872 inflated, the clot treatment device 130 can be translated and/or rotated through the clot material C to treat and remove the clot material C as described in detail above with reference to, for example, FIG. 7. In some aspects of the present technology, the first and second balloons 2870, 2872 can help stabilize the vessel V—inhibiting or even prohibiting it from moving—when the clot treatment device 130 is moved to treat the clot material C. This can help improve the treatment efficiency of the system 2800. In some embodiments, the first balloon 2870 and/or the second balloon 2872 can provide embolic protection during a clot treatment procedure with the clot treatment device 130 in addition to or alternatively to vessel stabilization.

Several aspects of the present technology are set forth in the following examples:

1. A system for removing clot material from an implant positioned within a body vessel, comprising:
   a clot treatment device configured to be deployed within the implant, wherein the clot treatment device includes a first end portion, a second end portion, and a plurality of struts extending between the first end portion and the second end portion;
   a handle including an actuator;
   a first elongate member coupling the first end portion of the clot treatment device to the handle; and
   a second elongate member coupling the second end portion of the clot treatment device to the handle, wherein actuation of the actuator is configured to move the second elongate member relative to the first elongate member to reduce a distance between the first end portion and the second end portion to radially expand the struts.

2. The system of example 1 wherein the implant is a stent.

3. The system of example 1 or example 2 wherein the first end portion is a proximal end portion of the clot treatment device, and wherein the second end portion is a distal end portion of the clot treatment device.

4. The system of example 3 wherein the second elongate member extends through a lumen of the first elongate member.

5. The system of example 1 or example 2 wherein the first end portion is a distal end portion of the clot treatment device, and wherein the second end portion is a proximal end portion of the clot treatment device.

6. The system of any one of examples 1-5 wherein actuation of the actuator is configured to move both the first elongate member and the second elongate member relative to the handle.

7. The system of any one of examples 1-6 wherein the handle is rotatable to rotate the clot treatment device relative to the implant.

8. The system of any one of examples 1-7 wherein the handle is longitudinally movable to move the clot treatment device longitudinally relative to the implant.

9. The system of any one of examples 1-8 wherein the handle is rotatable and longitudinally movable to rotate and longitudinally move the clot treatment device relative to the implant.

10. The system of any one of examples 1-9, further comprising a guide catheter, wherein the clot treatment device is configured to be (a) covered within the guide catheter in a first state and (b) uncovered from the guide catheter and expanded to a second state.

11. The system of any one of examples 1-10 wherein the struts extend generally axially between the first and second end portions and each have an undulating shape.

12. The system of any one of examples 1-11 wherein the struts each extend axially between the first and second end portions, and wherein the clot treatment device does not include any cross-members interconnecting the struts.

13. The system of any one of examples 1-12 wherein the actuator is a rotatable knob or a slider.

14. The system of any one of examples 1-13 wherein the handle includes an indicator configured to indicate an amount that the struts are radially expanded.

15. A method of removing clot material from an implant positioned within a body vessel, the method comprising:
    positioning a clot treatment device at least partially within the implant, wherein the clot treatment device has (a) a first end portion, (b) a second end portion, and (c) a plurality of struts extending between the first end portion and the second end portion;
    moving the second elongate member relative to the first elongate member to reduce a distance between the first end portion and the second end portion to radially expand the struts; and
    after radially expanding the struts, rotating and/or translating the clot treatment device within the implant to materially engage the clot material with at least a portion of the struts.

16. The method of example 15 wherein the first end portion of the clot treatment device is coupled to a first elongate member, wherein the second end portion of the clot treatment device is coupled to a second elongate member, and wherein moving the second elongate relative to the first elongate member comprises actuating an actuator on a handle coupled to the first elongate member and the second elongate member to move the second elongate member relative to the first elongate member.

17. The method of example 15 or example 16 wherein the struts each extend axially between the first and second end portions, and wherein the clot treatment device does not include any cross-members interconnecting the struts.

18. The method of any one of examples 15-17 wherein the implant is a stent.

19. A clot treatment device, compressing:
    a proximal end portion;
    a distal end portion; and
    a plurality of struts extending generally axially along a longitudinal axis between the proximal end portion and the distal end portion, wherein
        movement of the first end portion toward the second end portion is configured to radially expand the struts;
        individual ones of the struts include a proximal portion extending from the proximal end portion, a distal portion extending from the distal end portion, and a middle portion (a) extending between the proximal portion and the distal portion and (b) having a hook-like shape in a direction about the longitudinal axis; and
        individual ones of the struts have an undulating shape in a direction along the longitudinal axis.

20. The clot treatment device of example 19 wherein the clot treatment device does not include any cross-members interconnecting the struts.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for removing clot material from an implant positioned within a body vessel, comprising:
    a clot treatment device configured to be deployed within the implant, wherein the clot treatment device includes a first end portion, a second end portion, and a plurality of struts extending between the first end portion and the second end portion;
    a handle including an actuator and an indicator;
    a first elongate member coupling the first end portion of the clot treatment device to the handle; and
    a second elongate member coupling the second end portion of the clot treatment device to the handle, wherein actuation of the actuator is configured to move the second elongate member relative to the first elongate member to reduce a distance between the first end portion and the second end portion to radially expand the struts, and wherein the indicator is configured to indicate an amount that the struts are radially expanded.

2. The system of claim 1 wherein the implant is a stent.

3. The system of claim 1 wherein the first end portion is a proximal end portion of the clot treatment device, and wherein the second end portion is a distal end portion of the clot treatment device.

4. The system of claim 3 wherein the second elongate member extends through a lumen of the first elongate member.

5. The system of claim 1 wherein the first end portion is a distal end portion of the clot treatment device, and wherein the second end portion is a proximal end portion of the clot treatment device.

6. The system of claim 1 wherein actuation of the actuator is configured to move both the first elongate member and the second elongate member relative to the handle.

7. The system of claim 1 wherein the handle is rotatable to rotate the clot treatment device relative to the implant.

8. The system of claim 1 wherein the handle is longitudinally movable to move the clot treatment device longitudinally relative to the implant.

9. The system of claim 1 wherein the handle is rotatable and longitudinally movable to rotate and longitudinally move the clot treatment device relative to the implant.

10. The system of claim 1, further comprising a guide catheter, wherein the clot treatment device is configured to be (a) covered within the guide catheter in a first state and (b) uncovered from the guide catheter and expanded to a second state.

11. The system of claim 1 wherein the struts extend generally axially between the first and second end portions and each have an undulating shape.

12. The system of claim 1 wherein the struts each extend axially between the first and second end portions, and wherein the clot treatment device does not include any cross-members interconnecting the struts.

13. The system of claim 1 wherein the actuator is a rotatable knob or a slider.

14. The system of claim 1 wherein:
the first end portion is a proximal end portion of the clot treatment device;
the second end portion is a distal end portion of the clot treatment device; the plurality of struts extend generally axially along a longitudinal axis between the proximal end portion and the distal end portion;
individual ones of the struts include a proximal portion extending from the proximal end portion, a distal portion extending from the distal end portion, and a middle portion (a) extending between the proximal portion and the distal portion and (b) having a hook-like shape in a direction about the longitudinal axis; and
individual ones of the struts have an undulating shape in a direction along the longitudinal axis.

15. The system of claim 14 wherein the clot treatment device does not include any cross-members interconnecting the struts.

16. A method of removing clot material from an implant positioned within a body vessel, the method comprising:
positioning a clot treatment device at least partially within the implant, wherein the clot treatment device has (a) a first end portion coupled to a first elongate member, (b) a second end portion coupled to a second elongate member, and (c) a plurality of struts extending between the first end portion and the second end portion;
moving the second elongate member relative to the first elongate member to reduce a distance between the first end portion and the second end portion to radially expand the struts;
providing an indication, via an indicator on a handle visible to a user, of an amount that the struts are radially expanded; and
after radially expanding the struts, rotating and/or translating the clot treatment device within the implant to materially engage the clot material with at least a portion of the struts.

17. The method of claim 16 wherein moving the second elongate relative to the first elongate member comprises actuating an actuator on the handle, and wherein the handle is coupled to the first elongate member and the second elongate member to move the second elongate member relative to the first elongate member.

18. The method of claim 16 wherein the struts each extend axially between the first and second end portions, and wherein the clot treatment device does not include any cross-members interconnecting the struts.

19. The method of claim 16 wherein the implant is a stent.

* * * * *